United States Patent
Hölscher et al.

(10) Patent No.: US 10,045,551 B2
(45) Date of Patent: Aug. 14, 2018

(54) USE OF DEFINED CYCLOHEXENONES AS AGENTS FOR THE SUPERADDITIVE ENHANCEMENT OF AN OLFACTORY IMPRESSION AND FRAGRANCE AND/OR FLAVOR MATERIAL COMPOSITION

(71) Applicant: Symrise AG, Holzminden (DE)

(72) Inventors: Bernd Hölscher, Halle (DE); Claudia Ryppa, Holzminden (DE)

(73) Assignee: Symrise AG, Holzminden (DE)

( * ) Notice: Subject to any disclaimer, the term of this patent is extended or adjusted under 35 U.S.C. 154(b) by 67 days.

(21) Appl. No.: 13/935,725

(22) Filed: Jul. 5, 2013

(65) Prior Publication Data

US 2014/0023770 A1    Jan. 23, 2014

(51) Int. Cl.
| | | |
|---|---|---|
| A23L 1/22 | (2006.01) |
| A23L 1/226 | (2006.01) |
| A61Q 13/00 | (2006.01) |
| C07C 49/603 | (2006.01) |
| C11B 9/00 | (2006.01) |
| C11D 3/50 | (2006.01) |
| A23L 2/39 | (2006.01) |
| A23L 2/56 | (2006.01) |
| C11D 3/20 | (2006.01) |
| A61K 8/35 | (2006.01) |
| A23G 3/36 | (2006.01) |
| A23L 27/00 | (2016.01) |
| A23L 27/20 | (2016.01) |
| A61Q 5/02 | (2006.01) |
| A61Q 5/10 | (2006.01) |
| A61Q 5/12 | (2006.01) |
| A61Q 7/02 | (2006.01) |
| A61Q 9/02 | (2006.01) |
| A61Q 11/00 | (2006.01) |
| A61Q 15/00 | (2006.01) |
| A61Q 17/04 | (2006.01) |
| A61Q 19/00 | (2006.01) |
| A61Q 19/10 | (2006.01) |
| A61L 9/01 | (2006.01) |

(52) U.S. Cl.
CPC ............ *A23L 1/2265* (2013.01); *A23G 3/36* (2013.01); *A23L 2/39* (2013.01); *A23L 2/56* (2013.01); *A23L 27/203* (2016.08); *A23L 27/88* (2016.08); *A61K 8/35* (2013.01); *A61Q 13/00* (2013.01); *C07C 49/603* (2013.01); *C11B 9/0003* (2013.01); *C11B 9/0015* (2013.01); *C11B 9/0034* (2013.01); *C11D 3/2072* (2013.01); *C11D 3/50* (2013.01); *A61L 9/01* (2013.01); *A61Q 5/02* (2013.01); *A61Q 5/10* (2013.01); *A61Q 5/12* (2013.01); *A61Q 7/02* (2013.01); *A61Q 9/02* (2013.01); *A61Q 11/00* (2013.01); *A61Q 15/00* (2013.01); *A61Q 17/04* (2013.01); *A61Q 19/00* (2013.01); *A61Q 19/10* (2013.01); *C07C 2601/16* (2017.05)

(58) Field of Classification Search
CPC ...... A23L 1/2265; A23L 27/88; A23L 27/203; A23L 2/39; A23L 2/56; A23G 3/36; A61K 8/35; A61Q 13/00; A61Q 5/02; A61Q 5/10; A61Q 5/12; A61Q 7/02; A61Q 9/02; A61Q 11/00; A61Q 15/00; A61Q 17/04; A61Q 19/00; A61Q 19/10; C07C 49/603; C07C 2601/16; C11B 9/0003; C11B 9/0015; C11B 9/0034; C11D 3/2072; C11D 3/50; A61L 9/01
USPC .................................................. 426/534, 538
See application file for complete search history.

(56) References Cited

U.S. PATENT DOCUMENTS 4,136,119 A * 1/1979 Hunter et al. ................ 568/338
4,485,828 A 12/1984 Klemarczyk

FOREIGN PATENT DOCUMENTS

| DE | 2257121 A1 | 7/1973 |
| DE | 3640591 A1 | 6/1988 |
| EP | 0133548 A1 | 2/1985 |
| WO | 3997102 A2 | 5/2002 |

OTHER PUBLICATIONS

PubChem, https://pubchem.ncbi.nlm.nih.gov/compound/573562#section=Classification, Create Date: Mar. 27, 2005.*
European Patent Search Report dated Nov. 30, 2012 for priority application EP 12176718.0-2114.

* cited by examiner

*Primary Examiner* — Leslie A Wong
(74) *Attorney, Agent, or Firm* — Dilworth & Barrese, LLP

(57) ABSTRACT

A compound of Formula (I)

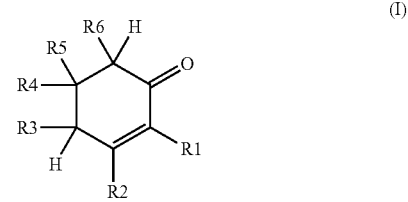

or of a mixture comprising two, three, four, five, six or a plurality of different compounds of Formula (I) for the superadditive enhancement of an olfactory impression. The invention also relates to novel fragrance and/or flavor material compositions which, in addition to a compound of Formula (I) or a mixture thereof, further contains one, two, three or a plurality of further fragrance and/or flavor mate- (Continued)

rials, the fragrance and/or flavor material or the further fragrance and/or flavor materials not being compound of Formula (I).

20 Claims, No Drawings

USE OF DEFINED CYCLOHEXENONES AS AGENTS FOR THE SUPERADDITIVE ENHANCEMENT OF AN OLFACTORY IMPRESSION AND FRAGRANCE AND/OR FLAVOR MATERIAL COMPOSITION

CROSS-REFERENCE TO RELATED APPLICATIONS

This application claims the benefit of EP Patent Application Serial No. 12 176 718.0-2114, filed on 17 Jul. 2012, the benefit of the earlier filing date of which is hereby claimed under 35 USC § 119(a)-(d) and (f). The application is hereby incorporated in its entirety as if fully set forth herein.

BACKGROUND OF THE INVENTION

Field of the Invention

This invention relates generally to the use of agents for the superadditive enhancement of an olfactory impression and fragrance and/or flavor material composition.

BRIEF SUMMARY OF THE INVENTION

Briefly described, in a preferred form, the present invention relates to the use of a compound of Formula (I)

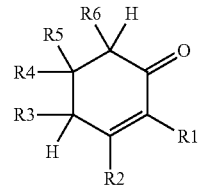

or of a mixture consisting of or comprising two, three, four, five, six or a plurality of different compounds of Formula (I) for the superadditive enhancement of an olfactory impression. The residues R1 through R6 have the meaning defined below.

The invention also relates to novel fragrance and/or flavor material compositions which, in addition to a compound of Formula (I) or a mixture thereof, as respectively defined here, contain one, two, three or a plurality of further fragrance and/or flavor materials, the fragrance and/or flavor material or the further fragrance and/or flavor materials not being compounds of Formula (I).

An olfactory impression is an odor impression which can be described by one or a plurality of descriptors. In the scope of the present text, those olfactory impressions that can be described by one or a plurality of descriptors, which are selected from the group consisting of floral and fruity, are particularly relevant.

A superadditive enhancement of an olfactory impression (also referred to as synergistic enhancement of an olfactory impression) is intended to mean an effect in which, by adding the compound of Formula (I) to one, two, three or a plurality of further fragrance and/or flavor materials, the fragrance and/or flavor material or the further fragrance and/or flavor materials not being compounds of Formula (I), an olfactory impression which is stronger than the sum of the individual olfactory impressions is obtained. If a (further) fragrance and/or flavor material has, for example, a fruity or floral olfactory impression (besides optionally further olfactory impressions), then there is a superadditive enhancement of the olfactory impression when the overall fruity or floral olfactory impression of the resulting mixture comprising the compound of Formula (I) and the (further) fragrance and/or flavor material is stronger than the sum of the floral or fruity olfactory impressions of the compound of Formula (I), on the one hand, and of the (further) fragrance and/or flavor material on the other hand.

The present invention furthermore relates to perfumed and/or aromatized articles, which contain a corresponding fragrance and/or flavor material mixture according to the present invention.

The present invention likewise relates to a method for producing a compound of Formula (I), as well as to a method for the enhancement of an olfactory impression.

The present invention also relates to novel, particularly advantageous compounds of Formula (I) and to corresponding mixtures. Furthermore, the use of the said novel compounds as a fragrance material, flavor material or agent for the superadditive enhancement of an odor is described.

In an exemplary embodiment, the present invention comprises the use of one or more compounds of Formula (I)

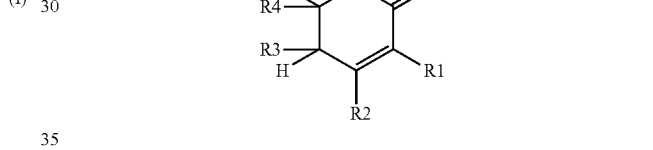

wherein in each of the compounds of Formula (I), the residues R1, R2, R3, R4, R5 and R6 respectively, independently of one another have the following meaning:

R1 denotes hydrogen, methyl or ethyl,

R2 denotes hydrogen, methyl or ethyl,

R3 denotes hydrogen, methyl, ethyl or isopropyl,

R4 denotes hydrogen, methyl, ethyl, n-propyl or isopropyl,

R5 denotes hydrogen or methyl, and

R6 denotes hydrogen, methyl or ethyl, with the proviso that R1 is not methyl or ethyl when R6 is methyl or ethyl, for the superadditive enhancement of an olfactory impression.

The at least one compound of Formula (I) can selected from the group consisting of the following compounds (1) through (61):

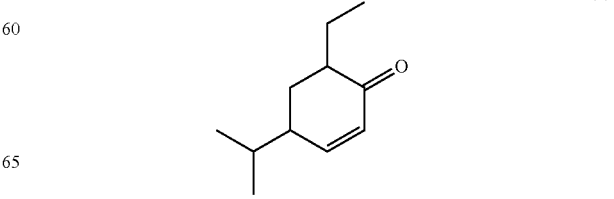

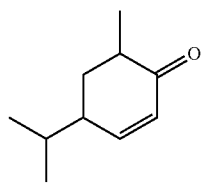 (2)
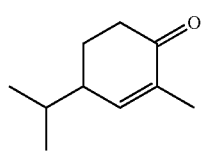 (3)
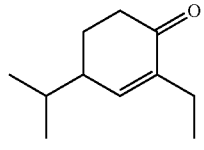 (4)
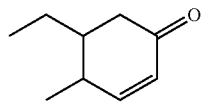 (5)
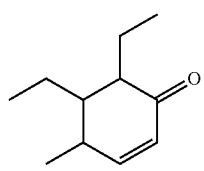 (6)
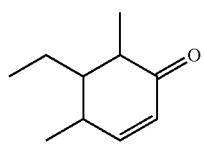 (7)
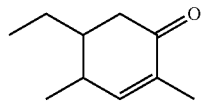 (8)
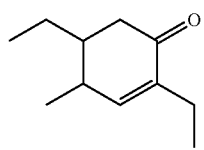 (9)
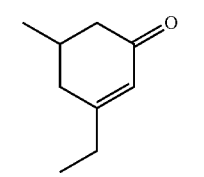 (10)
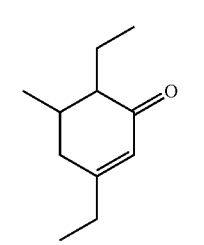 (11)
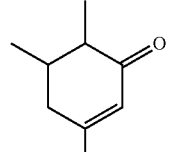 (12)
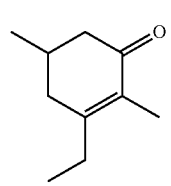 (13)
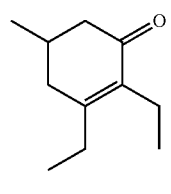 (14)
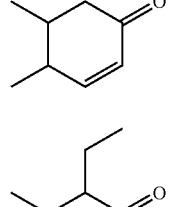 (15)
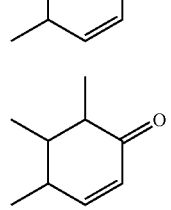 (16)
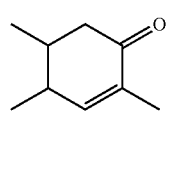 (17)
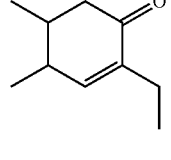 (18)
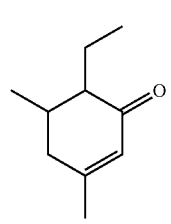 (19)
(20)

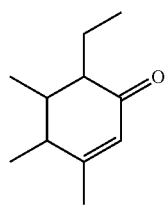 (21)
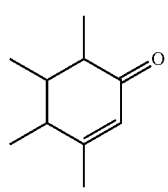 (22)
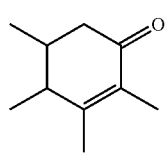 (23)
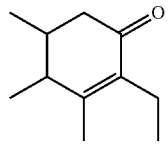 (24)
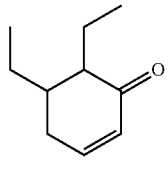 (25)
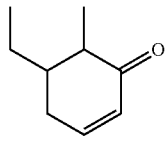 (26)
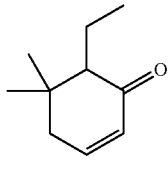 (27)
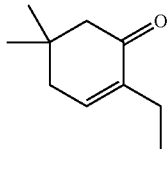 (28)
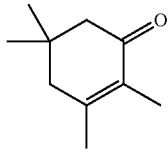 (29)
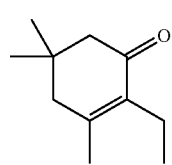 (30)
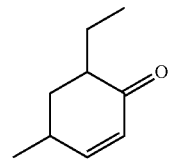 (31)
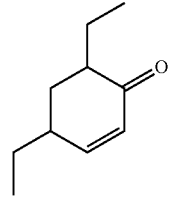 (32)
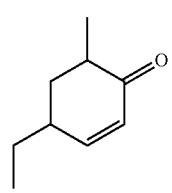 (33)
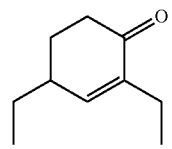 (34)
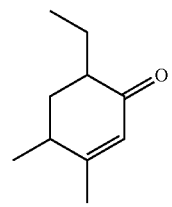 (35)
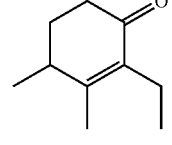 (36)
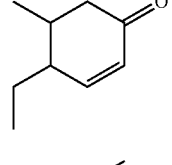 (37)
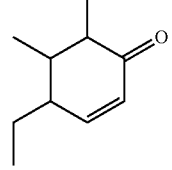 (38)

(39) 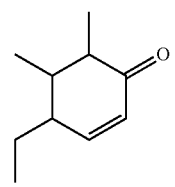
(40) 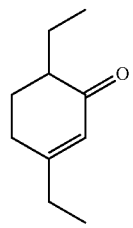
(41) 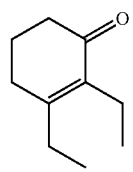
(42) 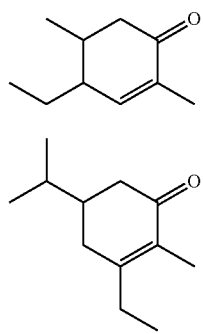
(43)
(44) 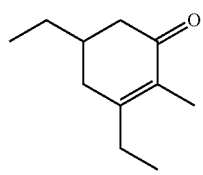
(45) 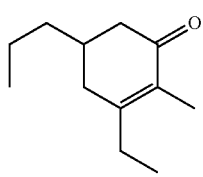
(46) 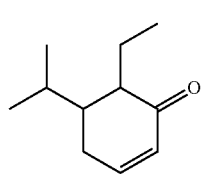
(47) 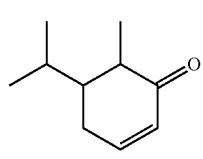
(48) 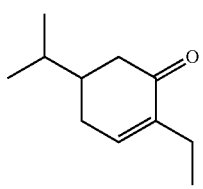
(49) 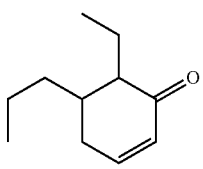
(50) 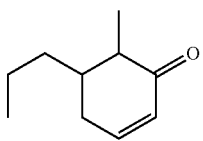
(51) 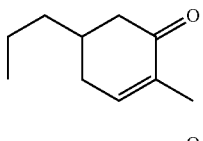
(52) 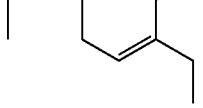
(53) 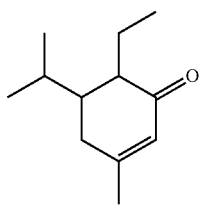
(54) 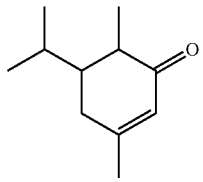
(55) 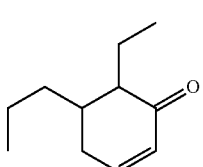
(56) 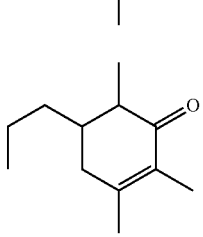

-continued

(57)
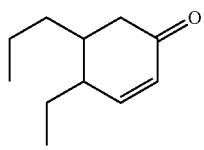

(58)
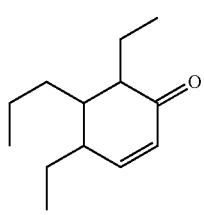

(59)
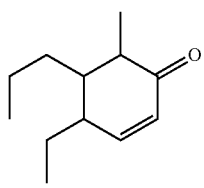

(60)
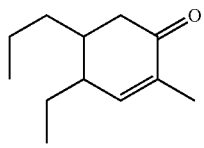

(61)
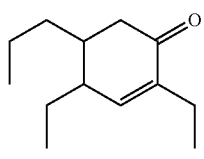

At least one compound of Formula (I) can selected from the group consisting of compounds (2), (4), (13), (23), (29), (43) and (51).

The use can be for the superadditive enhancement of an olfactory impression selected from the group consisting of floral and fruity olfactory impressions.

An olfactory impression to be enhanced may not be selected from the group consisting of nutty, hazelnut, pistachio, cocoa, caramel, meat, roasted grain, chocolate and spicy.

At least one compound of Formula (I) may not impart an olfactory impression selected from the group consisting of nutty, hazelnut, pistachio, cocoa, caramel, meat, roasted grain, chocolate and spicy.

At least one compound of Formula (I) can be selected from the group consisting of 6-ethyl-4-isopropylcyclohex-2-en-1-one (1), 5,6-diethyl-4-methylcyclohex-2-en-1-one (6), 5-ethyl-4,6-dimethylcyclohex-2-en-1-one (7), 2,5-diethyl-4-methylcyclohex-2-en-1-one (9), 3-ethyl-5-methylcyclohex-2-en-1-one (10), 3,6-diethyl-5-methylcyclohex-2-en-1-one (11), 3-ethyl-5,6-dimethylcyclohex-2-en-1-one (12), 2,3-diethyl-5-methylcyclohex-2-en-1-one (14), 6-ethyl-4,5-dimethylcyclohex-2-en-1-one (16), 4,5,6-trimethylcyclohex-2-en-1-one (17), 2,4,5-trimethylcyclohex-2-en-1-one (18), 2-ethyl-4,5-dimethylcyclohex-2-en-1-one (19), 6-ethyl-3,5-dimethylcyclohex-2-en-1-one (20), 6-ethyl-3,4,5-trimethylcyclohex-2-en-1-one (21), 3,4,5,6-tetramethylcyclohex-2-en-1-one (22), 2,3,4,5-tetramethylcyclohex-2-en-1-one (23), 2-ethyl-3,4,5-trimethylcyclohex-2-en-1-one (24), 5,6-diethylcyclohex-2-en-1-one (25), 5-ethyl-6-methylcyclohex-2-en-1-one (26), 6-ethyl-5,5-dimethylcyclohex-2-en-1-one (27), 2-ethyl-5,5-dimethylcyclohex-2-en-1-one (28), 6-ethyl-4-methylcyclohex-2-en-1-one (31), 4,6-diethylcyclohex-2-en-1-one (32), 4-ethyl-6-methylcyclohex-2-en-1-one (33), 2,4-diethylcyclohex-2-en-1-one (34), 6-ethyl-3,4-dimethylcyclohex-2-en-1-one (35), 2-ethyl-3,4-dimethylcyclohex-2-en-1-one (36), 4-ethyl-5-methylcyclohex-2-en-1-one (37), 4,6-diethyl-5-methylcyclohex-2-en-1-one (38), 4-ethyl-5,6-dimethylcyclohex-2-en-1-one (39), 3,6-diethylcyclohex-2-en-1-one (40), 2,3-diethylcyclohex-2-en-1-one (41), 4-ethyl-2,5-dimethylcyclohex-2-en-1-one (42), 3-ethyl-5-isopropyl-2-methylcyclohex-2-en-1-one (43), 3,5-diethyl-2-methylcyclohex-2-en-1-one (44), 3-ethyl-2-methyl-5-n-propylcyclohex-2-en-1-one (45), 6-ethyl-5-isopropylcyclohex-2-en-1-one (46), 5-isopropyl-6-methylcyclohex-2-en-1-one (47), 2-ethyl-5-isopropylcyclohex-2-en-1-one (48), 6-ethyl-5-n-propylcyclohex-2-en-1-one (49), 6-methyl-5-n-propylcyclohex-2-en-1-one (50), 2-methyl-5-n-propylcyclohex-2-en-1-one (51), 2-ethyl-5-n-propylcyclohex-2-en-1-one (52), 6-ethyl-5-isopropyl-3-methylcyclohex-2-en-1-one (53), 5-isopropyl-3,6-dimethylcyclohex-2-en-1-one (54), 6-ethyl-3-methyl-5-n-propylcyclohex-2-en-1-one (55), 3,6-dimethyl-5-n-propylcyclohex-2-en-1-one (56), 4-ethyl-5-n-propylcyclohex-2-en-1-one (57), 4,6-diethyl-5-n-propylcyclohex-2-en-1-one (58), 4-ethyl-6-methyl-5-n-propylcyclohex-2-en-1-one (59), 4-ethyl-2-methyl-5-n-propylcyclohex-2-en-1-one (60) and 2,4-diethyl-5-n-propylcyclohex-2-en-1-one (61).

In another exemplary embodiment, the present invention comprises one or more compounds of Formula (I), wherein at least one compound of Formula (I) is selected from the group consisting of 2,3,4,5-tetramethylcyclohex-2-en-1-one (23), 3-ethyl-5-isopropyl-2-methylcyclohex-2-en-1-one (43) and 2-methyl-5-n-propylcyclohex-2-en-1-one (51).

In another exemplary embodiment, a fragrance and/or flavor material composition comprises one or more compounds of Formula (I) and one or more compounds not comprising Formula (I), wherein at least one of the one or more compounds not comprising Formula (I) has one or both of a floral and fruity odor.

At least one of the one or more compounds not comprising Formula (I) may not impart an olfactory impression selected from the group consisting of nutty, hazelnut, pistachio, cocoa, caramel, meat, roasted grain, chocolate and spicy, and wherein the olfactory impression is not being enhanced superadditively.

At least one of the one or more compounds not comprising Formula (I) may imparts an olfactory impression selected from the group consisting of nutty, hazelnut, pistachio, cocoa, caramel, meat, roasted grain, chocolate and spicy, and wherein the olfactory impression is not being enhanced superadditively.

At least one of the one or more compounds Formula (I) may not impart an olfactory impression selected from the group consisting of nutty, hazelnut, pistachio, cocoa, caramel, meat, roasted grain, chocolate and spicy.

At least one of the one or more compounds not comprising Formula (I) may not contain fragrance and/or flavor materials that have a pyrazine basic structure.

At least one of the one or more compounds of Formula (I) can enhance at least one olfactory impressions of at least one of the one or more compounds not comprising Formula (I).

The total amount of the one or more compounds of Formula (I) can be in the range of from 0.0001 wt. %, through 90 wt. % based on the total weight of the fragrance and/or flavor material composition, more preferably in the range of from 0.01 wt. %, through 70 wt. %, more preferably in the range of from 0.1 wt. %, through 50 wt. %, more preferably in the range of from 0.1 wt. %, through 30 wt. %, or most preferably in the range of from 0.1 wt. %, through 10 wt. % based on the total weight of the fragrance and/or flavor material composition.

In another exemplary embodiment, the present invention comprises a perfumed and/or aromatized article comprising a fragrance and/or flavor material composition comprising one or more compounds of Formula (I).

The article can further comprising a carrier or a substrate that is in direct contact with at least one of the one or more compounds of Formula (I).

In another exemplary embodiment, the present invention comprises a method for the enhancement of an olfactory impression of a product comprising bringing in contact at least one compound of Formula (I) with the product.

The method can comprise providing or producing a compound of Formula (IV)

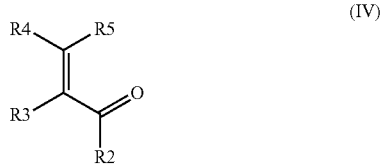

and
reacting the compound of Formula (IV) and a compound of Formula (V),

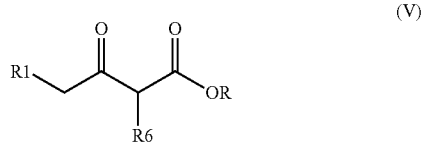

so that a compound of Formula (I) results.

The step of providing or producing a compound of Formula (IV) can comprise reacting a compound of Formula (II) and a compound of Formula (III), so that a compound of Formula (IV) results,

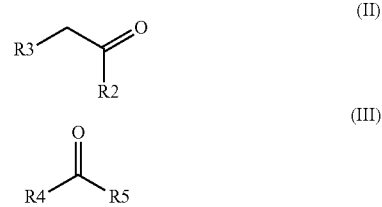

Further aspects of the present invention and preferred configurations thereof can be seen from the following description, the exemplary embodiments and the claims.

DETAILED DESCRIPTION OF THE PREFERRED EMBODIMENTS

To facilitate an understanding of the principles and features of the various embodiments of the invention, various illustrative embodiments are explained below. Although exemplary embodiments of the invention are explained in detail, it is to be understood that other embodiments are contemplated. Accordingly, it is not intended that the invention is limited in its scope to the details of construction and arrangement of components set forth in the following description or illustrated in the drawings. The invention is capable of other embodiments and of being practiced or carried out in various ways. Also, in describing the exemplary embodiments, specific terminology will be resorted to for the sake of clarity.

It must also be noted that, as used in the specification and the appended claims, the singular forms "a," "an" and "the" include plural references unless the context clearly dictates otherwise. For example, reference to a component is intended also to include composition of a plurality of components. References to a composition containing "a" constituent is intended to include other constituents in addition to the one named.

Also, in describing the exemplary embodiments, terminology will be resorted to for the sake of clarity. It is intended that each term contemplates its broadest meaning as understood by those skilled in the art and includes all technical equivalents which operate in a similar manner to accomplish a similar purpose.

Ranges may be expressed herein as from "about" or "approximately" or "substantially" one particular value and/or to "about" or "approximately" or "substantially" another particular value. When such a range is expressed, other exemplary embodiments include from the one particular value and/or to the other particular value.

Similarly, as used herein, "substantially free" of something, or "substantially pure", and like characterizations, can include both being "at least substantially free" of something, or "at least substantially pure", and being "completely free" of something, or "completely pure".

By "comprising" or "containing" or "including" is meant that at least the named compound, element, particle, or method step is present in the composition or article or method, but does not exclude the presence of other compounds, materials, particles, method steps, even if the other such compounds, material, particles, method steps have the same function as what is named.

It is also to be understood that the mention of one or more method steps does not preclude the presence of additional method steps or intervening method steps between those steps expressly identified. Similarly, it is also to be understood that the mention of one or more components in a composition does not preclude the presence of additional components than those expressly identified.

The materials described as making up the various elements of the invention are intended to be illustrative and not restrictive. Many suitable materials that would perform the same or a similar function as the materials described herein are intended to be embraced within the scope of the invention. Such other materials not described herein can include, but are not limited to, for example, materials that are developed after the time of the development of the invention.

In the fragrance material industry, there is a constant need to emphasize (accentuate) and/or superadditively enhance particular odor aspects of a fragrance material and/or flavor material, or a fragrance material and/or flavor material mixture. In particular, there is constantly a need to emphasize (accentuate) and/or superadditively enhance floral and/or fruity olfactory impressions of fragrance materials and/or flavor materials, or fragrance material and/or flavor material mixtures.

It is an object of the present invention to superadditively enhance particular odor aspects of fragrance and/or flavor materials, or fragrance material and/or flavor material mixtures. This object is achieved by the use
of a compound of Formula (I)

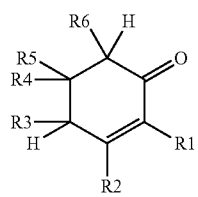

(I)

or
of a mixture consisting of or comprising (preferably consisting of) two, three, four, five, six or a plurality of different compounds of Formula (I),
wherein in each of the compounds of Formula (I) the residues R1, R2, R3, R4, R5 and R6 respectively independently of one another have the following meaning
R1 denotes hydrogen, methyl or ethyl,
R2 denotes hydrogen, methyl or ethyl,
R3 denotes hydrogen, methyl, ethyl or isopropyl,
R4 denotes hydrogen, methyl, ethyl, n-propyl or isopropyl,
R5 denotes hydrogen or methyl,
R6 denotes hydrogen, methyl or ethyl,
with the proviso that R1 is not methyl or ethyl when R6 is methyl or ethyl,
for the superadditive enhancement of an olfactory impression.

In the scope of the present invention, novel compounds of Formula (I) above and corresponding mixtures have also been found. These are described below.

It was particularly surprising that precisely the compounds of Formula (I) described herein are suitable for the purposes of the present invention. This is because the search for suitable agents for the superadditive enhancement of an olfactory impression was—and usually is—made more difficult by the following situations:

The mechanisms of fragrance perception are (still) not sufficiently known.

The relationships between the special fragrance perception, on the one hand, and the chemical structure of the associated fragrance material, on the other hand, are (still) not sufficiently researched.

Often, even minor changes in the structural arrangement of a known fragrance material or of an agent for the superadditive enhancement of an olfactory impression lead to large changes in the sensory (or other) properties. These may furthermore compromise compatibility with the human body.

The mechanism of the enhancement of olfactory impressions is (still) not sufficiently researched. Thus, predictions cannot be made as to whether and when a compound is capable of enhancing an olfactory impression of another substance.

It is not predictable how—starting from a predetermined basic structure—structural changes affect the interactions of a respective compound with other fragrance or flavor materials, the odor of which is for example intended to be enhanced. The resulting sensory (and optionally also other) properties of a corresponding fragrance and/or flavor material composition are therefore not predictable.

Depending on the meaning which the residues R1 through R6 in the compound of Formula (I) have, there may be different stereo centers in the compound of Formula (I). A compound of Formula (I), or the mixtures thereof, may in this case respectively be present as pure configurational isomers in which all the stereo centers have the same arrangement, or as mixtures of configurational isomers. In the case of a mixture of different configurational isomers, this mixture will not be referred to as a mixture in the scope of the present text if the residues R1 through R6 have the same meaning Surprisingly, some of the compounds of Formula (I), or the mixtures thereof, have particularly pronounced properties for the superadditive enhancement of an olfactory impression. Correspondingly, the use according to the invention of a single compound or a mixture is particularly preferred, the individual compound of Formula (I) or one, a plurality of or all compounds of Formula (I) is, or respectively independently of one another are, selected from the group consisting of the following compounds (1) through (61), preferably selected from the group consisting of compounds (2), (4), (13), (23), (29). (43) and (51):

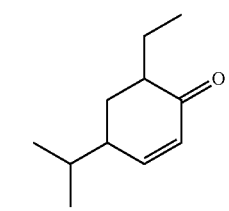

(1)

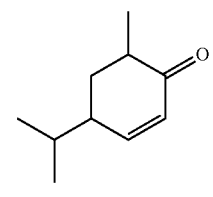

(2)

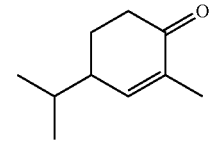

(3)

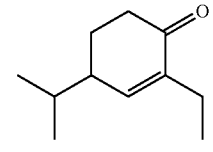

(4)

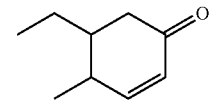

(5)

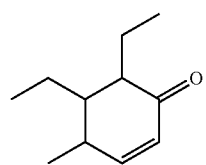 (6)
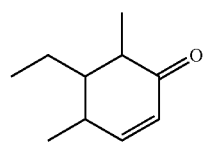 (7)
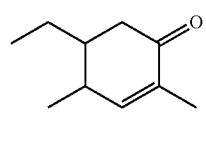 (8)
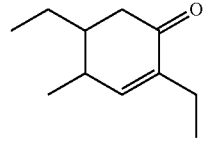 (9)
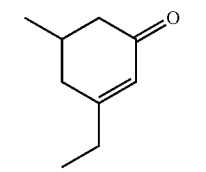 (10)
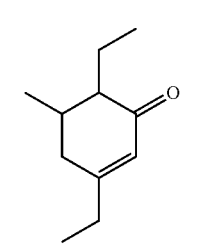 (11)
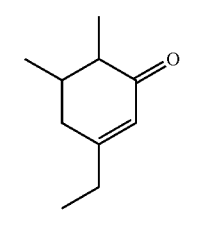 (12)
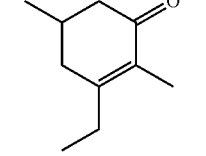 (13)
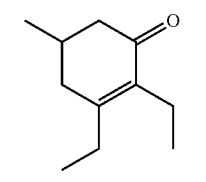 (14)
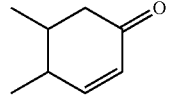 (15)
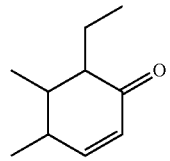 (16)
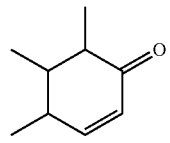 (17)
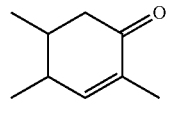 (18)
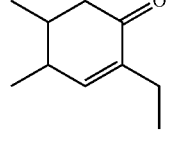 (19)
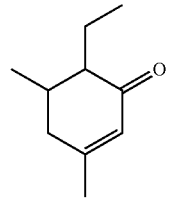 (20)
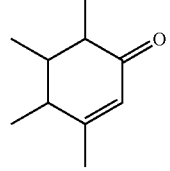 (21)
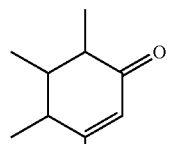 (22)
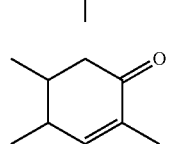 (23)
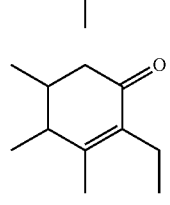 (24)

-continued (25)

(26)

(27)

(28)

(29)

(30)

(31)

(32)

(33)

-continued (34)

(35)

(36)

(37)

(38)

(39)

(40)

(41)

(42)

-continued
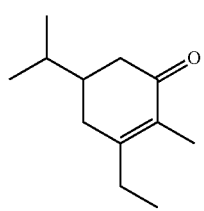
(43)
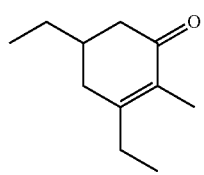
(44)
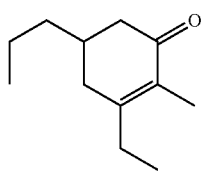
(45)
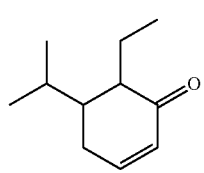
(46)
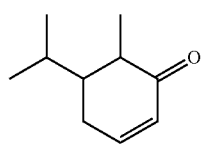
(47)
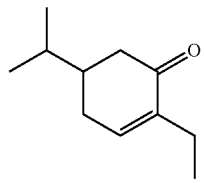
(48)
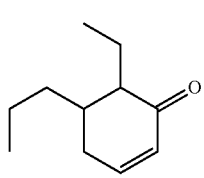
(49)
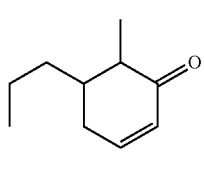
(50)
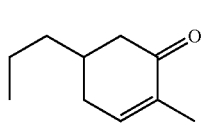
(51)
-continued
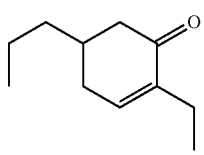
(52)
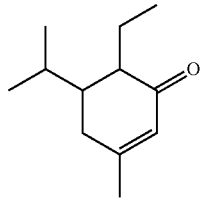
(53)
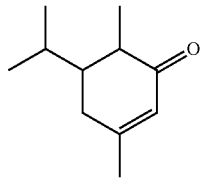
(54)
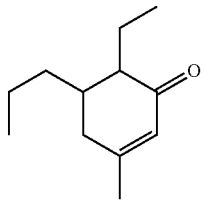
(55)
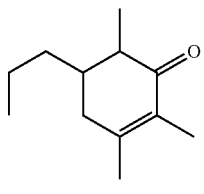
(56)
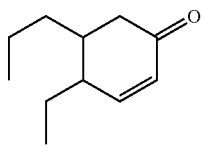
(57)
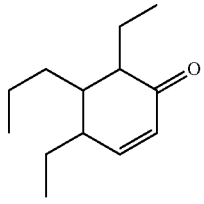
(58)
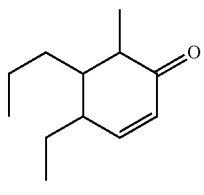
(59)

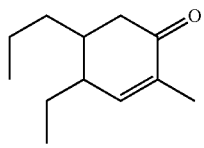

(60)

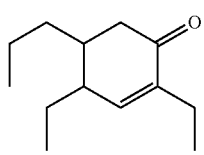

(61)

Surprisingly, it has been found that the compound of Formula (I), or a mixture consisting of or comprising two, three, four, five, six or a plurality of different compounds of Formula (I), as described above can superadditively enhance floral and/or fruity olfactory impressions in particular. A use according to the invention as an odor enhancer for the superadditive enhancement of floral and/or fruity olfactory impressions is therefore particularly preferred.

By the use of the compound of Formula (I), or of a mixture consisting of or comprising two, three, four, five, six or a plurality of different compounds of Formula (I), as described above, floral and/or fruity fragrance notes can be enhanced superadditively even with low dosing in the resulting fragrance and/or flavor material compositions, the overall odor impression furthermore generally being notably harmonized and the radiance perceptively increased (cf. Example 42).

The compound of Formula (I), or of a mixture consisting of or comprising two, three, four, five, six or a plurality of different compounds of Formula (I), as described above are outstandingly suitable as agents for the superadditive enhancement of an olfactory impression in particular a floral and/or fruity olfactory impression.

In resulting compositions, some olfactory impressions are often not advantageous. A use according to the invention is correspondingly particularly preferred wherein the olfactory impression to be enhanced is not selected from the group consisting of nutty, hazelnut, pistachio, cocoa, caramel, meat, roasted grain, chocolate and spicy and/or wherein the compound of Formula (I) or the corresponding mixture (as defined above) does not impart an olfactory impression which is selected from the group consisting of nutty, hazelnut, pistachio, cocoa, caramel, meat, roasted grain, chocolate and spicy.

In a use according to the invention of a compound of Formula (I), or of a mixture consisting of or comprising two, three, four, five, six or a plurality of different compounds of Formula (I), the person skilled in the art will select the proportion of the compound of Formula (I) or of the mixture of compounds of Formula (I) in such a way that the effect of the superadditive enhancement of a fragrance note desired by him is achieved, in which case he will preferably take care on the one hand not to use excessive amounts of the compound of Formula (I) or of the mixture of compounds of Formula (I), which might dominate the overall sensory impression of a resulting fragrance and/or flavor material composition and, on the other hand, not merely to provide so low an amount of the compound of Formula (I) or of the mixture of compounds of Formula (I) that enhancement of odor aspects is not detectable, or detectable not to a significant extent. Since the compounds of Formula (I) used for the superadditive enhancement may have an intrinsic odor, it is naturally also possible to use this intrinsic odor of the compounds of Formula (I) in a fragrance and/or flavor material composition (as described below) so that, besides the desired effect of the superadditive enhancement of a fragrance note, the intrinsic odor of the compound of Formula (I) used is exploited.

In view of the prior art, it was particularly surprising that it was now possible to identify particularly valuable novel agents for the superadditive enhancement of an olfactory impression. Furthermore, the compounds of Formula (I) to be used according to the invention, in particular the novel compounds of Formula (I), have independent olfactory properties. In this case, in particular, the novel compounds of Formula (I) have fragrance notes which are surprising, in this regard see below. An odor enhancing effect of the compounds of Formula (I) to be used according to the invention had not previously been described.

A selection of known cyclohexenones is summarized below:

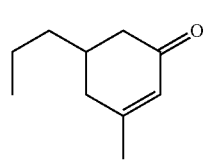

(ii)

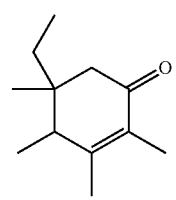

(iii)

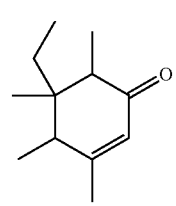

(iv)

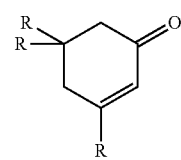

(v)

(R = Me, Et, Pr)

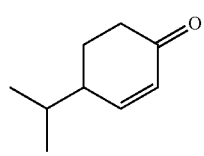

(vi)

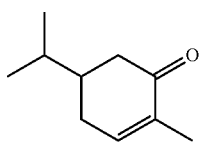

(vii)

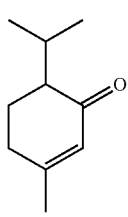
(viii)

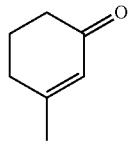
(ix)

Known cyclohexenones having already known sensory properties are:
livescone (ii),
substances (iii) and (iv) (Federal Register 1967, 32, 7946),
isophorone (v, R=Me),
cryptone (vi) (DE 2551172 A1),
carvotanacetone (vii) (J. Chem. Soc., Trans. 1898, 73, 852),
piperitone (viii) and
seudenone (ix).

The organoleptic properties of compound (ix) (seudenone) are described in Perfumer & Flavorist 1998, 23, 56 as sweet, nutty, phenolic, walnut, fruity and almond.

In DE 25 511 72 A1, compound (2) (as described above) is described as strong, balsamic, woody, licorice, slightly fruity, and in DE 36 40 591 A1 compound (3) is described as sweet, herby with an aniseed note and compound (4) is described as flowery, herby, sweetish, woody. In studies by us, it was surprisingly found that compound (2) has an odor which is not as described in DE 25 511 72 A1. The odor description is, according to the studies by us: fresh, sweet, spicy, aromatic, fruity, grapefruit, wormwood. (Cf. Example 2).

In Liebigs Ann. 1911, 379, 215, substance (3) is described as like pinocarvone (according to S. Arctander, Perfume and Flavor Materials: camphoric, minty).

In Chem. Ber. 1948, 81, 197, compound (30) is described as a compound having an odor similar to terpene.

In J. Econ. Entomol. 1971, 64, 970, the use of compound (ix) as an attractant for bark beetles is described.

Compounds of general Formula (V) (isophorone when R=Me) are described in WO 8500096 A1 as repellents for birds.

Some compounds of general Formula (I) are known as reactants or intermediates for or in various reactors, without fragrance or flavor properties being described. For example, compound (5) is used for the preparation of benzoquinones (Org. Biomol. Chem. 2005, 3, 3479), compounds (8) and 13) result from the acid-catalyzed rearrangement of camphor (Tetrahedron 1976, 32, 1699) and carvomenthone (Bull. Soc. Chim. Fr. 1978, 255). By alpha alkylation of isophorone (Compt. Rend. 1953, 237, 910) or isophorone carboxylate (Bull. Soc. Chim. Fr. 1954, 690), compounds (29) and (30) are obtained, which are used inter alia as starting materials for the preparation of light-sensitive materials (U.S. Pat. No. 5,356,769 A) or for the formation of steroid skeletons (J. Am. Chem. Soc. 1993, 115, 504). See also the following cited patent literature: WO 2012041820 A1, WO 2009066193 A1, WO 2009044310 A1, WO 2007135582 A1, WO 2004000776 A1, WO 2009039675 A1, JP 60045544, JP 60032745, JP 200302722 A, CH 603071 A5 and U.S. Pat. No. 4,418,087 A.

Compounds which do not fall under general Formula (I), but which have individual structural correspondences with the compounds according to the invention of general Formula (I), may be found in the following cited patent literature: U.S. Pat. No. 4,326,997 A, U.S. Pat. No. 4,326,996 A and CH 611159 A.

In DE 22 57 121, the compounds 5-ethylcyclohexen-2-one and 6-ethylcyclohexen-2-one are described as agents to improve, intensify or modify organoleptic properties. Furthermore, cyclohexenones of a general Formula II are indicated in as a constituent of a composition which additionally contains at least one pyrazine or pyrazine derivative. Particular cyclohexenones are described as flavor modifiers, the flavor notes of the respective compounds themselves not been described.

As described above, the present invention also relates to novel compounds of Formula (I) and corresponding mixtures. Accordingly, another aspect of the present invention relates to (A) a compound according to the invention of Formula (I)

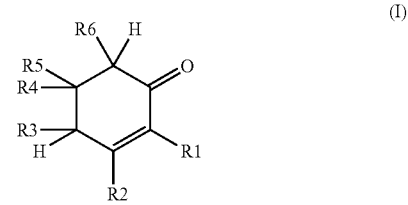
(I)

or (B) a mixture consisting of or comprising two, three, four, five, six or a plurality of different compounds of Formula (I) according to the invention, wherein the compound of Formula (I) or respectively one, a plurality of or all compounds of Formula (I) is, or respectively independently of one another are, selected from the group consisting of the following compounds:
6-ethyl-4-isopropylcyclohex-2-en-1-one (1), 5,6-diethyl-4-methylcyclohex-2-en-1-one (6), 5-ethyl-4,6-dimethylcyclohex-2-en-1-one (7), 2,5-diethyl-4-methylcyclohex-2-en-1-one (9), 3-ethyl-5-methylcyclohex-2-en-1-one (10), 3,6-diethyl-5-methylcyclohex-2-en-1-one (11), 3-ethyl-5,6-dimethylcyclohex-2-en-1-one (12), 2,3-diethyl-5-methylcyclohex-2-en-1-one (14), 6-ethyl-4,5-dimethylcyclohex-2-en-1-one (16), 4,5,6-trimethylcyclohex-2-en-1-one (17), 2,4,5-trimethylcyclohex-2-en-1-one (18), 2-ethyl-4,5-dimethylcyclohex-2-en-1-one (19), 6-ethyl-3,5-dimethylcyclohex-2-en-1-one (20), 6-ethyl-3,4,5-trimethylcyclohex-2-en-1-one (21), 3,4,5,6-tetramethylcyclohex-2-en-1-one (22), 2,3,4,5-tetramethylcyclohex-2-en-1-one (23), 2-ethyl-3,4,5-trimethylcyclohex-2-en-1-one (24), 5,6-diethylcyclohex-2-en-1-one (25), 5-ethyl-6-methylcyclohex-2-en-1-one (26), 6-ethyl-5,5-dimethylcyclohex-2-en-1-one (27), 2-ethyl-5,5-dimethylcyclohex-2-en-1-one (28), 6-ethyl-4-methylcyclohex-2-en-1-one (31), 4,6-diethylcyclohex-2-en-1-one (32), 4-ethyl-6-methylcyclohex-2-en-1-one (33), 2,4-diethylcyclohex-2-en-1-one (34), 6-ethyl-3,4-dimethylcyclohex-2-en-1-one (35), 2-ethyl-3,4-dimethylcyclohex-2-en-1-one (36), 4-ethyl-5-methylcyclohex-2-en-1-one (37), 4,6-diethyl-5-methylcyclohex-2-en-1-one (38), 4-ethyl-5,6-dimethylcyclohex-2-en-1-one (39), 3,6-diethylcyclohex-2-en-1-one (40), 2,3-diethylcyclohex-2-en-1-one (41), 4-ethyl-2,5-dimethylcyclohex-2-en-1-one (42), 3-ethyl-5-isopropyl-2-methylcyclohex-2-en-1-one (43), 3,5-diethyl-2-methylcyclohex-2-en-1-one (44), 3-ethyl-2-methyl-5-n-propylcyclohex-2-en-1-one (45), 6-ethyl-5-isopropylcyclohex-2-en-1-one (46), 5-isopropyl-6-methylcyclohex-2-en-1-one (47), 2-ethyl-5-isopropylcyclohex-2-en-1-one (48), 6-ethyl-5-n-propylcyclohex-2-en-1-one (49), 6-methyl-5-n-propylcyclohex-2-en-1-one (50), 2-methyl-5-n-propylcyclohex-2-en-1-one (51), 2-ethyl-5-n-propylcyclohex-2-en-1-one (52), 6-ethyl-5-isopropyl-3-methylcyclohex-2-en-1-one (53), 5-isopropyl-3,6-dimethylcyclohex-2-en-1-one (54), 6-ethyl-3-methyl-5-n-propylcyclohex-2-en-1-one (55), 3,6-dimethyl-5-n-propylcyclohex-2-en-1-one (56), 4-ethyl-5-n-propylcyclohex-2-en-1-one (57), 4,6-diethyl-5-n-propylcyclohex-2-en-1-one (58), 4-ethyl-6-methyl-5-n-propylcyclohex-2-en-1-one (59), 4-ethyl-2-methyl-5-n-propylcyclohex-2-en-1-one (60) and 2,4-diethyl-5-n-propylcyclohex-2-en-1-one (61), preferably selected from the group consisting of 2,3,4,5-tetramethylcyclohex-2-en-1-one (23), 3-ethyl-5-isopropyl-2-methylcyclohex-2-en-1-one (43) and 2-methyl-5-n-propylcyclohex-2-en-1-one (51).

The numbers used in brackets after the IUPAC designation of the individual compounds refer to the structural formulae given above. If in an individual case an IUPAC designation does not correspond to a structural formula mentioned, both compounds mentioned should be taken into account (according to the structural formula and according to the IUPAC designation).

The novel compounds of Formula (I) and corresponding mixtures are particularly highly suitable for the superadditive enhancement of an odor, in particular for the superadditive enhancement of a floral and/or fruity olfactory impression.

A corresponding mixture (B) comprising two, three, four, five, six or a plurality of different compounds of Formula (I) according to the invention may be formed in the manner of a fragrance enhancer concentrate which is intended to be added to the base preparations in order to superadditively enhance the olfactory impression of the base preparation, for example forming a particularly valuable fragrance and/or flavor material composition. A preferred mixture according to the invention correspondingly comprises no fragrance and/or flavor material which is not a compound of Formula (I) as defined above, and also no fragrance enhancer which is not a compound of Formula (I) as described above.

On page 20, with reference to further publications, laid-open specification DE 22 57 121 discloses a range of compounds, namely cyclohexen-2-one, 2-methyl-cyclohexen-2-one, 3-methylcyclohexen-2-one, 4-methylcyclohexen-2-one, 5-methylcyclohexen-2-one, 6-methylcyclohexen-2-one, 2,6-dimethylcyclohexen-2-one, 3,4-dimethylcyclohexen-2-one, 3,5-dimethylcyclohexen-2-one, 3,6-dimethylcyclohexen-2-one, 4,6-dimethylcyclohexen-2-one, 2,3-dimethylcyclohexen-2-one, 2,4-dimethylcyclohexen-2-one, 2,5-dimethylcyclohexen-2-one, 4,5-dimethylcyclohexen-2-one, 5,6-dimethylcyclohexen-2-one, 2,6-dimethylcyclohexen-2-one, 2-ethylcyclohexen-2-one, 3-ethylcyclohexen-2-one, 4-ethylcyclohexen-2-one, 5-ethylcyclohexen-2-one and 6-ethylcyclohexen-2-one. The respectively selected designation does not always seem to be correct in this case. The compounds disclosed are no more subject-matter of the present invention, as are the corresponding compounds which are disclosed in the underlying publications. Preferably, one, two or a plurality of, preferably all compounds of Formula (I) in the mixture is not selected from the group of the said compounds. In many cases, a specified compound of Formula (I) comprises a plurality of configurational isomers; in the present text, explicit distinction will not generally be made between these configurational isomers. Each reference to a compound of Formula (I) which comprises a plurality of configurational isomers is to be understood in the present text as a reference both to each individual one of the said configurational isomers and as a reference to each individual one of the conceivable mixtures of two or (if present) a plurality of the said configurational isomers. For example, the reference to 6-ethyl-4-isopropylcyclohex-2-en-1-one therefore corresponds to a reference to each individual one of the configurational isomers of 6-ethyl-4-isopropylcycloshex-2-en-1-one, as well as to any arbitrary mixture of these configurational isomers. In the examples below, specific information regarding the compounds used or studied may be found from the analytical data indicated.

Surprisingly, it has been found that the novel compounds of Formula (I) (as described above) respectively also have a particularly interesting odor and/or flavor. This is surprising despite a structural similarity of these novel compounds with the known compounds, since, from the structure of a known first compound having known sensory properties and from its structural similarity with the structure of a second compound, it is not possible to infer the odor or flavor of this second compound. From the literature, many examples are known in which, even as a result of very minor variations of the chemical structure (for example replacement of methyl groups by hydrogen), initially odorless substances subsequently have an odor. Regarding the impossibility of the odor prediction, see C. S. Sell, Angew. Chem. 2006, 118, 6402. In the present situation, it is therefore surprising that the novel compounds of Formula (I) have an odor and/or flavor and that this odor and/or flavor has separate organoleptic, in particular olfactory and/or gustatory properties, which differ significantly from the known compounds and even surpass the latter. In particular, the fragrance notes spicy, saffron, coumarin, aromatic, leather and/or tobacco, which are often to be found in the novel compounds, differ greatly from the fragrance notes known from the prior art for cyclohex-2-en-1-one compounds.

The present invention therefore also relates to the use of the corresponding compounds (1), (2), (3), (4), (5), (8), (9), (10), (12), (13), (14), (15), (18), (19), (23), (24), (28), (29), (30), (31), (32), (33), (34), (37), (40), (41), (42), (43), (44), (45), (48), (51), (52), (57), (60) and (61) as a fragrance material having one, two, three, four, five or all fragrance notes selected from the group consisting of aniseed, spicy, saffron, coumarin, aromatic, leather and tobacco.

Particularly preferred is the combined, i.e. simultaneous use of compounds (1), (2), (3), (4), (5), (8), (9), (10), (12), (13), (14), (15), (18), (19), (23), (24), (28), (29), (30), (31), (32), (33), (34), (37), (40), (41), (42), (43), (44), (45), (48), (51), (52), (57), (60) and (61) for the superadditive enhancement of an olfactory impression (preferably for the superadditive enhancement of a floral and/or fruity olfactory impression) and as a fragrance material having one, two, three, four, five or all fragrance notes selected from the group consisting of spicy, aniseed, saffron, coumarin, aromatic, leather and tobacco.

Surprisingly, some of the novel compounds, in particular those referred to above as preferred, have a particularly valuable spicy fragrance note, cf. in this regard the examples below.

The present invention therefore also relates to the use of the corresponding compounds (2), (3), (4), (5), (8), (9), (10), (12), (13), (14), (18), (19), (23), (24), (28), (29), (30), (32), (33), (34), (42), (43), (44), (45), (48), (51), (57) and (61) as a fragrance material having a spicy note.

Surprisingly, some of the novel compounds, in particular those referred to above as preferred, have a particularly valuable saffron fragrance note, cf. in this regard the examples below.

The present invention therefore also relates to the use of the corresponding compounds (4), (9), (12), (13), (14), (19), (23), (24), (28), (41) and (30) as a fragrance material having a saffron note.

Surprisingly, some of the novel compounds, in particular those referred to above as preferred, have a particularly valuable coumarin fragrance note, cf. in this regard the examples below.

The present invention therefore also relates to the use of the corresponding compounds (8), (15), (18) and (34) as a fragrance material having a coumarin note.

Surprisingly, some of the novel compounds, in particular those referred to above as preferred, have a particularly valuable aromatic fragrance note, cf. in this regard the examples below.

The present invention therefore also relates to the use of the corresponding compounds (2), (8), (9), (10), (18) and (42) as a fragrance material having an aromatic note.

Surprisingly, some of the novel compounds, in particular those referred to above as preferred, have a particularly valuable leather fragrance note, cf. in this regard the examples below.

The present invention therefore also relates to the use of the corresponding compounds (13), (23), (29), (30), (43) and (44) as a fragrance material having a leather note.

Surprisingly, some of the novel compounds, in particular those referred to above as preferred, have a particularly valuable tobacco fragrance note, cf. in this regard the examples below.

The present invention therefore also relates to the use of the corresponding compounds (9), (15), (23), (24), (29), (30), (40), (41), (43) and (44) as a fragrance material having a tobacco note.

Surprisingly, some of the novel compounds, in particular those referred to above as preferred, have a particularly valuable green fragrance note, cf. in this regard the examples below.

The present invention therefore also relates to the use of the corresponding compounds (1), (12), (13), (31), (34), (43) and (45) as a fragrance material having a green note.

Surprisingly, some of the novel compounds, in particular those referred to above as preferred, have a particularly valuable aniseed fragrance note, cf. in this regard the examples below.

The present invention therefore also relates to the use of the corresponding compounds (9), (45), (51), (52), (57), (60) and (61) as a fragrance material having an aniseed note.

Surprisingly, some of the compounds of Formula (I), in particular the novel compounds of Formula (I) referred to above as preferred, have a particularly valuable flavor note, in particular a flavor note selected from the group consisting of herb, spearmint, cooling, woody, fresh and sharp, cf. in this regard the examples below.

The present invention therefore also relates to the use of the compounds of Formula (I) to be used according to the invention as a flavor material, preferably the compounds of Formula (I) to be used according to the invention, referred to above as preferred, and/or the novel compounds of Formula (I) according to the invention, preferably as a flavor material having a flavor note selected from the group consisting of herb, spearmint, cooling, woody, fresh and sharp.

Surprisingly, some of the compounds of Formula (I), in particular the novel compounds of Formula (I) referred to above as preferred, have a particularly valuable herb flavor note, cf. in this regard the examples below.

The present invention therefore also relates to the use of the corresponding compounds (2), (4) and (43) as a flavor material having an herb note.

Surprisingly, some of the compounds of Formula (I), in particular the novel compounds of Formula (I) referred to above as preferred, have a particularly valuable spearmint flavor note, cf. in this regard the examples below.

The present invention therefore also relates to the use of the corresponding compounds (2), (29) and (10) as a flavor material having a spearmint note.

Surprisingly, some of the compounds of Formula (I), in particular the novel compounds of Formula (I) referred to above as preferred, have a particularly valuable cooling flavor note, cf. in this regard the examples below.

The present invention therefore also relates to the use of the corresponding compounds (2) and (23) as a flavor material having a cooling note.

Surprisingly, some of the compounds of Formula (I), in particular the novel compounds of Formula (I) referred to above as preferred, have a particularly valuable woody flavor note, cf. in this regard the examples below.

The present invention therefore also relates to the use of the corresponding compounds (4), (13), (23) and (43) as a flavor material having a woody note.

Surprisingly, some of the compounds of Formula (I), in particular the novel compounds of Formula (I) referred to above as preferred, have a particularly valuable fresh flavor note, cf. in this regard the examples below.

The present invention therefore also relates to the use of the corresponding compounds (13), (29), (43), (15), (10), (18) and (28) as a flavor material having a fresh note.

Particularly preferred is the combined, i.e. simultaneous use of the compounds to be used according to the invention for the superadditive enhancement of an olfactory impression (preferably for the superadditive enhancement of a floral and/or fruity olfactory impression) and as a flavor material (preferably as a flavor material having a note selected from the group consisting of herb, spearmint, cooling, woody, fresh and sharp). For preferred compounds to be used according to the invention, the comments above apply correspondingly.

More particularly preferred is the combined, i.e. simultaneous use of compounds (1), (2), (3), (4), (5), (8), (9), (10), (12), (13), (14), (15), (18), (19), (23), (24), (28), (29), (30), (31), (32), (33), (34), (37), (40), (41), (42), (43), (44), (45), (48), (51), (52), (57), (60) and (61) for the superadditive enhancement of an olfactory impression (preferably for the superadditive enhancement of a floral and/or fruity olfactory impression) and as a fragrance material having one, two, three, four, five or all fragrance notes selected from the group consisting of spicy, saffron, coumarin, aromatic, leather and tobacco and as a flavor material (preferably as a flavor material having a fresh and/or sharp note).

Also preferred is the combined, i.e. simultaneous use of compounds (1), (2), (3), (4), (5), (8), (9), (10), (12), (13), (14), (15), (18), (19), (23), (24), (28), (29), (30), (31), (32), (33), (34), (37), (40), (41), (42), (43), (44), (45), (48), (51), (52), (57), (60) and (61) as a fragrance material having one, two, three, four, five or all fragrance notes selected from the group consisting of spicy, saffron, coumarin, aromatic, leather and tobacco and as a flavor material (preferably as a flavor material having a fresh and/or sharp note).

Particularly preferred is the use of the compounds of Formula (I) to be used according to the invention, preferably the compounds of Formula (I) to be used which are referred to above as preferred, and/or the novel compounds of Formula (I) according to the invention, as a flavor material, the flavor note not being a meat, roasted grain, chocolate, cocoa, coffee, nutty, sulphurous, earthy and/or fatty flavor.

Another aspect of the present invention relates to fragrance and/or flavor material compositions comprising or consisting of (a) a compound of Formula (I) or a mixture of two, three, four, five, six or a plurality of different compounds of Formula (I), as respectively defined above, preferably as respectively defined above for the compounds or mixtures according to the invention, and (b) one, two, three or a plurality of further fragrance and/or flavor materials, the further fragrance and/or flavor material or the further fragrance and/or flavor materials not being compounds of Formula (I).

As already described above for the use according to the invention of a compound of Formula (I) or a mixture of the compounds of Formula (I), the compounds or the mixtures are suitable in particular as odor enhancers for the superadditive enhancement of a floral and/or fruity olfactory impression. Accordingly, in the fragrance and/or flavor material compositions according to the invention, the or one, two, three, a plurality of or all the further fragrance and/or flavor materials according to constituent (b) have a floral and/or fruity odor.

In the resulting fragrance and/or flavor material compositions, some olfactory impressions are often not advantageous. Correspondingly, a fragrance and/or flavor material composition according to the invention is particularly preferred wherein the olfactory impression which is to be enhanced of the further fragrance and/or flavor materials according to constituent (b) is not selected from the group consisting of nutty, hazelnut, pistachio, cocoa, caramel, meat, roasted grain, chocolate and spicy, and/or wherein the compound of Formula (I) or the corresponding mixture does not impart an olfactory impression which is selected from the group consisting of nutty, hazelnut, pistachio, cocoa, caramel, meat, roasted grain, chocolate and spicy.

This applies correspondingly for mixtures according to the invention which, as configured in many configurations, also comprise further constituents in addition to compounds of Formula (I).

In studies by us, it was found that fragrance and/or flavor material compositions according to the invention, in which constituent (b) does not contain fragrance and/or flavor materials which have a pyrazine basic structure, are preferred in particular.

According to another preferred aspect of the present invention, fragrance and/or flavor material compositions according to the invention, in which constituent (a) enhances one or a plurality of olfactory impressions of constituent (b), a floral and/or fruity olfactory impression of constituent (b) preferably being enhanced, are particularly preferred. Such a composition is also referred to as an "odor-enhanced composition"; cf. in this regard Examples 37 through 86.

For a fragrance and/or flavor material composition according to the invention (as described above, preferably as described as particularly preferred above), according to a preferred configuration the total amount of compounds of Formula (I) is in the range of from 0.0001 through 90 wt. %, preferably in the range of from 0.01 through 70 wt. %, preferably in the range of from 0.1 through 50 wt. %, particularly preferably in the range of from 0.1 through 30 wt. %, more particularly preferably in the range of from 0.1 through 10 wt. %, based on the total weight of the fragrance and/or flavor material composition. A fragrance and/or flavor material composition according to the invention, which contains compounds of Formula (I) in a total amount of from more than 50 through to at most 90 wt. %, is also referred to as an odor enhancer concentrate and is preferred as such. A fragrance and/or flavor material composition according to the invention, which contains compounds of Formula (I) in a total amount of from 0.0001 through 50 wt. %, is conventionally a composition in which the total amount of compounds of Formula (I) is sufficient to superadditively enhance the olfactory impression of one or a plurality of fragrance materials of component (b), which are not compounds of Formula (I). Such a composition is a preferred "odor-enhanced composition"; cf. in this regard again Examples 37 through 86.

Depending on the desired application, it may be advantageous and accordingly preferred according to the invention to select the total amount of constituent (a) in such a way that the respectively resulting fragrance and/or flavor material composition has no intrinsic odor and/or intrinsic flavor of constituent (a) but an olfactory impression, preferably a floral and/or fruity olfactory impression, of at least one, two, three, four, five, six or a plurality of the components of constituent (b) is enhanced.

Fragrance and/or flavor material compositions according to the invention may be used in liquid form, undiluted or diluted with a solvent for perfuming or aromatizing. If the fragrance and/or flavor material compositions according to the invention are diluted with one or a plurality of solvents, the one or the plurality of solvents is/are selected from the group consisting of: ethanol, isopropanol, diethylene glycol monoethyl ether, glycerin, propylene glycol, 1,2-butylene glycol, dipropylene glycol, diethyl phthalate, triethyl citrate, isopropyl myristate, triacetin and plant oil.

In individual cases, it is furthermore preferred to provide one or a plurality of solvents in the fragrance and/or flavor material compositions according to the invention. These solvents are then preferably selected in such a way that they are physiologically harmless in the concentration existing in the individual case. Owing to their considerable toxicity, the use of individual or a plurality of the following solvents in a fragrance and/or flavor material composition according to the invention is not preferred: hexane, toluene, benzene, tetrahydrofuran, pentane, dimethylformamide, diisopropyl ether, dichlormethane, dichlorethane, chloroform, carbon tetrachloride, n-methylpyrrolidone, pyridine, dimethylacetamide, dimethoxyethane, dioxane, diethyl ether and methanol.

In the scope of this invention, compounds of Formula (I) (as described above) are not regarded as solvents.

It has been found that there are further positive properties of the fragrance and/or flavor material compositions according to the invention if the fragrance and/or flavor material compositions according to the invention comprise corresponding further additives. Suitable additives are for example: preservatives, abrasives, anti-acne agents, agents against skin ageing, antibacterial agents, anti-cellulitis agents, antidandruff agents, inflammation inhibiting agents, irritation preventing agents, irritation inhibiting agents, antimicrobial agents, antioxidants, astringents, sweat inhibiting agents, antiseptic agents, antistatics, binders, buffers, carrier materials, chelating agents, cell stimulants, cleaning agents, care agents, depilatory agents, surface-active substances, deodorizing agents, antiperspirants, softeners, emulsifiers, enzymes, essential oils, fibers, film forming agents, fixatives, foam forming agents, foam stabilizers, substances to prevent foaming, foam boosters, fungicides, gelling agents, gel forming agents, hair care agents, hair styling agents, hair smoothing agents, hydrating agents, wetting substances, humectants, bleaching agents, strengthening agents, stain removing agents, optically brightening agents, impregnating agents, dirt repellent agents, friction reducing agents, lubricants, moisturizing creams, ointments, turbidity agents, plasticizers, opacifying agents, polish, gloss agents, polymers, powders, proteins, lipid replenishing agents, polishing agents, silicones, skin balancing agents, skin cleansing agents, skin care agents, skin therapy agents, skin brightening agents, skin protecting agents, skin softening agents, cooling agents, skin cooling agents, warming agents, skin warming agents, stabilizers, UV absorbers, UV filters, detergents, softening rinses, suspending agents, skin tanning agents, thickeners, vitamins, oils, waxes, fats, phospholipids, saturated fatty acids, mono or poly unsaturated fatty acids, alpha-hydroxy acids, polyhydroxy fatty acids, liquefiers, dyes, color protecting agents, pigments, anticorrosives, aromas, flavor materials, fragrance materials, polyols, surfactants, electrolytes, organic solvents or silicone derivatives. The combination of fragrance and/or flavor material compositions according to the invention and additives represents an exemplary article according to the invention.

Furthermore, fragrance and/or flavor material compositions according to the invention may be adsorbed onto a carrier material which ensures both fine distribution of the fragrance or flavor materials in the product and controlled release during use. Such carriers may be porous organic materials such as light sulfate, silica gels, zeolites, gypsum, clays, clay granulates, gas concrete etc. or organic materials such as woods, cellulose-based materials, sugars, dextrins (for example maltodextrin) or plastics such as PVC, polyvinyl acetates or polyurethanes. The combination of a composition according to the invention and a carrier material represents an exemplary article according to the invention.

Fragrance and/or flavor material compositions may in particular also be microencapsulated, spray dried, present as inclusion complexes or extrusion products (i.e. articles according to the invention) and in this form, for example, added to an article to be perfumed or aromatized.

Optionally, the properties of the compositions modified in this way may be optimized further by so-called "coating" with suitable materials with a view to more controlled fragrance release, to which end wax-like plastics, for example polyvinyl alcohol, are preferably used. The resulting products also represent articles according to the invention.

The microencapsulation of the fragrance and/or flavor material compositions according to the invention may, for example, be carried out by the so-called coacervation method with the aid of capsule materials, for example consisting of polyurethane-like materials or soft gelatine. The spray-dried fragrance and/or flavor material compositions according to the invention may, for example, be produced by spray drying an emulsion or dispersion containing the fragrance and/or flavor material composition according to the invention, modified starches, proteins, dextrin and plant gums being used as carrier materials. Inclusion complexes may, for example, be produced by introducing dispersions of the fragrance and/or flavor material composition and cyclodextrins or urea derivatives into a suitable solvent, for example water. Extrusion products may be obtained by melting the fragrance and/or flavor material compositions with a suitable wax-like material and by extrusion with subsequent solidification, optionally in a suitable solvent, for example isopropanol.

The fragrance and/or flavor material compositions according to the invention may be used in concentrated form, in solutions or in modified form as described above for the production of perfumed and/or aromatized articles according to the invention, for example perfume extracts, eau de parfum, eau de toilette, aftershave, eau de cologne, preshave products, splash colognes and perfumed freshening wipes, and the perfuming of acidic, alkaline and neutral cleaning formulations, for example floor cleaners, window cleaners, dishwashing formulations, bath and sanitary cleaners, scouring milk, solid and liquid WC cleaners, pulverant and foam carpet cleaners, fabric fresheners, ironing aids, liquid detergents, pulverant detergents, laundry pretreatment formulations such as bleaches, soaking formulations and stain removers, fabric softeners, washing soaps, washing tablets, disinfectants, surface disinfectants, and of air fresheners in liquid or gel form or deposited on a solid carrier, aerosol sprays, waxes and polishes, such as furniture polishes, floor waxes, shoe creams, and body care formulations, for example solid and liquid soaps, shower gels, shampoos, shaving soaps, shaving foams, bath oils, cosmetic emulsions of the oil-in-water, water-in-oil and water-in-oil-in-water type, for example skin creams and lotions, face creams and lotions, sunscreen creams and lotions, after sun creams and lotions, hand creams and lotions, foot creams and lotions, depilatory creams and lotions, aftershave creams and lotions, tanning creams and lotions, hair care products, for example hair sprays, hair gels, hair setting lotions, hair rinses, permanent and semipermanent hair colorants, hair styling formulations, such as cold waves and hair smoothing formulations, hair tonics, hair creams and lotions, deodorants and antiperspirants, for example underarm sprays, roll-ons, deodorant sticks, deodorant creams, products for decorative cosmetics, for example eye shadows, nail varnishes, make-up, lipsticks, mascara, as well as candles, lamp oils, joss-sticks, insecticides, repellents and propellants.

The fragrance and/or flavor material composition according to the invention may be incorporated into aromatized products or products to be aromatized, in particular preparations used for foodstuff, oral hygiene or semi luxury food. Such products generally comprise constituents (for example colorants) which have functions other than those relating to the development of aroma or fragrance and/or an already tradable product (for example perfume oil).

Preparations used for foodstuff or semi luxury food are, for example, bakery products (for example bread, dry biscuits, cakes, other pastries), confectionery (for example chocolate, chocolate bar products, other products in bar form, fruit gums, hard and soft caramels, chewing gum), alcoholic and non-alcoholic beverages (for example coffee, tea, wine, beverages containing wine, beer, beverages containing beer, liqueurs, schnapps, brandies, sodas containing fruit, isotonic drinks, soft drinks, nectars, fruit and vegetable juices, fruit or vegetable juice preparations), instant beverages (for example instant cocoa beverages, instant tea beverages, instant coffee beverages), meat products (for example ham, fresh or raw sausage preparations, seasoned or marinated fresh or salt meat products), eggs or egg products (for example dried egg, egg white, egg yolk), cereal products (for example breakfast cereals, muesli bars, pre-cooked finished rice products), milk products (for example milk beverages, ice milk, yogurt, kefir, cream cheese, soft cheese, hard cheese, powdered milk, whey, butter, buttermilk, partially or fully hydrolyzed milk protein-containing products), products from soya protein or other soybean fractions (for example soya milk and products produced therefrom, soya lecithin-containing preparations, fermented products such as tofu or tempeh or products produced therefrom, soy sauces), fruit preparations (for example jams, sorbets, fruit sauces, fruit fillings), vegetable preparations (for example ketchup, sauces, dried vegetables, deep-frozen vegetables, precooked vegetables, vegetables in vinegar, preserved vegetables), snack foods (for example baked or fried potato chips or potato dough products, bread dough products, corn or peanut-based extrudates), fat and oil-based products or the emulsions thereof (for example mayonnaise, remoulade, dressings, seasoning preparations), other ready meals and soups (for example powdered soups, instant soups, precooked soups), spices, seasoning mixtures and in particular seasonings which are used, for example, in the snacks sector. After incorporation of the a) compound of Formula (I) according to the invention, or the mixtures thereof, and/or b) the fragrance and/or flavor material composition according to the invention, these preparations are articles according to the invention.

Preparations may, for example, be in the form of semi finished products or a seasoning mixture.

Preparations may, in particular, be used as semi finished products for the production of further preparations used for foodstuff or semi luxury food, in particular in spray-dried form.

Preparations may also be in the form of capsules, tablets (uncoated as well as coated tablets, for example gastric juice-resistant coatings), sugar-coated pills, granules, pellets, solid mixtures, dispersions in the liquid phase, as emulsions, powders, solutions, pastes or as other preparations which can be swallowed or chewed as food supplements.

The preparations used for oral hygiene are, in particular, oral and/or dental hygiene formulations, such as toothpastes, tooth gels, tooth powders, mouth washes, chewing gums and other oral formulations.

Other conventional active substances, bases, excipients and additives for preparations according to the invention used for foodstuffs, dental hygiene and semi luxury food may be contained in amounts of from 5 through 99.999999 wt. %, preferably from 10 through 80 wt. %, expressed in terms of the total weight of the preparation. The preparations may furthermore comprise water in an amount of up to 99.999999 wt. %, preferably from 5 through 80 wt. %, expressed in terms of the total weight of the preparation.

According to a preferred configuration, the preparations (as examples of articles according to the invention), containing a) the compound of Formula (I) according to the invention, or the mixture thereof, and/or b) the fragrance and/or flavor material composition according to the invention, are prepared by incorporating the compound according to the invention, or the mixtures thereof, and/or the fragrance and/or flavor material composition according to the invention as a material, as a solution (for example in ethanol, water or 1,2-propylene glycol) or in the form of a mixture with a solid or liquid carrier material (for example maltodextrin, starch, silica gel), other aromas or flavor materials and optionally further auxiliaries and/or stabilizers (for example natural or artificial polysaccharides and/or plant gums such as modified starches or gum arabic) into a base preparation used for foodstuff, oral hygiene or semi luxury food. Advantageously, preparations existing as a solution and/or suspension or emulsion may also be converted into a solid preparation (semi finished product) by spray drying.

The spray-dried solid preparations (as an example of articles according to the invention) are, as semi finished products, particularly highly suitable for the production of further preparations. The spray-dried solid preparations preferably contain from 50 through 95 wt. % of carrier materials, in particular maltodextrin and/or starch, from 5 through 40 wt. % of excipients, preferably natural or synthetic polysaccharides and/or plant gums such as modified starches or gum arabic.

According to another preferred embodiment, in order to produce preparations, a) the compound of Formula (I) according to the invention, or the mixture thereof, and/or b) the fragrance and/or flavor material composition according to the invention and optionally other constituents of the preparation according to the invention are first incorporated into emulsions, liposomes, for example based on phosphatidylcholine, microspheres, nanospheres or capsules, granules or extrudates from a matrix suitable for foodstuff and semi luxury food, for example consisting of starch, starch derivatives (for example modified starch), cellulose or cellulose derivatives (for example hydroxypropyl cellulose), other polysaccharides (for example dextrin, alginate, curdlan, carageenan, chitin, chitosan, pullulan), natural fats, natural waxes (for example beeswax, carnauba wax), from proteins, for example gelatine or other natural products (for example shellac). In this case, depending on the matrix, the products may be obtained by spray drying, spray granulation, melt granulation, coacervation, coagulation, extrusion, melt extrusion, emulsion methods, coating or other suitable encapsulation methods and optionally a suitable combination of the aforementioned methods. In another preferred production method for a preparation according to the invention, the compound according to the invention is first complexed with one or a plurality of suitable complexing agents, for example with cyclodextrins or cyclodextrin derivatives, preferably alpha or beta cyclodextrin, and used in this complexed form.

A preparation, in which the matrix is selected in such a way that the compound according to the invention is released from the matrix with a delay, so that a long-lasting effect is achieved, is particularly preferred. To this extent, a fat, wax, polysaccharide or protein matrix is particularly preferred.

As further constituents of the preparations used for the foodstuff or semi luxury food, it is possible to use bases, excipients and additives which are conventional for foodstuffs or semi luxury foods, for example water, mixtures of fresh or processed, plant or animal bases or raw materials (for example raw, baked, dried, fermented, smoked and/or cooked meat, bones, cartilage, fish, vegetables, fruit, herbs, nuts, vegetable or fruit juices or pastes or the mixtures thereof), digestible or indigestible carbohydrates (for example saccharose, maltose, fructose, glucose, dextrins, amylose, amylopectin, inulin, xylane, cellulose, tagatose), sugar alcohols (for example sorbitol, erythritol), natural or hydrogenated fats (for example tallow, lard, palm fat, cocoa fat, hydrogenated plant fat), oils (for example sunflower oil, groundnut oil, corn seed oil, olive oil, fish oil, soya oil, sesame oil), fatty acids or the salts thereof (for example potassium stearate), proteinogenic or non-proteinogenic amino acids and related compounds (for example gamma-aminobutyric acid, taurine), peptides (for example glutathione), native or processed proteins (for example gelatine), enzymes (for example peptidases), nucleic acids, nucleotides, flavor correctors for unpleasant flavor impressions, further flavor modulators for other generally not unpleasant flavor impressions, other flavor modulating substances (for example inositol phosphate, nucleotides such as guanosine monophosphate, adenosine monophosphate or other substances such as sodium glutamate or 2-phenoxypropionic acid), emulsifiers (for example lecithins, diacylglycerols, gum arabic), stabilizers (for example carrageenan, alginate), preservatives (for example benzoic acid, sorbic acid), antioxidants (for example tocopherol, ascorbic acid), chelators (for example citric acid), organic or inorganic acidifiers (for example malic acid, acetic acid, citric acid, tartaric acid, phosphoric acid), bitters (for example quinine, caffeine, limonin, amarogentin, humolone, lupolone, catechine, tannins), mineral salts (for example sodium chloride, potassium chloride, manganese chloride, sodium phosphates), substances preventing enzymatic browning (for example sulfite, ascorbic acid), essential oils, plant extracts, natural or synthetic dyes or pigments (for example carotinoids, flavonoids, anthocyans, chlorophyll and the derivatives thereof), spices, trigeminally active substances or plant extracts containing such trigeminally active substances, synthetic, natural or naturally identical flavor materials or fragrance materials and odor correctors.

Dental hygiene formulations (as a basis of preparations used for oral hygiene), which contain a) the compound of Formula (I) according to the invention, or the mixture thereof, and/or b) the fragrance and/or flavor material composition according to the invention, generally comprise an abrasive system (grinding or polishing agent), such as silicic acid, calcium carbonates, calcium phosphates, aluminum oxides and/or hydroxyapatites, surface-active substances, for example sodium lauryl sulfate, sodium lauryl sarcosinate and/or cocamidopropyl betaine, humectants, for example glycerin and/or sorbitol, thickeners, for example carboxymethyl cellulose, polyethylene glycols, carrageenan and/or Laponite®, sweeteners, for example saccharin, flavor correctors for unpleasant flavor impressions, flavor correctors for further generally not unpleasant flavor impressions, flavor modulating substances (for example inositol phosphate, nucleotides such as guanosine monophosphate, adenosine monophosphate or other substances such as sodium glutamate or 2-phenoxypropionic acid), cooling active ingredients, for example menthol, menthol derivatives (for example L-menthol, L-menthyl acetate, L-menthyl alkyl carbonates, menthone ketals, menthane carboxylic acid amides), 2,2,2-trialkylacetamides (for example 2,2-diisopropylpropionic acid methylamide), icilin and icilin derivatives, stabilizers and active ingredients, such as for example sodium fluoride, sodium monofluorophosphate, tin difluoride, quaternary ammonium fluorides, zinc citrate, zinc sulfate, tin pyrophosphate, tin dichloride, mixtures of different pyrophosphates, triclosan, cetylpyridinium chloride, aluminum lactate, potassium citrate, potassium nitrate, potassium chloride, strontium chloride, hydrogen peroxide, aromas and/or sodium bicarbonate or odor correctors.

Chewing gums (as another example of preparations used for oral hygiene), which contain a) the compound of Formula (I) according to the invention, or the mixture thereof, and/or b) the fragrance and/or flavor material composition according to the invention, generally comprise a chewing gum base, i.e. a chewing compound which becomes plastic when chewed, various types of sugar, sugar substitutes, other sweet-tasting substances, sugar alcohols, flavor correctors for unpleasant flavor impressions, other modulators for other generally not unpleasant flavor impressions, flavor modulating substances (for example inositol phosphate, nucleotides such as guanosine monophosphate, adenosine monophosphate or other substances such as sodium glutamate or 2-phenoxypropionic acid), humectants, thickeners, emulsifiers, aromas and stabilizers or other odor correctors.

Preferably, besides the compound to be used according to the invention, the preparations may contain an (additional) aroma composition in order to round the flavor and/or odor of the preparation. Suitable (additional) aroma compositions contain, for example, synthetic, natural or naturally identical aroma, fragrance and flavor as well as suitable excipients and carrier materials.

After incorporation of a) the compound of Formula (I) according to the invention, or the mixture thereof, and/or b) the fragrance and/or flavor material composition according to the invention, these preparations are articles according to the invention as defined below.

The compound of Formula (I) to be used according to the invention, or corresponding mixtures thereof, or a fragrance and/or flavor material composition according to the invention (as described above) may advantageously also be used for perfuming and/or aromatizing certain articles, or may be a constituent of such articles. In particular, a fragrance and/or flavor material composition according to the invention, preferably a fragrance and/or flavor material composition according to the invention as described herein as preferred, may be used in the scope of the present invention as a constituent of a perfumed and/or aromatized article.

Correspondingly, the present invention also relates to a perfumed and/or aromatized article which comprises a fragrance and/or flavor material composition according to the invention (as described herein).

In a preferred configuration, the perfumed and/or aromatized article according to the invention is selected from the group consisting of: perfume extracts, eau de parfum, eau de toilette, aftershave, eau de cologne, preshave products, splash colognes and perfumed freshening wipes, acidic, alkaline and neutral cleaning formulations, fabric fresheners, ironing aids, liquid detergents, pulverant detergents, laundry pretreatment formulations, fabric softeners, washing soaps, washing tablets, disinfectants, surface disinfectants, air fresheners, aerosol sprays, waxes and polishes, bodycare formulations, hand creams and lotions, foot creams and lotions, depilatory creams and lotions, aftershave creams and lotions, tanning creams and lotions, hair care products, deodorants and antiperspirants, products for decorative cosmetics, candles, lamp oils, joss-sticks, insecticides, repellents and propellants.

In many cases, articles according to the invention comprise a carrier or a substrate, which is in direct contact with the compound or compounds of Formula (I) or the fragrance and/or flavor material composition. Such carriers may be porous inorganic materials such as light sulfate, silica gels, zeolites, gypsum, clays, clay granulates, gas concrete etc. or organic materials such as woods, cellulose-based materials, sugars, dextrins (for example maltodextrin) or plastics such as PVC, polyvinyl acetates or polyurethanes.

Another aspect of the present invention relates to a method for the enhancement of an olfactory impression, preferably a floral and/or fruity fragrance, comprising the following step:

bringing in contact or mixing
a compound of Formula (I)
as defined above, in particular as defined above for the novel compounds of Formula (I),
a mixture of two, three, four, five, six or a plurality of different compounds of Formula (I),
as defined above, in particular as defined above for the novel compounds of Formula (I),
or
a fragrance and/or flavor material composition as defined above, with a product.

Preferred products are the preferred articles or preparations, or one, two, three, or a plurality of further fragrance and/or flavor materials according to the invention as described above, the fragrance and/or flavor material or the further fragrance and/or flavor materials not being compounds of Formula (I) and preferably having a floral and/or fruity fragrance.

Preferred materials, which in the scope of the present invention are or may be contained in an article according to the invention, a fragrance and/or flavor material composition according to the invention, preferably as constituent (b) of a fragrance and/or flavor material composition, may for example be found in S. Arctander, Perfume and Flavor Materials, Vol. I and II, Montclair, N.J. 1969, Eigenverlag, or K. Bauer et al., Common Fragrance and Flavor Materials, 4th Edition, Wiley-VCH, Weinheim 2001.

The following may be mentioned in detail:

Extracts of natural raw materials such as essential oils, concretes, absolutes, resins, resinoids, balsams, tinctures, for example Ambergris tincture; amyris oil; angelica seed oil; angelica root oil; anise oil; valerian oil; basil oil; tree moss absolute; bay oil; mugwort oil; benzoin resin; bergamot oil; beeswax absolute; birch tar oil; bitter almond oil; savory oil; buchu leaf oil; cabreuva oil; cade oil; calamus oil; camphor oil; cananga oil; cardamom oil; cascarilla oil; cassia oil; cassie absolute; castoreum absolute; cedar leaf oil; cedar wood oil; cistus oil; citronella oil; lemon oil; copaiba balsam; copaiba balsam oil; coriander oil; costus root oil; cumin oil; cypress oil; davana oil; dill oil; dill seed oil; eau de brouts absolute; oak moss absolute; elemi oil; tarragon oil; eucalyptus citriodora oil; eucalyptus oil; fennel oil; fir-needle oil; galbanum oil; galbanum resin; geranium oil; grapefruit oil; guaiacwood oil; gurjun balsam; gurjun balsam oil, helichrysum absolute; helichrysum oil; ginger oil; iris root absolute; iris root oil; jasmine absolute; calamus oil; chamomile oil blue; Roman chamomile oil; carrot seed oil; cascarilla oil; pine needle oil; spearmint oil; caraway oil; labdanum oil; labdanum absolute; labdanum resin; lavandin absolute; lavandin oil; lavender absolute; lavender oil; lemongrass oil; lovage oil; sweet lime oil distilled; sweet lime oil pressed; linaloe oil; litsea cubeba oil; bay leaf oil; mace oil; marjoram oil; mandarin oil; massoia bark oil; mimosa absolute; musk seed oil; musk tincture; muscatel-sage oil; nutmeg butter; myrrh absolute; myrrh oil; myrtle oil; clove leaf oil; clove blossom oil; neroli oil; olibanum absolute; olibanum oil; opopanax oil; orange blossom absolute; orange oil; origanum oil; palmarosa oil; patchouli oil; perilla oil; Peruvian balsam oil; parsley leaf oil; parsley seed oil; petitgrain oil; peppermint oil; pepper oil; pimenta oil; pine oil; poley oil; rose absolute; rosewood oil; rose oil; rosemary oil; Dalmatian sage oil; Spanish sage oil; sandalwood oil; celery seed oil; spike lavender oil; star anise oil; styrax oil; tagetes oil; fir-needle oil; tea tree oil; turpentine oil; thyme oil; tolu balsam; tonka absolute; tuberose absolute; vanilla extract; violet leaf absolute; verbena oil; vetiver oil; juniper berry oil; wine lees oil; wormwood oil; wintergreen oil; ylang-ylang oil; hyssop oil; civet absolute; cinnamon leaf oil; cinnamon bark oil; and the fractions thereof or ingredients isolated therefrom.

Individual fragrance materials from the group of the hydrocarbons, such as for example 3-carene; alpha-pinene; beta-pinene; alpha-terpinene; gamma-terpinene; p-cymene; bisabolene; camphene; caryophyllene; cedrene; farnesene; limonene; longifolene; myrcene; ocimene; valencene; (E,Z)-1,3,5-undecatriene; styrene; diphenylmethane;

of the aliphatic alcohols, such as for example hexanol; octanol; 3-octanol; 2,6-dimethylheptanol; 2-methyl-2-heptanol, 2-methyl-2-octanol; (E)-2-hexenol; (E)- and (Z)-3-hexenol; 1-octen-3-ol; mixture of 3,4,5,6,6-pentamethyl-3/4-hepten-2-ol and 3,5,6,6-tetramethyl-4-methyleneheptan-2-ol; (E,Z)-2,6-nonadienol; 3,7-dimethyl-7-methoxyoctan-2-ol; 9-decenol; 10-undecenol; 4-methyl-3-decen-5-ol;

of the aliphatic aldehydes and the acetals thereof, such as for example hexanal; heptanal; octanal; nonanal; decanal; undecanal; dodecanal; tridecanal; 2-methyloctanal; 2-methylnonanal; (E)-2-hexenal; (Z)-4-heptenal; 2,6-dimethyl-5-heptenal; 10-undecenal; (E)-4-decenal; 2-dodecenal; 2,6,10-trimethyl-9-undecenal; 2,6,10-trimethyl-5,9-undecadienal; heptanal diethylacetal; 1,1-dimethoxy-2,2,5-trimethyl-4-hexene; citronellyl oxyacetaldehyde; 1-(1-methoxypropoxy)-(E/Z)-3-hexene;

of the aliphatic ketones and the oximes thereof, such as for example 2-heptanone; 2-octanone; 3-octanone; 2-nonanone; 5-methyl-3-heptanone; 5-methyl-3-heptanone oxime; 2,4,4,7-tetramethyl-6-octen-3-one; 6-methyl-5-hepten-2-one;

of the aliphatic compounds containing sulfur, such as for example 3-methylthiohexanol; 3-methylthiohexyl acetate; 3-mercaptohexanol; 3-mercaptohexyl acetate; 3-mercaptohexyl butyrate; 3-acetylthiohexyl acetate; 1-menthene-8-thiol;

of the aliphatic nitriles, such as for example 2-nonenoic acid nitrile; 2-undecenoic acid nitrile; 2-tridecenoic acid nitrile; 3,12-tridecadienoic acid nitrile; 3,7-dimethyl-2,6-octadienoic acid nitrile; 3,7-dimethyl-6-octenoic acid nitrile;

of the esters of aliphatic carboxylic acids, such as for example (E)- and (Z)-3-hexenylformate; ethyl acetoacetate; isoamyl acetate; hexyl acetate; 3,5,5-trimethylhexyl acetate; 3-methyl-2-butenyl acetate; (E)-2-hexenyl acetate; (E)- and (Z)-3-hexenyl acetate; octyl acetate; 3-octyl acetate; 1-octen-3-yl acetate; ethyl butyrate; butyl butyrate; isoamyl butyrate; hexyl butyrate; (E)- and (Z)-3-hexenyl isobutyrate; hexyl crotonate; ethyl isovalerate; ethyl-2-methylpentanoate; ethyl hexanoate; allyl hexanoate; ethyl heptanoate; allyl heptanoate; ethyl octanoate; ethyl-(E,Z)-2,4-decadienoate; methyl-2-octinate; methyl-2-noninate; allyl-2-isoamyloxyacetate; methyl-3,7-dimethyl-2,6-octadienoate; 4-methyl-2-pentyl crotonate;

of the acyclic terpene alcohols, such as for example citronellol; geraniol; nerol; linalool; lavadulol; nerolidol; farnesol; tetrahydrolinalool; tetrahydrogeraniol; 2,6-dimethyl-7-octen-2-ol; 2,6-dimethyloctan-2-ol; 2-methyl-6-methylene-7-octen-2-ol; 2,6-dimethyl-5,7-octadien-2-ol; 2,6-dimethyl-3,5-octadien-2-ol; 3,7-dimethyl-4,6-octadien-3-ol; 3,7-dimethyl-1,5,7-octatrien-3-ol; 2,6-dimethyl-2,5,7-octatrien-1-ol; and their formates, acetates, propionates, isobutyrates, butyrates, isovalerates, pentanoates, hexanoates, crotonates, tiglinates and 3-methyl-2-butenoates;

of the acyclic terpene aldehydes and terpene ketones, such as for example geranial; neral; citronellal; 7-hydroxy-3,7-dimethyloctanal; 7-methoxy-3,7-dimethyloctanal; 2,6,10- trimethyl-9-undecenal; geranyl acetone; and the dimethyl and diethyl acetals of geranial, neral, 7-hydroxy-3,7-dimethyloctanal;

of the cyclic terpene alcohols, such as for example menthol; isopulegol; alpha-terpineol; terpinenol-4; menthan-8-ol; menthan-1-ol; menthan-7-ol; borneol; isoborneol; linalool oxide; nopol; cedrol; ambrinol; vetiverol; guaiol; and the formates thereof, acetates, propionates, isobutyrates, butyrates, isovalerates, pentanoates, hexanoates, crotonates, tiglinates and 3-methyl-2-butenoates;

of the cyclic terpene aldehydes and terpene ketones, such as for example menthone; isomenthone; 8-mercaptomenthan-3-one; carvone; camphor; fenchone; alpha-ionone; beta-ionone; alpha-n-methylionone; beta-n-methylionone; alpha-isomethylionone; beta-isomethylionone; alpha-irone; alpha-damascone; beta-damascone; beta-damascenone; delta-damascone; gamma-damascone; 1-(2,4,4-trimethyl-2-cyclohexen-1-yl)-2-buten-1-one; 1,3,4,6,7,8a-hexahydro-1,1,5,5-tetramethyl-2H-2,4-a-methanonaphthalen-8(5H)-one; 2-methyl-4-(2,6,6-trimethyl-1-cyclohexen-1-yl)-2-butenal; nootkatone; dihydronootkatone; 4,6,8-megastigmatrien-3-one; alpha-sinensal; beta-sinensal; acetylated cedar wood oil (methyl cedryl ketone);

of the cyclic alcohols, such as for example 4-tert-butylcyclohexanol; 3,3,5-trimethylcyclohexanol; 3-isocamphylcyclohexanol; 2,6,9-trimethyl-(Z2,Z5,E9)-cyclododecatrien-1-ol; 2-isobutyl-4-methyltetrahydro-2H-pyran-4-ol;

of the cycloaliphatic alcohols, such as for example alpha, 3,3-trimethylcyclohexylmethanol; 1-(4-isopropylcyclohexyl)ethanol; 2-methyl-4-(2,2,3-trimethyl-3-cyclopent-1-yl)butanol; 2-methyl-4-(2,2,3-trimethyl-3-cyclopent-1-yl)-2-buten-1-ol; 2-ethyl-4-(2,2,3-trimethyl-3-cyclopent-1-yl)-2-buten-1-ol; 3-methyl-5-(2,2,3-trimethyl-3-cyclopent-1-yl)-pentan-2-ol; 3-methyl-5-(2,2,3-trimethyl-3-cyclopent-1-yl)-4-penten-2-ol; 3,3-dimethyl-5-(2,2,3-trimethyl-3-cyclopent-1-yl)-4-penten-2-ol; 1-(2,2,6-trimethylcyclohexyl)pentan-3-ol; 1-(2,2,6-trimethylcyclohexyl)hexan-3-ol;

of the cyclic and cycloaliphatic ethers, such as for example cineol; cedryl methyl ether; cyclododecyl methyl ether; 1,1-dimethoxycyclododecane; (ethoxymethoxy)cyclododecane; alpha-cedrene-epoxide; 3a,6,6,9a-tetramethyldodecahydronaphtho[2,1-b]furan; 3a-ethyl-6,6,9a-trimethyldodecahydronaphtho[2,1-b]furan; 1,5,9-trimethyl-13-oxabicyclo[10.1.0]trideca-4,8-diene; rose oxide; 2-(2,4-dimethyl-3-cyclohexen-1-yl)-5-methyl-5-(1-methylpropyl)-1,3-dioxane;

of the cyclic and macrocyclic ketones, such as for example 4-tert-butylcyclohexanone; 2,2,5-trimethyl-5-pentylcyclopentanone; 2-heptylcyclopentanone; 2-pentylcyclopentanone; 2-hydroxy-3-methyl-2-cyclopenten-1-one; 3-methyl-cis-2-penten-1-yl-2-cyclopenten-1-one; 3-methyl-2-pentyl-2-cyclopenten-1-one; 3-methyl-4-cyclopentadecenone; 3-methyl-5-cyclopentadecenone; 3-methylcyclopentadecanone; 4-(1-ethoxyvinyl)-3,3,5,5-tetramethylcyclohexanone; 4-tert-pentylcyclohexanone; 5-cyclohexadecen-1-one; 6,7-dihydro-1,1,2,3,3-pentamethyl-4(5H)-indanone; 8-cyclohexadecen-1-one 9-cycloheptadecen-1-one; cyclopentadecanone; cyclohexadecanone;

of the cycloaliphatic aldehydes, such as for example 2,4-dimethyl-3-cyclohexenecarbaldehyde; 2-methyl-4-(2,2,6-trimethylcyclohexen-1-yl)-2-butenal; 4-(4-hydroxy-4-methylpentyl)-3-cyclohexenecarbaldehyde; 4-(4-methyl-3-penten-1-yl)-3-cyclohexenecarbaldehyde;

of the cycloaliphatic ketones, such as for example 1-(3,3-dimethylcyclohexyl)-4-penten-1-one; 2,2-dimethyl-1-(2,4-dimethyl-3-cyclohexen-1-yl)-1-propanone; 1-(5,5-dimethyl-1-cyclohexen-1-yl)-4-penten-1-one; 2,3,8,8-tetramethyl-1,2,3,4,5,6,7,8-octahydro-2-naphthalenyl methyl ketone; methyl-2,6,10-trimethyl-2,5,9-cyclododecatrienyl ketone; tert-butyl-(2,4-dimethyl-3-cyclohexen-1-yl) ketone;

of the esters of cyclic alcohols, such as for example 2-tert-butylcyclohexyl acetate; 4-tert-butylcyclohexyl acetate; 2-tert-pentylcyclohexyl acetate; 4-tert-pentylcyclohexyl acetate; 3,3,5-trimethylcyclohexyl acetate; decahydro-2-naphthyl acetate; 2-cyclopentylcyclopentyl crotonate; 3-pentyltetrahydro-2H-pyran-4-yl acetate; decahydro-2,5,5,8a-tetramethyl-2-naphthyl acetate; 4,7-methano-3a,4,5,6,7,7a-hexahydro-5- or -6-indenyl acetate; 4,7-methano-3a,4,5,6,7,7a-hexahydro-5- or -6-indenyl propionate; 4,7-methano-3a,4,5,6,7,7a-hexahydro-5- or -6-indenyl isobutyrate; 4,7-methanooctahydro-5- or -6-indenyl acetate;

of the esters of cycloaliphatic alcohols, such as for example 1-cyclohexylethyl crotonate;

of the esters of cycloaliphatic carboxylic acids, such as for example allyl-3-cyclohexylpropionate; allylcyclohexyloxyacetate; cis- and trans-methyl dihydrojasmonate; cis- and trans-methyl jasmonate; methyl-2-hexyl-3-oxocyclopentane carboxylate; ethyl-2-ethyl-6,6-dimethyl-2-cyclohexenecarboxylate; ethyl-2,3,6,6-tetramethyl-2-cyclohexenecarboxylate; ethyl-2-methyl-1,3-dioxolan-2-acetate;

of the araliphatic alcohols, such as for example benzyl alcohol; 1-phenylethyl alcohol; 2-phenylethyl alcohol; 3-phenylpropanol; 2-phenylpropanol; 2-phenoxyethanol; 2,2-dimethyl-3-phenylpropanol; 2,2-dimethyl-3-(3-methylphenyl)propanol; 1,1-dimethyl-2-phenylethyl alcohol; 1,1-dimethyl-3-phenylpropanol; 1-ethyl-1-methyl-3-phenylpropanol; 2-methyl-5-phenylpentanol; 3-methyl-5-phenylpentanol; 3-phenyl-2-propen-1-ol; 4-methoxybenzyl alcohol; 1-(4-isopropylphenyl)ethanol;

of the esters of araliphatic alcohols and aliphatic carboxylic acids, such as for example benzyl acetate; benzyl propionate; benzyl isobutyrate; benzyl isovalerate; 2-phenylethyl acetate; 2-phenylethylpropionate; 2-phenylethyl isobutyrate; 2-phenylethyl isovalerate; 1-phenylethyl acetate; alpha-trichloromethylbenzyl acetate; alpha,alpha-dimethyl phenyl ethyl acetate; alpha,alpha-dimethyl phenyl ethyl butyrate; cinnamyl acetate; 2-phenoxyethyl isobutyrate; 4-methoxybenzyl acetate;

of the araliphatic ethers, such as for example 2-phenylethylmethyl ether; 2-phenylethyl isoamyl ether; 2-phenylethyl-1-ethoxyethyl ether; phenylacetaldehyde dimethyl acetal; phenylacetaldehydediethyl acetal; hydratropic aldehyde dimethyl acetal; phenylacetaldehyde glycerin acetal; 2,4,6-trimethyl-4-phenyl-1,3-dioxanes; 4,4a,5,9b-tetrahydroindeno[1,2-d]-m-dioxin; 4,4a,5,9b-tetrahydro-2,4-dimethylindeno[1,2-d]-m-dioxin;

of the aromatic and araliphatic aldehydes, such as for example benzaldehyde; phenylacetaldehyde; 3-phenylpropanal; hydratropic aldehyde; 4-methylbenzaldehyde; 4-methylphenylacetaldehyde; 3-(4-ethylphenyl)-2,2-dimethylpropanal; 2-methyl-3-(4-isopropylphenyl)propanal; 2-methyl-3-(4-tert-butylphenyl)propanal; 2-methyl-3-(4-tert.-butylphenyl)propanal; 3-(4-tert-butylphenyl)propanal; cinnamaldehyde; alpha-butyl cinnamaldehyde; alpha-amyl cinnamaldehyde; alpha-hexyl cinnamaldehyde; 3-methyl-5-phenylpentanal; 4-methoxybenzaldehyde; 4-hydroxy-3-methoxybenzaldehyde; 4-hydroxy-3-ethoxybenzaldehyde; 3,4-methylene dioxybenzaldehyde; 3,4-dimethoxybenzaldehyde; 2-methyl-3-(4-methoxyphenyl)propanal; 2-methyl-3-(4-methylene dioxyphenyl)propanal;

of the aromatic and araliphatic ketones, such as for example acetophenone; 4-methylacetophenone; 4-methoxyacetophenone; 4-tert-butyl-2,6-dimethylacetophenone; 4-phenyl-2-butanone; 4-(4-hydroxyphenyl)-2-butanone; 1-(2-naphthalenyl)ethanone; 2-benzofuranylethanone; (3-methyl-2-benzofuranyl)ethanone; benzophenone; 1,1,2,3,3,6-hexamethyl-5-indanylmethyl ketone; 6-tert-butyl-1,1-dimethyl-4-indanylmethyl ketone; 1-[2,3-dihydro-1,1,2,6-tetramethyl-3-(1-methylethyl)-1H-5-indenyl]ethanone; 5',6',7',8'-tetrahydro-3',5',5',6',8',8'-hexamethyl-2-acetonaphthone;

of the aromatic and araliphatic carboxylic acids and the esters thereof, such for example benzoic acid; phenylacetic acid; methyl benzoate; ethyl benzoate; hexyl benzoate; benzyl benzoate; methylphenyl acetate; ethyl phenyl acetate; geranyl phenyl acetate; phenyl ethyl phenyl acetate; methyl cinnamate; ethyl cinnamate; benzyl cinnamate; phenyl ethyl cinnamate; cinnamyl cinnamate; allylphenoxy acetate; methyl salicylate; isoamyl salicylate; hexyl salicylate; cyclohexyl salicylate; cis-3-hexenyl salicylate; benzyl salicylate; phenyl ethyl salicylate; methyl-2,4-dihydroxy-3,6-dimethyl benzoate; ethyl-3-phenyl glycidate; ethyl-3-methyl-3-phenyl glycidate;

of the aromatic compounds containing nitrogen, such as for example, 2,4,6-trinitro-1,3-dimethyl-5-tert-butylbenzene; 3,5-dinitro-2,6-dimethyl-4-tert-butylacetophenone; cinnamic acid nitrile; 5-phenyl-3-methyl-2-pentenoic acid nitrile; 5-phenyl-3-methylpentanoic acid nitrile; methyl anthranilate; methyl-N-methyl anthranilate; Schiff's bases of methyl anthranilate with 7-hydroxy-3,7-dimethyloctanal, 2-methyl-3-(4-tert-butylphenyl)propanal or 2,4-dimethyl-3-cyclohexenecarbaldehyde; 6-isopropylquinoline; 6-isobutylquinoline; 6-sec-butylquinoline; 2-(3-phenylpropyl)pyridine; indole; skatole;

of the phenols, phenyl ethers and phenyl esters, such as for example estragole; anethole; eugenol; eugenyl methyl ether; isoeugenol; isoeugenyl methyl ether; thymol; carvacrol; diphenyl ether; beta-naphthyl methyl ether; beta-naphthyl ethyl ether; beta-naphthyl isobutyl ether; 1,4-dimethoxybenzene; eugenyl acetate; 2-methoxy-4-methylphenol; 2-ethoxy-5-(1-propenyl)phenol; p-cresyl phenyl acetate;

of the heterocyclic compounds, such as for example 2,5-dimethyl-4-hydroxy-2H-furan-3-one; 2-ethyl-4-hydroxy-5-methyl-2H-furan-3-one; 3-hydroxy-2-methyl-4H-pyran-4-one; 2-ethyl-3-hydroxy-4H-pyran-4-one;

of the lactones, such as for example 1,4-octanolide; 3-methyl-1,4-octanolide; 1,4-nonanolide; 1,4-decanolide; 8-decen-1,4-olide; 1,4-undecanolide; 1,4-dodecanolide; 1,5-decanolide; 1,5-dodecanolide; 4-methyl-1,4-decanolide; 1,15-pentadecanolide; cis- and trans-11-pentadecen-1,15-olide; cis- and trans-12-pentadecen-1,15-olide; 1,16-hexadecanolide; 9-hexadecen-1,16-olide; 10-oxa-1,16-hexadecanolide; 11-oxa-1,16-hexadecanolide; 12-oxa-1,16-hexadecanolide; ethylene-1,12-dodecanedioate; ethylene-1,13-tridecanedioate; coumarin; 2,3-dihydrocoumarin; octahydrocoumarin.

As will be explained in more detail below (cf. synthesis route according to Scheme 1 and Example 1), the compound of Formula (I) can be synthesized in a particularly economical way.

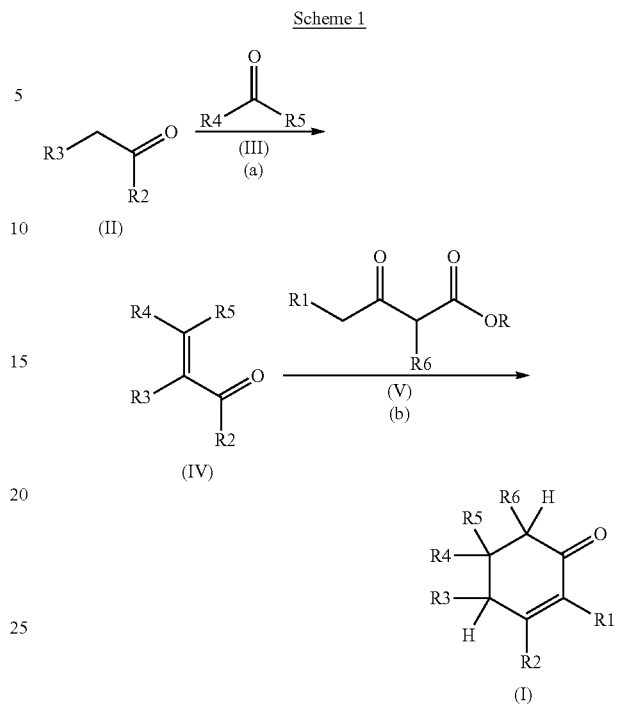

a) $Bu_2NH$; b) cat. NaOH, ROH; $H_2SO_4$

Starting from alpha,beta-unsaturated ketones and aldehydes of general Formula (IV) and 1,3-dicarbonyl compounds of general Formula (V), compounds of general Formula (I) are produced by a base-catalyzed cyclisation reaction with subsequent saponification and decarboxylation. Unavailable compounds of general Formula (IV) can be prepared by base-catalyzed aldol condensation from compounds of general Formulae (II) and (III). The meaning of the residues R1, R2, R3, R4, R5 and R6 in the compounds of Formula (II), (III), (IV) and (V) is respectively the same as the meaning of the identically denoted residues of the compound of Formula (I).

As described above, in the scope of the present invention novel compounds of Formula (I) and corresponding mixtures thereof are provided. The production of these novel compounds of Formula (I) (as described above) is carried out by means of a method according to the invention.

Correspondingly, the present invention also relates to a method for producing these novel compounds of Formula (I), having the following steps:

(i) providing or producing a compound of Formula (IV)

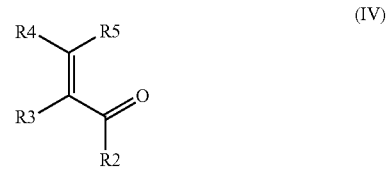

preferably by reacting a compound of Formula (II) and a compound of Formula (III), so that a compound of Formula (IV) results,

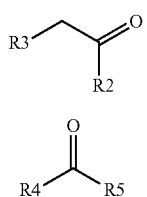

(II)

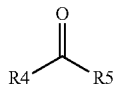

(III)

and (ii) reacting the compound of Formula (IV) and a compound of Formula (V),

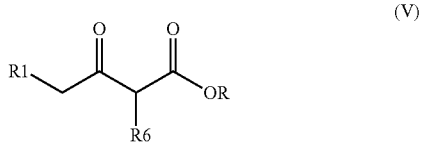

(V)

so that a compound of Formula (I) results, the meaning of the residues R1, R2, R3, R4, R5 and R6 in the compounds of Formula (II), (III), (IV) and (V) respectively being the same as the meaning of the identically denoted residues of the compound of Formula (I).

Preferred according to the invention is a method for producing the novel compounds of Formula (I) in which, in step (ii), an alkali hydroxide, an alkaline earth hydroxide and/or an alcoholate, preferably at least sodium hydroxide or potassium hydroxide, is used as a catalyst.

Likewise preferred according to the invention is a method for producing the novel compounds of Formula (I) in which the reaction in step (ii) is carried out in a solvent, preferably in a polar solvent, particularly preferably in a polar protic solvent, more particularly preferably in an alcohol.

Particularly preferred according to the invention is a method for producing the novel compounds of Formula (I) in which the reaction of the compound of Formula (II) with the compound of Formula (III) in step (ii) takes place in the presence of a secondary amine, preferably selected from the group consisting of piperidine, dibutylamine, dietylamine and dimethylamine and/or the reaction of the compound of Formula (II) with the compound of Formula (III) in step (ii) is carried out in the presence of water as a solvent.

As an alternative, for example, the compounds 13, 43, 44 and 45 according to the invention (synthesis route Scheme 2 and Example 22) of Formula (VIII) can be synthesized in a particularly simple way.

Scheme 2

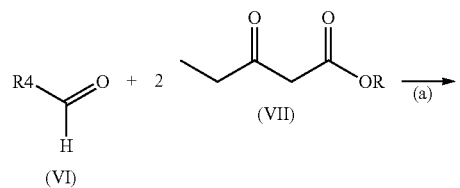

(a)

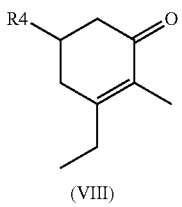

(VIII)

a) Piperidine, NaOH

The compounds of general formula (VIII) are produced starting from aldehydes of general Formula (VI) and 1,3-dicarbonyl compounds of Formula (VII) by a base-catalyzed cyclisation reaction with subsequent saponification and decarboxylation. The residue R4 of Formula (VIII) in this case has the meaning: methyl, ethyl, n-propyl and isopropyl.

Correspondingly, the present invention also relates to an alternative method for producing a compound of Formula (I), preferably one of the compounds 43, 44 or 45 as defined above, where, for the residues of the compound of Formula (I),
R1 denotes methyl,
R2 denotes ethyl,
R3 denotes hydrogen,
R4 denotes methyl, ethyl, n-propyl or isopropyl,
R5 denotes hydrogen,
R6 denotes hydrogen,
having the following steps:
(i) providing or producing a compound of Formula (VI)
the meaning of the residue R4 being the same as the identically denoted residues of the compound of Formula (I),
and
(ii) reacting the compound of Formula (VI) and a compound of Formula (VIII),

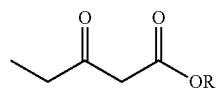

(VII)

the residue R being a branched or unbranched, saturated or unsaturated hydrocarbon residue, preferably methyl, ethyl, propyl, butyl, so that a compound of Formula (I) results, and wherein an alkali hydroxide, an alkaline earth hydroxide and/or an alcoholate, preferably at least sodium hydroxide or potassium hydroxide, is preferably used as a catalyst in step (ii), and wherein the reaction of the compound of Formula (VI) with the compound of Formula (VII) in step (ii) preferably takes place in the presence of a secondary amine, preferably selected from the group consisting of piperidine, dibutylamine, dietylamine and dimethylamine.

The present invention will be explained in more detail below with the aid of examples. Unless otherwise indicated, all data refer to weight.

Example 1: Synthesis of
6-Ethyl-4-isopropylcyclohex-2-en-1-one (1)

Example 1.1: Synthesis of
3-Methyl-2-methylenebutanal

Dibutylamine (9.3 g, 70 mmol) is added dropwise at 80° C. to a solution of isovaleraldehyde (206.7 g, 2.4 mol) and 37% aqueous formaldehyde solution (200.6 g, 2.5 mol). The reaction mixture is then heated under reflux for 2.5 hours. For recovery, the reaction solution is cooled to room temperature and the phases are separated. 3-Methyl-2-methylenebutanal is obtained in the form of a colorless oil (240 g, 96%).

$^1$H-NMR (CDCl$_3$, 400 MHz): δ 9.54 (s, 1H), 6.25 (m, 1H), 5.95 (s, 1H), 2.80 (m, 1H), 1.08 ppm (d, J=7 Hz, 6H). $^{13}$C-NMR (CDCl$_3$, 100 MHz): δ 194.7, 156.5, 132.2, 26.2, 21.4 ppm. MS (EI): m/z=27 (38), 41 (100), 55 (60), 69 (59), 83 (28), 98 (39, M$^{.+}$).

Example 1.2: Synthesis of 6-Ethyl-4-isopropylcyclohex-2-en-1-one (1)

At 0° C., ethyl-2-ethyl acetoacetate (17.5 g, 0.11 mol) in ethanol (25 ml) is added dropwise to 50% aqueous NaOH (8.8 g, 0.11 mol) in ethanol (90 ml), then 3-methyl-2-methylenebutanal (10.3 g, 0.11 mol) in ethanol (25 ml) is added dropwise. The reaction mixture is heated under reflux for 1 hour and the solvent is subsequently distilled off. Water (170 ml) and MtBE (150 ml) are added to the reaction mixture and the phases are separated. The organic phase is neutralized with 50% aqueous sulfuric acid (8.8 g), dried over sodium sulfate and concentrated in a vacuum. Column chromatographic purification on silica gel (eluent: cyclohexane/acetic acid ethyl ester 40/1) gives 6-ethyl-4-isopropylcyclohex-2-en-1-one as an isomer mixture in the form of a colorless oil (2.8 g, 17%).

Main Compound:

$^1$H-NMR (CDCl$_3$, 400 MHz): δ 6.81 (m, 1H), 6.00 (m, 1H), 2.39 (m, 1H), 2.17 (m, 1H), 2.00 (m, 1H), 1.94 (m, 1H), 1.82 (m, 1H), 1.45 (m, 1H), 1.39 (m, 1H), 0.96 (d, J=7 Hz, 3H), 0.95 (d, J=7 Hz, 3H), 0.94 ppm (t, J=7 Hz, 3H). $^{13}$C-NMR (CDCl$_3$, 100 MHz): δ 201.8, 152.9, 129.9, 47.8, 43.4, 31.7, 30.6, 22.0, 19.3, 19.2, 11.1 ppm. MS (EI): m/z=27 (9), 41 (19), 55 (11), 67 (14), 81 (12), 95 (100), 110 (7), 123 (12), 138 (15), 151 (2), 166 (3, M$^{.+}$).

Secondary Compound:

$^1$H-NMR (CDCl$_3$, 400 MHz): δ 6.84 (m, 1H), 5.93 (m, 1H), 2.30 (m, 2H), 1.90 (m, 2H), 1.82 (m, 1H), 1.72 (m, 1H), 1.50 (m, 1H), 1.00 (d, J=7 Hz, 6H), 0.94 ppm (t, J=7 Hz, 3H). $^{13}$C-NMR (CDCl$_3$, 100 MHz): δ 202.9, 152.9, 128.5, 46.7, 38.9, 31.4, 29.1, 23.1, 19.9, 11.9 ppm. MS (EI): m/z=27 (4), 41 (11), 55 (8), 67 (10), 81 (9), 95 (100), 110 (8), 123 (8), 138 (15), 151 (4), 166 (8, M$^{.+}$).

Odor description of 6-ethyl-4-isopropylcyclohex-2-en-1-one: green, fruity, grapefruit, rhubarb, citric, fresh, floral.

Example 2: Synthesis of 4-Isopropyl-6-methylcyclohex-2-en-1-one (2)

Synthesis as in Example 1.2, starting from 2-methyl acetoacetic acid ethyl ester and 3-methyl-2-methylenebutanal. Fractional distillation gives 4-isopropyl-6-methylcyclohex-2-en-1-one as an isomer mixture in the form of a colorless oil (34%).

Main Compound:

$^1$H-NMR (CDCl$_3$, 400 MHz): δ 6.82 (m, 1H), 6.00 (m, 1H), 2.42 (m, 1H), 2.35 (m, 1H), 1.97 (m, 1H), 1.80 (m, 1H), 1.49 (m, 1H), 1.14 (d, J=7 Hz, 3H), 0.96 (d, J=7 Hz, 3H), 0.94 ppm (d, J=7 Hz, 3H). $^{13}$C-NMR (CDCl$_3$, 100 MHz): δ 202.4, 153.3, 129.5, 43.4, 41.6, 34.1, 31.6, 19.4, 19.1, 15.1 ppm. MS (EI): m/z=27 (13), 43 (23), 55 (9), 67 (17), 82 (21), 95 (100), 110 (42), 137 (4), 152 (15, M$^{.+}$).

Secondary Compound:

$^1$H-NMR (CDCl$_3$, 400 MHz): δ 6.89 (m, 1H), 5.95 (m, 1H), 2.30 (m, 1H), 1.98 (m, 1H), 1.81 (m, 2H), 1.15 (d, J=7 Hz, 3H), 1.00 ppm (d, J=7 Hz, 6H). $^{13}$C-NMR (CDCl$_3$, 100 MHz): δ 203.0, 153.1, 128.3, 39.3, 39.2, 32.2, 31.4, 20.3, 20.1, 15.8 ppm. MS (EI): m/z=27 (11), 43 (26), 55 (9), 67 (17), 82 (17), 95 (100), 110 (41), 137 (3), 152 (13, M$^{.+}$).

Odor description of 4-isopropyl-6-methylcyclohex-2-en-1-one: fresh, sweet, spicy, aromatic, fruity, grapefruit, wormwood.

Flavor description of 4-isopropyl-6-methylcyclohex-2-en-1-one: herb, sage, balsamic, spearmint, cooling.

Example 3: Synthesis of 4-Isopropyl-2-methylcyclohex-2-en-1-one (3)

Synthesis as in Example 1.2, starting from methyl-3-oxovalerate and 3-methyl-2-methylenebutanal. Column chromatographic purification on silica gel (eluent: cyclohexane/acetic acid ethyl ester 40/1 through 30/1) gives 4-isopropyl-2-methylcyclohex-2-en-1-one as an isomer mixture in the form of a colorless oil (17%).

$^1$H-NMR (CDCl$_3$, 400 MHz): δ 6.65 (m, 1H), 2.53 (m, 1H), 2.32 (m, 1H), 2.27 (m, 1H), 1.97 (m, 1H), 1.78 (m, 3H), 1.76 (m, 1H), 1.72 (m, 1H), 0.96 (d, J=7 Hz, 3H), 0.94 ppm (d, J=7 Hz, 3H). $^{13}$C-NMR (CDCl$_3$, 100 MHz): δ 200.4, 149.5, 135.5, 42.9, 37.7, 31.8, 25.7, 19.7, 19.4, 16.1 ppm. MS (EI): m/z=27 (18), 41 (46), 53 (19), 67 (23), 81 (46), 95 (100), 110 (79), 123 (4), 137 (8), 152 (44, M$^{.+}$).

Odor description of 4-isopropyl-2-methylcyclohex-2-en-1-one: spicy, herb, fat, floral, cumin.

Example 4: Synthesis of 2-ethyl-4-isopropylcyclohex-2-en-1-one (4)

Synthesis as in Example 1.2, starting from ethyl-3-oxohexanoate and 3-methyl-2-methylenebutanal. Column chromatographic purification on silica gel (eluent: cyclohexane/acetic acid ethyl ester 25/1) gives 2-ethyl-4-isopropylcyclohex-2-en-1-one as an isomer mixture in the form of a colorless oil (23%).

$^1$H-NMR (CDCl$_3$, 400 MHz): δ 6.60 (m, 1H), 2.52 (m, 1H), 2.32 (m, 1H), 2.28 (m, 1H), 2.21 (m, 1H), 1.96 (m, 1H), 1.80 (m, 1H), 1.70 (m, 1H), 1.01 (t, J=7 Hz, 3H), 0.97 (d, J=7 Hz, 3H), 0.95 ppm (d, J=7 Hz, 3H). $^{13}$C-NMR (CDCl$_3$, 100 MHz): δ 199.9, 147.9, 141.0, 42.7, 37.9, 31.8, 25.4, 22.6, 19.7, 19.4, 13.1 ppm. MS (EI): m/z=27 (49), 41 (93), 55 (52), 67 (56), 81 (100), 95 (96), 109 (83), 123 (61), 137 (7), 151 (9), 166 (39, M$^{.+}$).

Odor description of 2-ethyl-4-isopropylcyclohex-2-en-1-one: fruity, damascone, saffron, spicy, chamomile.

Flavor description of 2-ethyl-4-isopropylcyclohex-2-en-1-one: herb, pepper, geranium, woody, flowery.

Example 5: Synthesis of 5-ethyl-4-methylcyclohex-2-en-1-one (5)

Synthesis as in Example 1.2, starting from ethyl acetoacetate and 2-methyl-2-pentenal. Fractional distillation gives 5-ethyl-4-methylcyclohex-2-en-1-one as an isomer mixture in the form of a colorless oil (10%).

Main Compound:

$^1$H-NMR (CDCl$_3$, 400 MHz): δ 6.74 (m, 1H), 5.94 (m, 1H), 2.55 (m, 1H), 2.28 (m, 1H), 2.14 (m, 1H), 1.70 (m, 1H), 1.64 (m, 1H), 1.35 (m, 1H), 1.18 (d, J=7 Hz, 3H), 0.91 ppm (t, J=7 Hz, 3H). $^{13}$C-NMR (CDCl$_3$, 100 MHz): δ 200.4, 156.2, 128.3, 43.1, 41.7, 35.9, 25.7, 18.5, 10.5 ppm. MS (EI): m/z=27 (25), 39 (34), 54 (45), 68 (42), 82 (100), 95 (13), 109 (19), 123 (4), 138 (26, M·+).

Secondary Compound:

$^1$H-NMR (CDCl$_3$, 400 MHz): δ 6.96 (m, 1H), 5.94 (m, 1H), 2.55 (m, 1H), 2.35 (m, 2H), 2.06 (m, 1H), 1.43 (m, 2H), 1.02 (d, J=7 Hz, 3H), 0.93 ppm (t, J=7 Hz, 3H). $^{13}$C-NMR (CDCl$_3$, 100 MHz): δ 200.1, 156.1, 128.1, 39.5, 39.2, 33.0, 24.9, 12.0, 11.3 ppm. MS (EI): m/z=27 (19), 39 (28), 54 (40), 68 (9), 82 (100), 95 (9), 109 (15), 123 (2), 138 (19, M·+).

Odor description of 5-ethyl-4-methylcyclohex-2-en-1-one: spicy, almond.

Example 6: Synthesis of 5-ethyl-2,4-dimethylcyclohex-2-en-1-one (8)

Synthesis as in Example 1.2, starting from methyl-3-oxovalerate and 2-methyl-2-pentenal. Column chromatographic purification on silica gel (eluent: cyclohexane/acetic acid ethyl ester 20/1) gives 5-ethyl-2,4-dimethylcyclohex-2-en-1-one as an isomer mixture in the form of a colorless oil (5%).

Main Compound:

$^1$H-NMR (CDCl$_3$, 400 MHz): δ 6.48 (m, 1H), 2.56 (m, 1H), 2.25 (m, 1H), 2.11 (m, 1H), 1.75 (m, 3H), 1.64 (m, 2H), 1.26 (m, 1H), 1.14 (d, J=7 Hz, 3H), 0.91 ppm (t, J=7 Hz, 3H). $^{13}$C-NMR (CDCl$_3$, 100 MHz): δ 200.5, 151.5, 134.2, 43.6, 42.0, 36.2, 25.7, 18.8, 15.6, 10.6 ppm. MS (EI): m/z=27 (15), 41 (45), 55 (21), 69 (60), 82 (14), 95 (100), 109 (9), 123 (18), 137 (2), 152 (11, M·+).

Secondary Compound:

$^1$H-NMR (CDCl$_3$, 400 MHz): δ 6.70 (m, 1H), 2.50 (m, 1H), 2.30 (m, 2H), 2.04 (m, 1H), 1.75 (m, 3H), 1.35 (m, 2H), 0.99 (d, J=7 Hz, 3H), 0.90 ppm (t, J=7 Hz, 3H). $^{13}$C-NMR (CDCl$_3$, 100 MHz): δ 200.2, 151.3, 133.9, 39.6, 33.2, 24.9, 15.8, 12.3, 11.3 ppm. MS (EI): m/z=27 (17), 41 (42), 55 (25), 69 (58), 82 (8), 95 (100), 109 (17), 123 (33), 137 (2), 152 (17, M·+).

Odor description of 5-ethyl-2,4-dimethylcyclohex-2-en-1-one: aromatic, herb, spicy, medicinal, almond, coumarin.

Example 7: Synthesis of 2,5-diethyl-4-methylcyclohex-2-en-1-one (9)

Synthesis as in Example 1.2, starting from ethyl-3-oxohexanoate and 2-methyl-2-pentenal. Column chromatographic purification on silica gel (eluent: cyclohexane/acetic acid ethyl ester 99/1) gives 2,5-diethyl-4-methylcyclohex-2-en-1-one as an isomer mixture in the form of a colorless oil (10%).

Main Compound:

$^1$H-NMR (CDCl$_3$, 400 MHz): δ 6.42 (m, 1H), 2.86 (m, 1H), 2.30-2.15 (m, 4H), 1.64 (m, 2H), 1.30 (m, 1H), 1.15 (d, J=7 Hz, 3H), 1.00 (t, J=7 Hz, 3H), 0.99 ppm (t, J=7 Hz, 3H). $^{13}$C-NMR (CDCl$_3$, 100 MHz): δ 200.2, 149.9, 139.7, 43.4, 42.3, 36.1, 25.7, 22.1, 18.9, 12.9, 10.6 ppm. MS (EI): m/z=29 (15), 41 (41), 55 (51), 67 (79), 83 (74), 95 (50), 109 (100), 124 (11), 137 (75), 151 (8), 166 (30, M·+).

Secondary Compound:

$^1$H-NMR (CDCl$_3$, 400 MHz): δ 6.65 (m, 1H), 2.55 (m, 1H), 2.35-2.15 (m, 4H), 2.02 (m, 1H), 1.37 (m, 2H), 1.00 (t, J=7 Hz, 3H), 0.99 (d, J=7 Hz, 3H), 0.92 ppm (t, J=7 Hz, 3H). $^{13}$C-NMR (CDCl$_3$, 100 MHz): δ 199.8, 149.7, 139.4, 39.8, 39.4, 33.1, 24.8, 22.2, 12.9, 12.4, 11.3 ppm. MS (EI): m/z=29 (15), 41 (42), 55 (48), 67 (93), 83 (67), 95 (55), 109 (100), 124 (15), 137 (71), 151 (8), 166 (27, M·+).

Odor description of 2,5-diethyl-4-methylcyclohex-2-en-1-one: spicy, aromatic, spearmint, saffron, aniseed, fennel, tobacco.

Example 8: Synthesis of 3-ethyl-5-methylcyclohex-2-en-1-one (10)

Synthesis as in Example 1.2, starting from ethyl acetoacetate and 4-hexen-3-one. Fractional distillation gives 3-ethyl-5-methylcyclohex-2-en-1-one as an isomer mixture in the form of a colorless oil (55%).

$^1$H-NMR (CDCl$_3$, 400 MHz): δ 5.87 (m, 1H), 2.43 (m, 1H), 2.31 (m, 1H), 2.24 (m, 2H), 2.17 (m, 1H), 2.04 (m, 1H), 2.03 (m, 1H), 1.10 (t, J=7 Hz, 3H), 1.07 ppm (d, J=7 Hz, 3H). $^{13}$C-NMR (CDCl$_3$, 100 MHz): δ 200.3, 167.0, 124.3, 45.6, 38.2, 30.8, 30.2, 21.2, 11.3 ppm. MS (EI): m/z=39 (19), 53 (15), 67 (30), 81 (37), 96 (100), 109 (2), 123 (6), 138 (42, M·+).

Odor description of 3-ethyl-5-methylcyclohex-2-en-1-one: spicy, aromatic, lovage, celery, fenugreek.

Example 9: Synthesis of 3-ethyl-5,6-dimethylcyclohex-2-en-1-one (12)

Synthesis as in Example 1.2, starting from 2-methyl acetoacetic ethyl ester and 4-s hexen-3-one. Fractional distillation gives 3-ethyl-5,6-dimethylcyclohex-2-en-1-one as an isomer mixture in the form of a colorless oil (12%).

Main Compound:

$^1$H-NMR (CDCl$_3$, 400 MHz): δ 5.85 (m, 1H), 2.30 (m, 1H), 2.21 (m, 2H), 2.10 (m, 1H), 1.99 (m, 1H), 1.84 (m, 1H), 1.15 (d, J=7 Hz, 3H), 1.09 (t, J=7 Hz, 3H), 1.08 ppm (d, J=7 Hz, 3H). $^{13}$C-NMR (CDCl$_3$, 100 MHz): δ 201.2, 165.3, 123.8, 47.8, 38.2, 36.2, 30.6, 20.0, 12.4, 11.3 ppm. MS (EI): m/z=27 (11), 39 (17), 53 (13), 67 (26), 81 (32), 96 (100), 109 (4), 123 (4), 137 (9), 152 (11, M·+).

Secondary Compound:

$^1$H-NMR (CDCl$_3$, 400 MHz): δ 5.81 (m, 1H), 2.43 (m, 1H), 2.30 (m, 2H), 2.21 (m, 2H), 2.10 (m, 1H), 1.12 (t, J=7 Hz, 3H), 1.04 (d, J=7 Hz, 3H), 0.95 ppm (d, J=7 Hz, 3H). $^{13}$C-NMR (CDCl$_3$, 100 MHz): δ 203.5, 165.1, 123.3, 45.5, 35.8, 33.3, 30.7, 15.7, 11.3, 10.8 ppm. MS (EI): m/z=27 (11), 39 (17), 53 (13), 67 (26), 81 (32), 96 (100), 109 (2), 123 (4), 137 (9), 152 (13, M·+).

Odor description of 5-ethyl-5,6-dimethylcyclohex-2-en-1-one: spicy, saffron, green, natural, mint.

Example 10: Synthesis of 3-ethyl-2,5-dimethylcyclohex-2-en-1-one (13)

Synthesis as in Example 1.2, starting from methyl-3-oxovalerate and 4-hexen-3-one. Fractional distillation gives 3-ethyl-2,5-dimethylcyclohex-2-en-1-one as an isomer mixture in the form of a colorless oil (31%).

$^1$H-NMR (CDCl$_3$, 400 MHz): δ 2.47 (m, 1H), 2.36 (m, 1H), 2.23 (m, 2H), 2.10 (m, 1H), 2.08 (m, 1H), 2.03 (m, 1H), 1.76 (m, 3H), 1.07 (t, J=7 Hz, 3H), 1.04 ppm (m, 3H). $^{13}$C-NMR (CDCl$_3$, 100 MHz): δ 199.8, 159.5, 129.8, 45.8, 38.7, 29.8, 28.2, 21.2, 11.6, 10.2 ppm. MS (EI): m/z=27 (19), 41 (42), 53 (22), 67 (100), 82 (27), 95 (32), 110 (90), 123 (10), 137 (27), 152 (68, M·+).

Odor description of 3-ethyl-2,5-dimethylcyclohex-2-en-1-one: spicy, woody, leather, saffron, green, soft, creamy.

Flavor description of 3-ethyl-2,5-dimethylcyclohex-2-en-1-one: medicinal, fresh, woody.

Example 11: Synthesis of 2,3-diethyl-5-methylcyclohex-2-en-1-one (14)

Synthesis as in Example 1.2, starting from ethyl-3-oxohexanoate and 4-hexen-3-one. Fractional distillation gives 2,3-diethyl-5-methylcyclohex-2-en-1-one as an isomer mixture in the form of a colorless oil (40%).

$^1$H-NMR (CDCl$_3$, 400 MHz): δ 2.64 (m, 1H), 2.34 (m, 1H), 2.27 (m, 4H), 2.08 (m, 3H), 1.09 (t, J=8 Hz, 3H), 1.03 (d, J=6 Hz, 3H), 0.92 ppm (t, J=7 Hz, 3H). $^{13}$C-NMR (CDCl$_3$, 100 MHz): δ 199.5, 159.1, 136.0, 46.2, 38.5, 29.8, 27.7, 21.2, 18.1, 14.2, 12.4 ppm. MS (EI): m/z=29 (11), 41 (44), 55 (21), 67 (32), 81 (100), 95 (32), 109 (47), 124 (93), 137 (46), 151 (30), 166 (100, M$^{·+}$).

Odor description of 2,3-diethyl-5-methylcyclohex-2-en-1-one: spicy, herb, saffron.

Example 12: Synthesis of 4,5-dimethylcyclohex-2-en-1-one (15)

Synthesis as in Example 1.2, starting from ethyl acetoacetate and tiglic aldehyde. Fractional distillation gives 4,5-dimethylcyclohex-2-en-1-one as an isomer mixture in the form of a colorless oil (15%).

Main Compound:
$^1$H-NMR (CDCl$_3$, 400 MHz): δ 6.74 (m, 1H), 5.91 (m, 1H), 2.46 (m, 1H), 2.17 (m, 1H), 2.15 (m, 1H), 1.83 (m, 1H), 1.18 (d, J=7 Hz, 3H), 1.08 ppm (d, J=7 Hz, 3H). $^{13}$C-NMR (CDCl$_3$, 100 MHz): δ 200.3, 156.2, 128.5, 45.6, 38.3, 37.1, 19.6, 18.5 ppm. MS (EI): m/z=27 (27), 39 (40), 54 (53), 68 (61), 82 (100), 96 (19), 109 (10), 124 (41, M$^{·+}$).

Secondary Compound:
$^1$H-NMR (CDCl$_3$, 400 MHz): δ 6.56 (m, 1H), 5.94 (m, 1H), 2.55 (m, 1H), 2.34 (m, 3H), 1.06 (d, J=7 Hz, 3H), 0.99 ppm (d, J=7 Hz, 3H). $^{13}$C-NMR (CDCl$_3$, 100 MHz): δ 200.6, 155.4, 128.1, 42.7, 34.7, 32.7, 16.6, 13.4 ppm. MS (EI): m/z=27 (23), 39 (33), 54 (48), 68 (27), 82 (100), 96 (19), 109 (10), 124 (30, M$^{·+}$).

Odor description of 4,5-dimethylcyclohex-2-en-1-one: almond, sweet, tobacco, cherry, fruity, coumarin.

Example 13: Synthesis of 2,4,5-Trimethylcyclohex-2-en-1-one (18)

Synthesis as in Example 1.2, starting from methyl-3-oxovalerate and tiglic aldehyde. Fractional distillation gives 2,4,5-trimethylcyclohex-2-en-1-one as an isomer mixture in the form of a colorless oil (30%).

Main Compound:
$^1$H-NMR (CDCl$_3$, 400 MHz): δ 6.48 (m, 1H), 2.45 (m, 1H), 2.14 (m, 1H), 2.12 (m, 1H), 1.79 (m, 1H), 1.76 (m, 3H), 1.14 (d, J=7 Hz, 3H), 1.05 ppm (d, J=7 Hz, 3H). $^{13}$C-NMR (CDCl$_3$, 100 MHz): δ 200.5, 151.5, 134.4, 45.8, 38.6, 37.5, 19.5, 18.8, 15.6 ppm. MS (EI): m/z=27 (19), 41 (56), 53 (28), 69 (100), 81 (48), 95 (92), 110 (42), 123 (15), 138 (33, M$^{·+}$).

Secondary Compound:
$^1$H-NMR (CDCl$_3$, 400 MHz): δ 6.60 (m, 1H), 2.53 (m, 1H), 2.33 (m, 3H), 1.76 (m, 3H), 1.03 (d, J=7 Hz, 3H), 0.95 ppm (d, J=7 Hz, 3H). $^{13}$C-NMR (CDCl$_3$, 100 MHz): δ 200.1, 150.6, 133.9, 42.8, 37.1, 34.1, 16.5, 15.7, 13.8 ppm. MS (EI): m/z=27 (22), 41 (60), 53 (31), 69 (100), 81 (59), 95 (100), 110 (47), 123 (15), 138 (31, M$^{·+}$).

Odor description of 2,4,5-trimethylcyclohex-2-en-1-one: spicy, aromatic, cherry, coumarin, almond.

Example 14: Synthesis of 2-ethyl-4,5-dimethylcyclohex-2-en-1-one (19)

Synthesis as in Example 1.2, starting from ethyl-3-oxohexanoate and tiglic aldehyde. Fractional distillation gives 2-ethyl-4,5-dimethylcyclohex-2-en-1-one as an isomer mixture in the form of a colorless oil (29%).

Main Compound:
$^1$H-NMR (CDCl$_3$, 400 MHz): δ 6.42 (m, 1H), 2.46 (m, 1H), 2.19 (m, 2H), 2.17-2.10 (m, 2H), 1.77 (m, 1H), 1.15 (d, J=7 Hz, 3H), 1.05 (d, J=6 Hz, 3H), 1.00 ppm (t, J=8 Hz, 3H). $^{13}$C-NMR (CDCl$_3$, 100 MHz): δ 200.1, 149.8, 139.9, 46.1, 38.6, 37.4, 22.1, 19.5, 18.9, 12.9 ppm. MS (EI): m/z=27 (24), 41 (42), 55 (50), 67 (93), 83 (69), 95 (100), 110 (68), 123 (24), 137 (35), 152 (43, M$^{·+}$).

Secondary Compound:
$^1$H-NMR (CDCl$_3$, 400 MHz): δ 6.53 (m, 1H), 2.52 (m, 1H), 2.35-2.27 (m, 3H), 2.19 (m, 2H), 1.03 (d, J=7 Hz, 3H), 1.00 (t, J=7 Hz, 3H), 0.93 ppm (m, 3H). $^{13}$C-NMR (CDCl$_3$, 100 MHz): δ 199.6, 148.8, 139.4, 43.1, 34.8, 32.9, 22.2, 16.4, 14.0, 12.9 ppm. MS (EI): m/z=27 (23), 41 (42), 55 (58), 67 (86), 83 (78), 95 (100), 110 (60), 123 (23), 137 (38), 152 (48, M$^{·+}$).

Odor description of 2-ethyl-4,5-dimethylcyclohex-2-en-1-one: spicy, herb, saffron.

Example 15: Synthesis of 2,3,4,5-tetramethylcyclohex-2-en-1-one (23)

Synthesis as in Example 1.2, starting from methyl-3-oxovalerate and 3-methyl-3-penten-2-one. Fractional distillation gives 2,3,4,5-tetramethylcyclohex-2-en-1-one as an isomer mixture in the form of a colorless oil (12%).

Main Compound:
$^1$H-NMR (CDCl$_3$, 400 MHz): δ 2.30 (m, 1H), 2.25 (m, 3H), 1.95 (m, 3H), 1.74 (m, 3H), 1.02 (d, J=7 Hz, 3H), 0.98 ppm (d, J=6 Hz, 3H). $^{13}$C-NMR (CDCl$_3$, 100 MHz): δ 199.2, 160.8, 129.8, 41.3, 40.3, 32.2, 20.5, 18.4, 11.1, 10.9 ppm. MS (EI): m/z=27 (15), 41 (40), 55 (30), 67 (100), 83 (75), 95 (65), 110 (97), 123 (6), 137 (12), 152 (59, M$^{·+}$).

Secondary Compound:
$^1$H-NMR (CDCl$_3$, 400 MHz): δ 2.61 (m, 1H), 2.16 (m, 1H), 2.10 (m, 1H), 1.95 (m, 1H), 1.91 (m, 3H), 1.75 (m, 3H), 1.22 (d, J=7 Hz, 3H), 1.04 ppm (d, J=6 Hz, 3H). $^{13}$C-NMR (CDCl$_3$, 100 MHz): δ 198.4, 157.1, 129.9, 43.2, 41.5, 34.8, 20.2, 20.1, 18.1, 10.2 ppm. MS (EI): m/z=27 (15), 41 (41), 55 (32), 67 (100), 83 (75), 95 (64), 110 (85), 123 (7), 137 (15), 152 (55, M$^{·+}$).

Odor description of 2,3,4,5-tetramethylcyclohex-2-en-1-one: spicy, saffron, leather, tobacco.

Flavor description of 2,3,4,5-tetramethylcyclohex-2-en-1-one: medicinal, woody pungent, bitter, cooling.

Example 16: Synthesis of 2-ethyl-3,4,5-trimethylcyclohex-2-en-1-one (24)

Synthesis as in Example 1.2, starting from ethyl-3-oxohexanoate and 3-methyl-3-penten-2-one. Fractional distillation gives 2-ethyl-3,4,5-trimethylcyclohex-2-en-1-one as an isomer mixture in the form of a colorless oil (11%).

Main Compound:
$^1$H-NMR (CDCl$_3$, 400 MHz): δ 2.35-2.20 (m, 6H), 1.96 (m, 3H), 1.02 (d, J=7 Hz, 3H), 0.97 (d, J=6 Hz, 3H), 0.91 ppm (t, J=8 Hz, 3H). $^{13}$C-NMR (CDCl$_3$, 100 MHz): δ 198.7, 160.4, 135.9, 41.3, 40.5, 32.2, 19.8, 18.5, 18.4, 13.4, 11.2 ppm. MS (EI): m/z=29 (16), 41 (53), 55 (24), 67 (41), 81 (100), 97 (62), 109 (72), 124 (87), 137 (19), 151 (38), 166 (79, M·+).

Secondary Compound:
$^1$H-NMR (CDCl$_3$, 400 MHz): δ 2.60 (m, 1H), 2.35-2.20 (m, 2H), 2.14 (m, 1H), 2.08 (m, 1H), 1.95-1.93 (m, 1H), 1.92 (m, 3H), 1.22 (d, J=7 Hz, 3H), 1.04 (d, J=7 Hz, 3H), 0.91 ppm (t, J=8 Hz, 3H). $^{13}$C-NMR (CDCl$_3$, 100 MHz): δ 197.9, 156.5, 136.0, 43.2, 41.7, 34.7, 20.0, 19.6, 18.5, 18.2, 13.3 ppm. MS (EI): m/z=29 (13), 41 (52), 55 (22), 67 (36), 81 (100), 97 (67), 109 (66), 124 (96), 137 (19), 151 (39), 166 (77, M·+).

Odor description of 2-ethyl-3,4,5-trimethylcyclohex-2-en-1-one: fresh, minty, tobacco, saffron, spicy, lovage.

Example 17: Synthesis of 2-Ethyl-5,5-dimethylcyclohex-2-en-1-one (28)

Synthesis as in Example 1.2, starting from ethyl-3-oxo-hexanoate and 3-methylbut-2-enal. Column chromatographic purification on silica gel (eluent: cyclohexane/acetic acid ethyl ester 30/1) gives 2-ethyl-5,5-dimethylcyclohex-2-en-1-one in the form of a colorless oil (4%).

$^1$H-NMR (CDCl$_3$, 400 MHz): δ 6.57 (m, 1H), 2.28 (s, 2H), 2.24 (m, 2H), 2.22 (m, 2H), 1.02 (s, 6H), 1.01 ppm (t, J=8 Hz, 3H). $^{13}$C-NMR (CDCl$_3$, 100 MHz): δ 199.7, 141.6, 140.2, 52.2, 40.1, 34.0, 28.3, 22.1, 12.9 ppm. MS (EI): m/z=27 (5), 41 (15), 53 (12), 67 (30), 81 (17), 96 (100), 109 (20), 123 (2), 137 (5), 152 (27, M·+).

Odor description of 2-ethyl-5,5-dimethylcyclohex-2-en-1-one: spicy, lovage, saffron, apple.

Example 18: Synthesis of 2,3,5,5-tetramethylcyclohex-2-en-1-one (29)

Synthesis as in Example 1.2, starting from methyl-3-oxovalerate and mesityl oxide. Fractional distillation gives 2,3,5,5-tetramethylcyclohex-2-en-1-one in the form of a colorless oil (5%).

$^1$H-NMR (CDCl$_3$, 400 MHz): δ 2.24 (s, 2H), 2.20 (m, 2H), 1.90 (m, 3H), 1.77 (m, 3H), 1.00 ppm (s, 6H). $^{13}$C-NMR (CDCl$_3$, 100 MHz): δ 199.3, 152.5, 129.8, 51.1, 47.0, 32.7, 28.3, 21.6, 10.5 ppm. MS (EI): m/z=27 (8), 41 (15), 53 (11), 68 (32), 83 (6), 96 (100), 109 (9), 124 (2), 137 (4), 152 (34, M·+).

Odor description of 2,3,5,5-tetramethylcyclohex-2-en-1-one: tobacco, spicy, leather, animal.

Flavor description of 2,3,5,5-tetramethylcyclohex-2-en-1-one: medicinal, fresh, spearmint, cereal, hay, clover.

Example 19: Synthesis of 2-ethyl-3,5,5-trimethyl-cyclohex-2-en-1-one (30)

Synthesis as in Example 1.2, starting from ethyl-3-oxo-hexanoate and mesityl oxide. Fractional distillation gives 2-ethyl-3,5,5-trimethyl-cyclohex-2-en-1-one in the form of a colorless oil (6%).

$^1$H-NMR (CDCl$_3$, 400 MHz): δ 2.31 (m, 2H), 2.23 (s, 2H), 2.21 (m, 2H), 1.92 (m, 3H), 1.00 (s, 6H), 0.93 ppm (t, J=7 Hz, 3H). $^{13}$C-NMR (CDCl$_3$, 100 MHz): δ 198.8, 152.0, 136.0, 51.4, 47.0, 32.7, 28.2, 21.0, 18.2, 13.5 ppm. MS (EI): m/z=29 (8), 41 (25), 55 (9), 67 (49), 82 (47), 95 (9), 110 (100), 123 (9), 137 (1), 151 (6), 166 (36, M·+).

Odor description of 2-ethyl-3,5,5-trimethylcyclohex-2-en-1-one: tobacco, spicy, leather, saffron.

Example 20: Synthesis of 6-ethyl-4-methylcyclohex-2-en-1-one (31)

Synthesis as in Example 1.2, starting from ethyl 2-ethyl acetoacetate and methacrolein. Column chromatographic purification on silica gel (eluent: cyclohexane/acetic acid ethyl ester 30/1) gives 6-ethyl-4-methylcyclohex-2-en-1-one in the form of a colorless oil (15%).

Main Compound:
$^1$H-NMR (CDCl$_3$, 400 MHz): δ 6.71 (m, 1H), 5.94 (m, 1H), 2.60 (m, 1H), 2.19 (m, 1H), 2.12 (m, 1H), 1.93 (m, 1H), 1.40 (m, 1H), 1.36 (m, 1H), 1.15 (d, J=7 Hz, 3H), 0.93 ppm (t, J=7 Hz, 3H). $^{13}$C-NMR (CDCl$_3$, 100 MHz): δ 201.5, 155.2, 128.8, 47.6, 36.6, 32.2, 21.8, 21.0, 11.0 ppm. MS (EI): m/z=27 (15), 39 (22), 54 (31), 67 (11), 82 (100), 96 (59), 110 (53), 123 (7), 138 (4, M·+).

Secondary Compound:
$^1$H-NMR (CDCl$_3$, 400 MHz): δ 6.74 (m, 1H), 5.87 (m, 1H), 2.60 (m, 1H), 2.30 (m, 1H), 2.00 (m, 1H), 1.79 (m, 1H), 1.74 (m, 1H), 1.49 (m, 1H), 1.16 (d, J=7 Hz, 3H), 0.96 ppm (t, J=8 Hz, 3H). $^{13}$C-NMR (CDCl$_3$, 100 MHz): δ 202.3, 154.6, 127.6, 45.8, 34.6, 28.1, 22.8, 19.7, 11.7 ppm. MS (EI): m/z=27 (14), 39 (21), 54 (32), 67 (9), 82 (100), 96 (46), 110 (42), 123 (4), 138 (6, M·+).

Odor description of 6-ethyl-4-methylcyclohex-2-en-1-one: green, nutty, lactone, fruity, cocoa.

Example 21: Synthesis of 4,6-diethylcyclohex-2-en-1-one (32)

Synthesis as in Example 1.2, starting from ethyl 2-ethyl acetoacetate and 2-ethylacrolein. Column chromatographic purification on silica gel (eluent: cyclohexane/acetic acid ethyl ester 30/1) gives 4,6-diethylcyclohex-2-en-1-one as an isomer mixture in the form of a colorless oil (12%).

Main Compound:
$^1$H-NMR (CDCl$_3$, 400 MHz): δ 6.78 (m, 1H), 5.97 (m, 1H), 2.39 (m, 1H), 2.18 (m, 1H), 2.12 (m, 1H), 1.94 (m, 1H), 1.54 (m, 2H), 1.40 (m, 1H), 1.30 (m, 1H), 1.00 (t, J=7 Hz, 3H), 0.94 ppm (t, J=8 Hz, 3H). $^{13}$C-NMR (CDCl$_3$, 100 MHz): δ 201.8, 153.9, 129.3, 47.7, 38.8, 33.9, 28.2, 22.0, 11.1 ppm. MS (EI): m/z=27 (6), 41 (12), 55 (16), 67 (16), 81 (76), 96 (100), 109 (10), 124 (31), 152 (6, M·+).

Secondary Compound:
$^{13}$C-NMR (CDCl$_3$, 100 MHz): δ 202.7, 153.4, 128.0, 46.1, 34.7, 32.0, 27.2, 22.9, 11.8, 11.7 ppm. MS (EI): m/z 27 (8), 41 (14), 55 (16), 67 (18), 81 (82), 96 (100), 109 (8), 124 (24), 152 (10, M·+).

Odor description of 4,6-diethylceeyclohex-2-en-1-one: spicy, caraway, fatty, green.

Example 22: Synthesis of 4-ethyl-6-methylcyclohex-2-en-1-one (33)

Synthesis as in Example 1.2, starting from 2-methyl acetoacetic ethyl ester and 2-ethylacrolein. Column chromatographic purification on silica gel (eluent: cyclohexane/acetic acid ethyl ester 30/1) gives 4-ethyl-6-methylcyclohex-2-en-1-one as an isomer mixture in the form of a colorless oil (35%).

Main Compound:
$^1$H-NMR (CDCl$_3$, 400 MHz): δ 6.79 (m, 1H), 5.97 (m, 1H), 2.42 (m, 1H), 2.37 (m, 1H), 2.09 (m, 1H), 1.52 (m, 1H), 1.45 (m, 1H), 1.39 (m, 1H), 1.14 (d, J=7 Hz, 3H), 0.99 ppm (t, J=7 Hz, 3H). $^{13}$C-NMR (CDCl$_3$, 100 MHz): δ 202.4, 154.2, 128.8, 41.5, 38.7, 37.5, 28.1, 15.0, 11.1 ppm. MS (EI): m/z=27 (14), 41 (17), 53 (20), 67 (18), 81 (100), 96 (81), 110 (9), 138 (19, M$^{.+}$).

Secondary Compound:
$^1$H-NMR (CDCl$_3$, 400 MHz): δ 6.85 (m, 1H), 5.91 (m, 1H), 2.53 (m, 1H), 2.37 (m, 1H), 2.09 (m, 1H), 1.87 (m, 2H), 1.58 (m, 1H), 1.45 (m, 1H), 1.15 (d, J=7 Hz, 3H), 1.03 ppm (t, J=7 Hz, 3H). $^{13}$C-NMR (CDCl$_3$, 100 MHz): δ 202.8, 153.6, 127.9, 38.6, 35.1, 34.9, 26.7, 15.6, 12.0 ppm. MS (EI): m/z=27 (14), 41 (16), 53 (20), 67 (18), 81 (100), 96 (78), 110 (9), 138 (17, M$^{.+}$).

Odor description of 4-ethyl-6-methylcyclohex-2-en-1-one: spicy, caraway, green, watery, blossom.

Example 23: Synthesis of 2,4-diethylcyclohex-2-en-1-one (34)

Synthesis as in Example 1.2, starting from ethyl-3-oxo-hexanoate and 2-ethylacrolein. Column chromatographic purification on silica gel (eluent: cyclohexane/acetic acid ethyl ester 30/1) gives 2,4-diethylcyclohex-2-en-1-one as an isomer mixture in the form of a colorless oil (15%).

$^1$H-NMR (CDCl$_3$, 400 MHz): δ 6.56 (m, 1H), 2.50 (m, 1H), 2.33 (m, 1H), 2.31 (m, 1H), 2.20 (m, 2H), 2.07 (m, 1H), 1.62 (m, 1H), 1.53 (m, 1H), 1.44 (m, 1H), 1.01 (t, J=7 Hz, 3H), 0.99 ppm (t, J=7 Hz, 3H). $^{13}$C-NMR (CDCl$_3$, 100 MHz): δ 199.8, 148.6, 140.3, 37.9, 37.5, 28.5, 28.0, 22.5, 12.9, 11.4 ppm. MS (EI): m/z=27 (22), 41 (27), 55 (32), 67 (33), 81 (100), 95 (69), 110 (59), 123 (42), 137 (8), 152 (61, M$^{.+}$).

Odor description of 2,4-diethylcyclohex-2-en-1-one: green, technical, spicy, coumarin.

Example 24: Synthesis of 4-Ethyl-5-methylcyclohex-2-en-1-one (37)

Synthesis as in Example 1.2, starting from ethyl acetoacetate and 2-ethylcrotonaldehyde. Column chromatographic purification on silica gel (eluent: cyclohexane/acetic acid ethyl ester 10/1) gives 4-ethyl-5-methylcyclohex-2-en-1-one as an isomer mixture in the form of a colorless oil (10%).

Main Compound:
$^1$H-NMR (CDCl$_3$, 400 MHz): δ 6.85 (m, 1H), 6.02 (m, 1H), 2.48 (m, 1H), 2.16 (m, 1H), 2.08-1.98 (m, 2H), 1.73 (m, 1H), 1.54 (m, 1H), 1.06 (d, J=6 Hz, 3H), 0.96 ppm (t, J=7 Hz, 3H). $^{13}$C-NMR (CDCl$_3$, 100 MHz): δ 200.2, 154.3, 129.2, 45.3, 44.4, 33.4, 24.1, 19.5, 10.5 ppm. MS (EI): m/z=27 (13), 41 (20), 55 (31), 68 (46), 81 (100), 96 (31), 109 (15), 123 (6), 138 (17, M$^{.+}$).

Secondary Compound:
$^1$H-NMR (CDCl$_3$, 400 MHz): δ 6.83 (m, 1H), 5.99 (m, 1H), 2.42-2.30 (m, 4H), 1.58-1.46 (m, 2H), 1.02 (t, J=7 Hz, 3H), 0.94 ppm (d, J=7 Hz, 3H). $^{13}$C-NMR (CDCl$_3$, 100 MHz): δ 199.9, 153.5, 128.7, 44.6, 418, 32.3, 23.3, 14.7, 11.9 ppm. MS (EI): m/z=27 (11), 41 (18), 55 (27), 68 (30), 81 (100), 96 (36), 109 (13), 123 (4), 138 (15, M$^{.+}$).

Odor description of 4-ethyl-5-methylcyclohex-2-en-1-one: almond, fruity, cherry, cinnamon, balsamic.

Example 25: Synthesis of 3,6-diethylcyclohex-2-en-1-one (40)

Synthesis as in Example 1.2, starting from ethyl 2-ethyl acetoacetate and 1-penten-3-one. Column chromatographic purification on silica gel (eluent: cyclohexane/acetic acid ethyl ester 30/1) gives 3,6-diethylcyclohex-2-en-1-one as an isomer mixture in the form of a colorless oil (26%).

$^1$H-NMR (CDCl$_3$, 400 MHz): δ 5.83 (m, 1H), 2.32 (m, 2H), 2.22 (m, 2H), 2.16-2.05 (m, 2H), 1.86 (m, 1H), 1.73 (m, 1H), 1.43 (m, 1H), 1.10 (t, J=7 Hz, 3H), 0.94 ppm (t, J=8 Hz, 3H). $^{13}$C-NMR (CDCl$_3$, 100 MHz): δ 202.0, 166.4, 124.3, 47.2, 30.6, 28.9, 27.2, 22.2, 11.5, 11.3 ppm. MS (EI): m/z=27 (11), 41 (16), 53 (16), 67 (34), 81 (40), 96 (100), 109 (14), 124 (52), 137 (7), 152 (21, M$^{.+}$).

Odor description of 3,6-diethylcyclohex-2-en-1-one: green, minty, tobacco, lovage.

Example 26: Synthesis of 2,3-diethylcyclohex-2-en-1-one (41)

Synthesis as in Example 1.2, starting from ethyl-3-oxo-hexanoate and 1-penten-3-one. Column chromatographic purification on silica gel (eluent: cyclohexane/acetic acid ethyl ester 30/1) gives 2,3-diethylcyclohex-2-en-1-one as an isomer mixture in the form of a colorless oil (15%).

$^1$H-NMR (CDCl$_3$, 400 MHz): δ 2.37 (m, 2H), 2.33 (m, 2H), 2.29 (m, 2H), 2.27 (m, 2H), 1.92 (m, 2H), 1.10 (t, J=8 Hz, 3H), 0.94 ppm (t, J=8 Hz, 3H). $^{13}$C-NMR (CDCl$_3$, 100 MHz): δ 199.2, 160.0, 136.5, 38.1, 30.1, 27.7, 22.6, 18.2, 14.2, 12.5 ppm. MS (EI): m/z=27 (13), 41 (36), 55 (26), 67 (40), 81 (100), 95 (46), 109 (37), 124 (78), 137 (21), 152 (77, M$^{.+}$).

Odor description of 2,3-diethylcyclohex-2-en-1-one: tobacco, saffron, fruity, apple, damascone.

Example 27: Synthesis of 4-ethyl-2,5-dimethylcyclohex-2-en-1-one (42)

Synthesis as in Example 1.2, starting from methyl-3-oxovalerate and 2-ethylcrotonaldehyde. Column chromatographic purification on silica gel (eluent: cyclohexane/acetic acid ethyl ester 5/1) gives 4-ethyl-2,5-dimethylcyclohex-2-en-1-one as an isomer mixture in the form of a colorless oil (34%).

Main Compound:
$^1$H-NMR (CDCl$_3$, 400 MHz): δ 6.59 (m, 1H), 2.48 (m, 1H), 2.14 (m, 1H), 2.02 (m, 1H), 1.96 (m, 1H), 1.78 (m, 3H), 1.69 (m, 1H), 1.48 (m, 1H), 1.04 (d, J=6 Hz, 3H), 0.95 ppm (t, J=7 Hz, 3H). $^{13}$C-NMR (CDCl$_3$, 100 MHz): δ 200.3, 149.4, 135.1, 45.6, 44.7, 33.9, 24.6, 19.4, 15.8, 10.5 ppm. MS (EI): m/z=27 (7), 41 (31), 55 (14), 69 (55), 81 (17), 95 (100), 110 (20), 123 (18), 137 (6), 152 (9, M$^{.+}$).

Secondary Compound:
$^1$H-NMR (CDCl$_3$, 400 MHz): δ 6.56 (m, 1H), 2.37 (m, 4H), 1.78 (m, 3H), 1.47 (m, 2H), 1.00 (d, J=7 Hz, 3H), 0.90 ppm (t, J=7 Hz, 3H). $^{13}$C-NMR (CDCl$_3$, 100 MHz): δ 200.0, 148.4, 134.5, 44.8, 42.0, 32.6, 23.7, 15.8, 14.5, 11.9 ppm. MS (EI): m/z=27 (7), 41 (30), 55 (13), 69 (50), 81 (18), 95 (100), 110 (21), 123 (17), 137 (6), 152 (7, M$^{.+}$).

Odor description of 4-ethyl-2,5-dimethylcyclohex-2-en-1-one: spicy, aromatic, camphor, floral, animal.

Example 28: Synthesis of 3-ethyl-5-isopropyl-2-methylcyclohex-2-en-1-one (43)

Piperidine (7.4 g) in ethanol (20 ml) is added dropwise to a solution of methyl-3-oxovalerate (215 g, 1.36 mol) and isobutyl aldehyde (61.2 g, 0.85 mol) within 20 minutes at 0-5° C. The solution is stirred overnight at room temperature and heated for 2.5 hours under reflux. The reaction solution is then heated with ethanol (600 ml), water (350 ml) and NaOH (56 g) under reflux for 8 hours and the solvent is distilled off. At room temperature, water (500 ml) and MTBE (250 ml) are added and the aqueous phase is separated. The organic phase is neutrally washed 2× with 5% sulfuric acid and soda solution and concentrated. Fractional distillation gives 3-ethyl-5-isopropyl-2-methylcyclohex-2-en-1-one in the form of a colorless oil (156.3 g, 64%).

$^1$H-NMR (CDCl$_3$, 400 MHz): δ 2.50 (ddd, J=16, 4.2 Hz, 1H), 2.37-2.19 (m, 1H), 2.23 (m, 3H), 2.19-2.08 (m, 1H), 2.06 (dd, J=16, 14 Hz, 1H), 1.76 (dd, J=2, 1 Hz, 3H), 1.83-1.68 (m, 1H), 1.63-1.49 (m, 1H), 1.08 (t, J=8 Hz, 3H), 0.92 (d, J=7 Hz, 3H), 0.91 ppm (d, J=7 Hz, 3H). $^{13}$C-NMR (CDCl$_3$, 100 MHz): δ 200.4, 160.0, 129.8, 41.4, 40.9, 34.3, 32.0, 28.4, 19.7, 19.4, 11.7, 10.3 ppm. MS (EI): m/z=41 (30), 67 (62), 83 (19), 95 (22), 110 (100), 123 (12), 137 (28), 151 (2), 165 (8), 180 (87, M$^{.+}$).

Odor description of 3-ethyl-5-isopropyl-2-methylcyclohex-2-en-1-one: strong, quinoline, leather, green, galbanum spicy, tobacco.

Flavor description of 3-ethyl-5-isopropyl-2-methylcyclohex-2-en-1-one: chemical, medicinal, fresh, woody, herb.

Example 29: Synthesis of 3,5-diethyl-2-methylcyclohex-2-en-1-one (44)

Synthesis as in Example 28, starting from methyl-3-oxovalerate and propionaldehyde. Fractional distillation gives 3,5-diethyl-2-methylcyclohex-2-en-1-one in the form of a colorless oil (62%)

$^1$H-NMR (CDCl$_3$, 400 MHz): δ 2.52 (ddd, J=16, 4.2 Hz, 1H), 2.41-2.34 (m, 1H), 2.33-2.19 (m, 2H), 2.12-2.07 (m, 1H), 2.02 (dd, J=16, 13 Hz, 1H), 1.94-1.82 (m, 1H), 1.76 (dd, J=2, 2 Hz, 3H), 1.46-1.30 (m, 2H), 1.07 (t, J=8 Hz, 3H), 0.91 ppm (t, J=8 Hz, 3H). $^{13}$C-NMR (CDCl$_3$, 100 MHz): δ 200.0, 159.6, 130.0, 43.7, 36.6, 36.3, 28.6, 28.3, 11.7, 11.1, 10.2 ppm. MS (EI): m/z=41 (25), 53 (14), 67 (60), 82 (13), 95 (21), 110 (100), 123 (6), 137 (21), 151 (10), 166 (84, M$^{.+}$).

Odor description of 3,5-diethyl-2-methylcyclohex-2-en-1-one: spicy, leather, tobacco.

Example 30: Synthesis of 3-ethyl-2-methyl-5-n-propylcyclohex-2-en-1-one (45)

Synthesis as in Example 28, starting from methyl-3-oxovalerate and butyraldehyde. Fractional distillation gives 3-ethyl-2-methyl-5-n-propylcyclohex-2-en-1-one in the form of a colorless oil (63%)

$^1$H-NMR (CDCl$_3$, 400 MHz): δ 2.54-2.48 (m, 1H), 2.41-2.33 (m, 1H), 2.33-2.18 (m, 2H), 2.12-1.91 (m, 3H), 1.76 (t, J=2 Hz, 3H), 1.42-1.27 (m, 4H), 1.07 (t, J=8 Hz, 3H), 0.91 ppm (t, J=7 Hz, 3H). $^{13}$C-NMR (CDCl$_3$, 100 MHz): δ 200.01, 159.6, 130.0, 44.0, 38.1, 37.0, 34.3, 28.3, 19.6, 14.1, 11.7, 10.2 ppm. MS (EI): m/z=41 (26), 55 (14), 67 (53), 81 (13), 95 (17), 110 (100), 123 (8), 137 (31), 151 (4), 165 (7), 180 (68, M$^{.+}$).

Odor description of 3-ethyl-2-methyl-5-n-propylcyclohex-2-en-1-one: spicy, green, celeriac, aniseed.

Example 31: Synthesis of 2-ethyl-5-isopropylcyclohex-2-en-1-one (48)

Synthesis as in Example 1.2, starting from ethyl 2-ethyl acetoacetate and 4-methyl-2-pentenal. Column chromatographic purification on silica gel (eluent: cyclohexane/acetic acid ethyl ester 30/1) gives 2-ethyl-5-isopropylcyclohex-2-en-1-one as an isomer mixture in the form of a colorless oil (28%).

$^1$H-NMR (CDCl$_3$, 400 MHz): δ 6.70 (m, 1H), 2.53 (m, 1H), 2.39 (m, 1H), 2.20 (m, 2H), 2.16-2.04 (m, 2H), 1.83 (m, 1H), 1.57 (m, 1H), 1.00 (t, J=7 Hz, 3H), 0.92 ppm (d, J=7 Hz, 6H). $^{13}$C-NMR (CDCl$_3$, 100 MHz): δ 200.3, 143.7, 140.9, 42.4, 41.9, 32.1, 29.9, 22.2, 19.6, 19.5, 12.8 ppm. MS (EI): m/z=27 (9), 41 (22), 55 (18), 67 (31), 81 (33), 96 (100), 109 (33), 123 (31), 137 (4), 151 (5), 166 (36, M$^{.+}$).

Odor description of 2-ethyl-5-isopropylcyclohex-2-en-1-one: fruity, minty, green, spicy, sage.

Example 32: Synthesis of 2-methyl-5-n-propylcyclohex-2-en-1-one (51)

Synthesis as in Example 1.2, starting from methyl-3-oxovalerate and (E)-2-hexenal. Fractional distillation gives 2-methyl-5-n-propylcyclohex-2-en-1-one as an isomer mixture in the form of a colorless oil (30%).

$^1$H-NMR (CDCl$_3$, 400 MHz): δ 6.72 (m, 1H), 2.53 (m, 1H), 2.40 (m, 1H), 2.07 (m, 3H), 1.77 (m, 3H), 1.34 (m, 4H), 0.90 ppm (t, J=7 Hz, 3H). $^{13}$C-NMR (CDCl$_3$, 100 MHz): δ 200.3, 144.9, 135.5, 44.7, 38.1, 35.4, 32.6, 19.7, 15.8, 14.1 ppm. MS (EI): m/z=27 (7), 41 (17), 54 (26), 69 (17), 82 (100), 95 (7), 109 (20), 123 (4), 137 (1), 152 (20, M$^{.+}$).

Odor description of 2-methyl-5-n-propylcyclohex-2-en-1-one: spicy, fresh, sweet, aniseed, pepper.

Example 33: Synthesis of 2-ethyl-5-n-propylcyclohex-2-en-1-one (52)

Synthesis as in Example 1.2, starting from ethyl 2-ethyl acetoacetate and (E)-2-hexenal. Column chromatographic purification on silica gel (eluent: cyclohexane/acetic acid ethyl ester 30/1) gives 2-ethyl-5-n-propylcyclohex-2-en-1-one as an isomer mixture in the form of a colorless oil (41%).

$^1$H-NMR (CDCl$_3$, 400 MHz): δ 6.67 (m, 1H), 2.53 (m, 1H), 2.43 (m, 1H), 2.20 (m, 2H), 2.10-2.02 (m, 3H), 1.34 (m, 4H), 1.00 (t, J=7 Hz, 3H), 0.91 ppm (t, J=7 Hz, 3H). $^{13}$C-NMR (CDCl$_3$, 100 MHz): δ 199.9, 143.3, 141.0, 45.0, 38.1, 35.3, 32.6, 22.3, 19.7, 14.1, 12.9 ppm. MS (EI): m/z=27 (7), 41 (18), 55 (15), 67 (32), 81 (23), 96 (100), 109 (22), 123 (42), 137 (5), 151 (3), 166 (27, M$^{.+}$).

Odor description of 2-ethyl-5-n-propylcyclohex-2-en-1-one: aniseed, licorice, lactone, blossom.

Example 34: Synthesis of 4-ethyl-5-n-propylcyclohex-2-en-1-one (57)

Synthesis as in Example 1.2, starting from ethyl acetoacetate and 2-ethyl-2-hexenal. Column chromatographic purification on silica gel (eluent: cyclohexane/acetic acid ethyl ester 30/1) gives 4-ethyl-5-n-propylcyclohex-2-en-1-one as an isomer mixture in the form of a colorless oil (15%).

Main Compound:
$^1$H-NMR (CDCl$_3$, 400 MHz): δ 6.85 (m, 1H), 5.98 (m, 1H), 2.58 (m, 1H), 2.15 (m, 1H), 2.11 (m, 1H), 1.93 (m, 1H), 1.74-1.23 (m, 6H), 0.97 (t, J=8 Hz, 3H), 0.91 ppm (t, J=8 Hz, 3H). $^{13}$C-NMR (CDCl$_3$, 100 MHz): δ 200.2, 154.3, 128.9, 42.4, 41.8, 37.6, 35.4, 24.7, 19.5, 14.2, 10.8 ppm. MS (EI): m/z=27 (16), 41 (30), 55 (42), 68 (57), 81 (100), 95 (91), 109 (46), 123 (12), 137 (16), 166 (22, M$^{.+}$).

Secondary Compound:
$^1$H-NMR (CDCl$_3$, 400 MHz): δ 7.00 (m, 1H), 5.99 (m, 1H), 2.38-2.32 (m, 3H), 2.21-2.18 (m, 1H), 1.74-1.23 (m, 6H), 1.02 (t, J=8 Hz, 3H), 0.91 ppm (m, 3H). $^{13}$C-NMR (CDCl$_3$, 100 MHz): δ 200.2, 154.8, 128.9, 41.2, 40.7, 37.4, 32.5, 22.1, 20.0, 14.2, 12.1 ppm. MS (EI): m/z=27 (14), 41 (26), 55 (35), 67 (35), 81 (100), 95 (76), 109 (39), 124 (12), 137 (14), 166 (18, M·+).

Odor description of 4-ethyl-5-n-propylcyclohex-2-en-1-one: spicy, aniseed, aldehyde.

Example 35: Synthesis of 4-ethyl-2-methyl-5-n-propylcyclohex-2-en-1-one (60)

Synthesis as in Example 1.2, starting from ethyl acetoacetate and 2-ethyl-2-hexenal. Column chromatographic purification on silica gel (eluent: cyclohexane/acetic acid ethyl ester 30/1) gives 4-ethyl-2-methyl-5-n-propylcyclohex-2-en-1-one as an isomer mixture in the form of a colorless oil (19%).

Main Compound:
$^1$H-NMR (CDCl$_3$, 400 MHz): δ 6.58 (m, 1H), 2.59 (m, 1H), 2.13 (m, 2H), 1.88 (m, 1H), 1.77 (m, 3H), 1.65 (m, 1H), 1.51 (m, 2H), 1.25 (m, 3H), 0.95 (t, J=7 Hz, 3H), 0.90 ppm (t, J=7 Hz, 3H). $^{13}$C-NMR (CDCl$_3$, 100 MHz): δ 200.4, 149.4, 134.7, 42.7, 42.1, 38.0, 35.3, 24.8, 19.6, 15.7, 14.2, 10.8 ppm. MS (EI): m/z=27 (7), 41 (36), 55 (22), 69 (52), 81 (18), 95 (89), 109 (100), 123 (28), 137 (12), 151 (12), 180 (5, M·+).

Secondary Compound:
$^1$H-NMR (CDCl$_3$, 400 MHz): δ 6.74 (m, 1H), 2.39-2.30 (m, 3H), 2.22-2.17 (m, 1H), 1.77 (m, 3H), 1.55 (m, 1H), 1.38 (m, 1H), 1.25 (m, 4H), 1.00 (t, J=8 Hz, 3H), 0.90 ppm (t, J=7 Hz, 3H). $^{13}$C-NMR (CDCl$_3$, 100 MHz): δ 200.1, 149.7, 134.7, 41.2, 41.0, 37.8, 32.3, 22.3, 20.0, 15.9, 14.2, 12.1 ppm. MS (EI): m/z=27 (11), 41 (34), 55 (21), 69 (48), 81 (28), 95 (91), 109 (100), 123 (28), 137 (16), 151 (18), 180 (7, M·+).

Odor description of 4-ethyl-2-methyl-5-n-propylcyclohex-2-en-1-one: sweet, technical, aniseed.

Example 36: Synthesis of 2,4-diethyl-5-n-propylcyclohex-2-en-1-one (61)

Synthesis as in Example 1.2, starting from ethyl acetoacetate and 2-ethyl-2-hexenal. Column chromatographic purification on silica gel (eluent: cyclohexane/acetic acid ethyl ester 30/1) gives 2,4-diethyl-5-n-propylcyclohex-2-en-1-one as an isomer mixture in the form of a colorless oil (21%).

Main Compound:
$^1$H-NMR (CDCl$_3$, 400 MHz): δ 6.52 (m, 1H), 2.58 (m, 1H), 2.16-2.09 (m, 2H), 1.87 (m, 1H), 1.66 (m, 1H), 1.54 (m, 3H), 1.40 (m, 1H), 1.32-1.18 (m, 3H), 1.01 (t, J=8 Hz, 3H), 0.95 (t, J=8 Hz, 3H), 0.90 ppm (t, J=7 Hz, 3H). $^{13}$C-NMR (CDCl$_3$, 100 MHz): δ 199.9, 147.8, 140.3, 42.5, 42.4, 37.8, 35.3, 24.9, 22.3, 19.6, 14.2, 13.0, 10.8 ppm. MS (EI): m/z=29 (21), 41 (41), 55 (70), 67 (28), 81 (100), 95 (42), 109 (89), 123 (100), 137 (59), 151 (56), 165 (26), 194 (21, M·+).

Secondary Compound:
$^1$H-NMR (CDCl$_3$, 400 MHz): δ 6.68 (m, 1H), 2.39-2.32 (m, 3H), 2.24-2.18 (m, 3H), 1.61 (m, 1H), 1.40 (m, 2H), 1.32-1.18 (m, 3H), 1.01 (t, J=8 Hz, 3H), 1.00 (t, J=7 Hz, 3H), 0.90 ppm (t, J=7 Hz, 3H). $^{13}$C-NMR (CDCl$_3$, 100 MHz): δ 199.7, 148.1, 140.2, 41.5, 40.8, 37.6, 32.3, 22.4, 22.3, 20.0, 14.2, 13.0, 12.1 ppm. MS (EI): m/z=29 (21), 41 (41), 55 (68), 67 (28), 81 (94), 95 (38), 109 (100), 123 (100), 137 (58), 151 (51), 165 (26), 194 (19, M·+).

Odor description of 2,4-diethyl-5-n-propyl-cyclohex-2-en-1-one: spicy, fruity, aniseed, floral, fatty.

Example 36-A: Inherent Smell of Example Compounds

An expert test panel was formed in order to evaluate the inherent smell of the compounds as described in Examples 1 through 36. Additionally, a comparison example was prepared using piperitone (see known cyclohexenones above, compound (viii)). As a result, 37 samples (Smell Samples 1 through 37) were prepared, wherein Smell Samples 1 through 36 comprise a compound according to Formula (I), Smell Sample 37 is not according to the invention. Each sample was prepared by mixing 0.5 wt. % of the respective compound (Smell Samples 1 through 36: compounds corresponding to Examples 1 through 36, respectively; Smell Sample 37: compound piperitone) and 99.5 wt. % dipropylene glycol (DPG).

Each resulting Smell Sample was evaluated by the expert test panel. The results are summarized below in Table A, column "Inherent smell".

Example 37: Perfume Oil Composition (Base Mixture A)

The perfume oil indicated below can be used for perfuming various cosmetic articles.

| | |
|---|---|
| Agrumex (2-tert-butylcyclohexyl acetate) (Symrise) | 30.0 |
| Agrunitrile (2,6-dimethyl-5-heptenyl cyanide) | 1.0 |
| Aldehyde C11 undecanal 10% DPG (undec-10-enal) | 2.5 |
| Aldehyde C12 lauric (dodecanal) | 1.0 |
| Aldehyde C14 so-called (gamma-undecalactone) | 4.5 |
| Allyl cyclohexyl propionate | 1.0 |
| Allyl heptylate | 4.0 |
| Ambrocenide ® 0.1% DPG ((4aR,5R,7aS,9R)-octahydro-2,2,5,8,8,9a-hexamethyl-4H-4a) (Symrise) | 8.0 |
| Anisaldehyde | 6.0 |
| Anisyl nitrile 1% DPG | 5.0 |
| Benzaldehyde | 2.0 |
| Benzyl acetate | 40.0 |
| Benzyl salicylate | 60.0 |
| Cedar leaf oil | 0.5 |
| Cinarol (2-methyl-3-phenyl-2-propen-1-ol) | 2.0 |
| Citral FF (3,7-dimethylocta-2,6-dienal) | 1.0 |
| Citronellol 950 (3,7-dimethyl-6-octen-1-ol) | 20.0 |
| Damascenone total 10% DPG (2-(2,6,6-trimethyl-1,3-cyclohexadien-1-yl)-2E-buten-1-one) | 1.0 |
| Damascone alpha 10% DPG ((E)-1-(2,6,6-trimethyl-2-cyclohexen-1-yl)-2-buten-1-one) | 3.0 |
| Dihydromyrcenol (2,6-dimethyl-7-octen-2-ol) | 5.0 |
| Dimethyl benzyl carbinyl acetate | 4.0 |

| | |
|---|---|
| Ebanol 10% DPG (3-methyl-5-(2,2,3-trimethyl-3-cyclopenten-1-yl)-4-penten-2-ol) (Givaudan) | 3.0 |
| Ethyl methyl butyrate-2 | 1.5 |
| Ethyl vanillin (3-ethoxy-4-hydroxybenzaldehyde) | 0.5 |
| Eugenol (2-methoxy-4-allyl-phenol) | 3.0 |
| Eugenol acetate (4-allyl-2-methoxyphenyl acetate) | 1.0 |
| Galaxolide 50% IPM (4,6,6,7,8,8-hexamethyl-1,3,4,6,7,8-hexahydrocyclopenta[g]benzopyran) (International Flavors & Fragrances Inc.) | 40.0 |
| Geraniol 60 (2,6-dimethyl-trans-2,6-octadien-8-ol) | 30.0 |
| Hexyl cinnamaldehyde alpha | 120.0 |
| Indoflor ® cryst. 10% DPG (4,4a,5,9b-tetrahydroindeno[1,2-d][1,3] dioxin) (Symrise) | 2.0 |
| Iso E Super (2-acetyl-1,2,3,4,5,6,7,8-octahydro-2,3,8,8-tetramethyl-naphthalin) (International Flavors & Fragrances Inc.) | 20.0 |
| Isoamyl salicylate | 2.0 |
| Isobutyl quinoline 1% DPG | 8.5 |
| Isoraldeine 70 ((E)-3-methyl-4-(2,6,6-trimethyl-cyclohex-2-enyl)-but-3-en-2-one) (Givaudan) | 15.0 |
| Jasmaprunat (ethyl (2-methyl-1,3-dioxolan-2-yl)acetate) (Symrise) | 1.0 |
| Ligustral (2,4-dimethyl-3-cyclohexene-1-carboxaldehyde) | 3.0 |
| Lilial ® (2-methyl-3-(4-tert-butylphenyl)propanal) (Givaudan) | 20.0 |
| Linalool (3,7-dimethyl-1,6-octadien-3-ol) | 32.0 |
| Menzanate 10% DPG | 2.0 |
| Methyl anthranilate 10% DPG | 1.0 |
| Methyl capronate 10% DPG | 1.0 |
| Methylheptin carbonate 10% DPG | 3.0 |
| Mysore acetate (4,7-methano-1H-indenemethanol) | 5.0 |
| Orange oil | 20.0 |
| Oryclon ® Special (4-tert-butyl cyclohexyl acetate) (Symrise) | 60.0 |
| Phenyl ethyl acetate | 6.0 |
| Phenyl ethyl dimethyl carbinol | 10.0 |
| Rosaphen ® (beta-methyl-phenylpentanol) (Symrise) | 10.0 |
| Rose oxide inactive 10% DPG (tetrahydro-4-methyl-2-(2-methylpropenyl)-2H-pyran) | 4.0 |
| Styrene acetate | 5.0 |
| Terpineol pure | 30.0 |
| Terpinyl acetate | 5.0 |
| Vanillin (4-hydroxy-3-methoxybenzaldehyde) | 1.5 |
| Vertomugal 10% DPG (4-(4-methyl-3-penten-1-yl)-3-cyclohexencarbaldehyde) | 8.0 |
| Ylang MC base type | 10.0 |
| Ysamber ® K (1,1,5,5-tetramethylhexahydro-spiro [1,3-dioxolane-2,8(5H)-2H-2,4a-methanonaphthalene]) (Symrise) | 8.0 |
| Dipropylene glycol (DPG) | 306.0 |

The perfume oil produced was divided into two equal parts. In order to exclude dilution effects, 0.5 wt. % of dipropylene glycol (DPG), expressed in terms of the total amount of the first part of the perfume oil, was added to a first part of the perfume oil. 0.5 wt. % of 4-isopropyl-6-methylcyclohex-2-en-1-one from Example 2, expressed in terms of the total amount of the part of the perfume oil, was added to the second part of the perfume oil. The resulting compositions were olfactorily compared with one another.

The composition comprising 0.5 wt. % of 4-isopropyl-6-methylcyclohex-2-en-1-one from Example 2 was perceived as radiant and harmonic by perfumers, the floral aspects in particular being perceived as accentuated. A pleasant fresh feeling was also perceived.

Example 37-A: Perfume Oil Composition (Base Mixture B)

The perfume oil indicated below can be used for perfuming various cosmetic articles.

| | |
|---|---|
| Agrumex (2-tert-butylcyclohexyl acetate) (Symrise) | 320.0 |
| Aldehyde C14 so-called (gamma-undecalactone) | 7.5 |
| Allyl heptylate | 75.0 |
| Benzyl acetate | 5.5 |
| Citral FF (3,7-dimethylocta-2,6-dienal) | 5.5 |
| Cyclogalbanat (Allyl-(cyclohexyloxy)acetate) (Symrise) | 45.0 |
| Damascon alpha ((E)-1-(2,6,6-trimethyl-2-cyclohexen-1-yl)-2-buten-1-one) | 15.0 |
| Dynascone (1-(5,5-dimethyl-1-cyclohexen-1-yl)pent-4-en-1-one) (Firmenich) | 15.0 |
| Herbyl propionate | 35.0 |
| Hexenol cis-3 | 7.5 |
| Hexenol trans-2 | 5.5 |
| Hexenyl acetate cis-3 | 25.0 |
| Hexyl acetate | 100.0 |
| Isobornyl acetate | 20.0 |
| Manzanate (Ethyl-2-methyl valerate) (Givaudan) | 15.0 |
| Orange oil | 52.5 |
| Pinen alpha laevo nat. | 45.0 |
| Pinen beta nat. | 100.0 |
| Stemone (5-methylheptan-3-onoxim) (Givaudan) | 45.0 |
| Styrolyl acetate | 45.0 |
| Undecavertol | 1.0 |
| Vertocitral (2,4-dimethylcyclohex-3-en-1-carbaldehyde) (Symrise) | 15.0 |

Example 37-B: Inherent Smell of Base Mixture A and Base Mixture B

An odor description was carried out by an expert test panel in order to determine the inherent smell of Base mixture A and Base mixture B.

Prior to the odor description of Base mixture A and Base mixture B a Resulting Mixture A and Resulting Mixture B was prepared by mixing:

99.5 wt. % Base mixture A (respectively Base mixture B) and 0.5 wt. % dipropylene glycol (DPG) to prepare Resulting Mixture A and Resulting Mixture B, respectively.

After mixing, the Resulting Mixtures A and B were evaluated by the expert test panel:

Resulting Mixture A was described as: floral, white blossom, fresh,

Resulting Mixture B was described as: fruity, apple, natural.

Example 37-C: Odor Description of Base Mixtures A and B in Combination with Compounds of Formula (I)

In Example 36-A the inherent smell of the compounds according to Examples 1 through 36 is described. In order to analyze the effect of these compounds in perfume oil compositions a set of 74 additional samples was prepared. The set comprises the following samples:

Resulting Mixture A1 through Resulting Mixture A37

Resulting Mixture B1 through Resulting Mixture B37

Resulting Mixtures A1 through Resulting Mixtures A36 were prepared by mixing:

99.5 wt. % Base mixture A and 0.5 wt. % of the respective compound as described in Examples 1 through 36.

Resulting Mixture A37 was Prepared by Mixing:

99.5 wt. % Base mixture A and 0.5 wt. % of piperitone, thus Resulting Mixture A37 is a comparison sample not according to the invention.

Resulting Mixtures B1 through Resulting Mixtures B36 were prepared by mixing:

99.5 wt. % Base mixture B and 0.5 wt. % of the respective compound as described in Examples 1 through 36.

Resulting Mixture B37 was Prepared by Mixing:

99.5 wt. % Base mixture B and 0.5 wt. % of piperitone, thus Resulting Mixture B37 is a comparison sample not according to the invention.

The numbers 1 through 36 of the Resulting Mixtures correspond to the numbers of the above Examples 1 through 36.

Each of the 74 additional samples was evaluated by the expert test panel. The results are summarized below in Table A, columns "Effect in Base mixture A" and "Effect in Base mixture B".

TABLE A

| Compound (with reference to the example numbers above) | Inherent smell (0.5 wt. % compound and 99.5 wt. % DPG) | Effect in Base mixture A (0.5 wt. % compound and 99.5 wt. % Base mixture A) | Effect in Base mixture B (0.5 wt. % compound and 99.5 wt. % Base mixture B) |
|---|---|---|---|
| (1) Example 1 | fruity, grapefruit | ++ | + |
| (2) Example 2 | fresh, grapefruit | ++ | ++ |
| (3) Example 3 | spicy, cumin | + | + |
| (4) Example 4 | fruity, spicy | ++ | ++ |
| (5) Example 5 | fatty, almond | ++ | + |
| (8) Example 6 | fatty, coumarin | ++ | ++ |
| (9) Example 7 | spicy, aromatic | ++ | ++ |
| (10) Example 8 | aromatic | + | + |
| (12) Example 9 | spicy, saffron | ++ | ++ |
| (13) Example 10 | green, fatty | ++ | ++ |
| (14) Example 11 | spicy, saffron | ++ | + |
| (15) Example 12 | fruity, almond | + | + |
| (18) Example 13 | aromatic, almond | + | + |
| (19) Example 14 | spicy, saffron | + | + |
| (23) Example 15 | spicy, saffron | ++ | ++ |
| (24) Example 16 | fresh, spicy | + | ++ |
| (28) Example 17 | spicy, saffron | + | ++ |
| (29) Example 18 | weak spicy | ++ | ++ |
| (30) Example 19 | spicy, saffron | + | + |
| (31) Example 20 | green, fatty | + | + |
| (32) Example 21 | spicy, caraway | ++ | ++ |
| (33) Example 22 | spicy, caraway | ++ | + |
| (34) Example 23 | spicy, coumarin | ++ | ++ |
| (37) Example 24 | weak fatty | + | + |
| (40) Example 25 | green, spicy | ++ | + |
| (41) Example 26 | spicy, fruity | + | ++ |
| (42) Example 27 | aromatic, spicy | + | ++ |
| (43) Example 28 | green, spicy | ++ | ++ |
| (44) Example 29 | spicy | + | + |
| (45) Example 30 | spicy, aniseed | ++ | + |
| (48) Example 31 | fruity, green | + | + |
| (51) Example 32 | spicy, aniseed | ++ | ++ |
| (52) Example 33 | spicy, fatty | + | + |
| (57) Example 34 | spicy, aniseed | ++ | ++ |
| (60) Example 35 | spicy | + | + |
| (61) Example 36 | fruity, fatty | ++ | ++ |
| (viii) piperitone | spearmint, herbal | − | ± |

The columns in Table A have the following meaning:

"Compound": In this column the number within the brackets refers to the number of the used compound as used throughout the specification. The term "Ex." means "Example" and refers to the above mentioned example number. Compound (viii), piperitone is a known cyclohexenone, which is not a compound of Formula (I) and, thus, serves as comparison sample.

"Inherent smell": In this column the inherent smell of each compound is reported. Each sample was prepared as described in Example 36-A, thus, corresponding to Smell Samples 1 through 37.

"Effect in Base mixture A": In this column the effect on the odor description of Base mixture A is reported due to the presence of 0.5 wt. % of the respective compound in said Base mixture. The odor description of Base mixture A was described as floral, white blossom, fresh.

"Effect in Base mixture B": In this column the effect on the odor description of Base mixture B is reported due to the presence of 0.5 wt. % of the respective compound in said Base mixture. The odor description of Base mixture B was described as fruity, apple, natural.

"Effect" means: (i) enhancement of the odor description of the respective Base mixture or (ii) no difference in the odor description of the respective Base mixture or (iii) reduction of the odor description of the respective Base mixture. The effects are categorized as follows:

"++" Odor description is very strongly enhanced, i.e. the enhancement is strongly super additive (much more than the sum of inherent smell of the respective compound and the odor description of the respective Base mixture)

"+" Odor description is strongly enhanced, i.e. the enhancement is super additive (more than the sum of inherent smell of the respective compound and the odor description of the respective Base mixture)

"±" no difference in the odor description (i.e. no effect on the odor description of the respective Base mixture)

"−" reduction of the odor description of the respective Base mixture

Result: Compounds of Examples 1 through 36, which are compounds of Formula (I), in each case super additively enhance the floral and/or fruity odor of Base mixture A and Base mixture B, respectively. Our experiments have shown that it is not the inherent smell of the compounds of Examples 1 through 36 causing this effect. Comparison compound piperitone did not cause such an effect.

Example 38: Perfume Oil Composition

The perfume oil indicated below can be used for perfuming various cosmetic products.

| | |
|---|---|
| Aldehyde C14 so-called (gamma-undecalactone) | 2.0 |
| Amarocit ® (6,6-dimethoxy-2,5,5-trimethylhex-2-ene) (Symrise) | 3.0 |
| Anethol supra (4-propenylanisol) | 1.0 |
| Apriconia base | 10.0 |
| Benzoe Siam resin 20% BB | 4.0 |
| Benzyl acetate | 1.0 |
| Calone 1951 10% DPG (7-methyl-2H-1,5-benzodioxepin-3(4H)-one) (Danisco Seillans S.A.) | 1.0 |
| Canthoxal [3-(4-methoxyphenyl)-2-methylpropanal] | 10.0 |
| Citronellol 950 (3,7-dimethyl-6-octen-1-ol) | 6.0 |
| Coumarin (2H-1-benzopyran-2-one) | 17.0 |
| Damascenone total 10% DPG (2-(2,6,6-trimethyl-1,3-cyclohexadien-1-yl)-2E-buten-1-one) | 6.0 |
| Damascene alpha 10% DPG ((E)-1-(2,6,6-trimethyl-2-cyclohexen-1-yl)-2-buten-1-one) | 4.0 |
| Decalactone gamma | 2.0 |
| Dihydrojasmone 10% DPG (2-pentyl-3-methyl-2-cyclopenten-1-one) | 0.5 |
| Ethylene brassylate (1,4-dioxacycloheptadecan-5,17-dione) | 100.0 |
| Ethyl linalool [(6E)-3,7-dimethylnona-1,6-dien-3-ol] | 45.0 |
| Ethyl maltol 10% DPG (2-ethyl-3-hydroxy-4H-pyran-4-one) | 2.0 |
| Ethyl vanillin (3-ethoxy-4-hydroxybenzaldehyde) | 3.0 |
| Florhydral 10% DPG (3-(3-isopropylphenyl)butanal) (Givaudan) | 4.0 |
| Florosa ® (4-methyl-2-(2-methylpropyl)tetrahydro-2H-4-pyranol) | 45.0 |
| Geraniol 60 2,6-dimethyl-trans-2,6-octadien-8-ol | 2.0 |
| Globalide ® (oxacyclohexadec-12-en-2-one) (Symrise) | 60.0 |
| Globanone ® (cyclohexadec-8-en-1-one) (Symrise) | 40.0 |
| Grapefruit oil | 5.0 |
| Hedion ® (methyl dihydrojasmonate) (Firmenich) | 77.5 |
| Hexyl salicylate cis-3 | 15.0 |
| Hydroxycitronellal | 15.0 |
| Iso E Super (2-acetyl-1,2,3,4,5,6,7,8-octahydro-2,3,8,8-tetramethyl-naphthalin) (International Flavors & Fragrances Inc.) | 170.0 |
| Leafovert ® 10% DPG (cis-hex-3-en-1-yl-methyl carbonate) | 7.0 |
| Lilial ® (2-methyl-3-(4-tert-butylphenyl)propanal) (Givaudan) | 50.0 |
| Macrolide ® supra (15-cyclopentadecanolide) | 60.0 |
| Mandarin oil | 5.0 |
| Phenyl ethyl alcohol 10% DPG | 2.0 |
| Polysantol (3,3-dimethyl-5-(2',2',3'-trimethyl-3'-cyclopenten-1'-yl)-4-penten-2-ol) (Firmenich) | 4.0 |
| *Prunella* base type | 10.0 |
| Rose oxide high cis 1% DPG (tetrahydro-4-methyl-2-(2-methylpropenyl)-2H-pyran) | 5.0 |
| Sandalore [5-(2,2,3-trimethyl-3-cyclopentenyl)-3-methylpentan-2-ol] (Givaudan) | 5.0 |
| Synambran ® R 50% IMP [3a,6,6,9a-tetramethyldodecahydronaphtho[2,1-B]Furan] (Symrise) | 8.0 |
| Timberol ® (1-(2,2,6-trimethylcyclohexyl)hexan-3-ol) | 3.0 |
| Vanillin (4-hydroxy-3-methoxybenzaldehyde) | 15.0 |
| DPG | 55.0 |

The perfume oil produced was divided into two equal parts. In order to exclude dilution effects, 1.0 wt. % of dipropylene glycol (DPG) expressed in terms of the total amount of the first part of the perfume oil, was added to a first part of the perfume oil. 1.0 wt. % of ethyl-2,5-dimethylcyclohex-2-en-1-one from Example 10, expressed in terms of the total amount of the part of the perfume oil, was added to the second part of the perfume oil. The resulting compositions were olfactorily compared with one another.

The addition of 1.0 wt. % of 3-ethyl-2,5-dimethylcyclohex-2-en-1-one from Example 10 imparts in particular a lasting impression to the head notes of the composition. An unexpected fruitiness in the direction of peach was implied. The composition was thus more natural and tangier, and the overall effect was therefore more rounded.

Example 39: Perfume Oil Composition

The perfume oil indicated below can be used for perfuming various cosmetic products.

| | |
|---|---|
| Aldehyde C11 undecanal (undec-10-enal) | 4.0 |
| Aldehyde C12 MNA (2-methylundecanal) | 6.0 |
| Aldehyde C18 so-called (5-pentyldihydrofuran-2(3H)-one) | 1.5 |
| Allyl amyl glycolate | 1.5 |
| Allyl capronate | 0.5 |
| Ambrettolide (oxacycloheptadec-10-en-2-one) | 2.0 |
| Ambroxide (dodecahydro-3a,6,6,9a-tetramethyl naphtho-(2,1-b)furan) (Symrise) | 1.5 |
| Amyl salicylate | 31.5 |
| Anethol supra (4-propenyl-anisol) | 3.0 |
| Anisaldehyde | 24.5 |
| Benzyl alcohol | 1.5 |
| Benzyl benzoate | 0.5 |
| Caryophyllene, rect. 10% DPG | 8.0 |
| Coumarin (2H-1-benzopyran-2-one) | 48.0 |
| Damascone alpha ((E)-1-(2,6,6-trimethyl-2-cyclohexen-1-yl)-2- | 0.5 |
| Dimethyl benzyl carbinyl butyrate | 6.0 |
| Dipentene | 4.0 |
| Diphenyl oxide | 0.5 |
| *Eucalyptus* oil | 1.5 |
| Frambinon ® (4-(4-methoxyphenyl)butan-2-one) (Symrise) | 1.0 |
| Geraniol supra 2,6-dimethyl-trans-2,6-octadien-8-ol | 6.5 |
| Geranyl acetate (3,7-dimethyl-2,6-octadiene acetate) | 1.0 |

-continued

| | |
|---|---|
| Globalide ® (oxacyclohexadec-12-en-2-one) (Symrise) | 14.5 |
| Guaiyl acetate | 0.5 |
| Hedion ® (methyl dihydrojasmonate) (Firmenich) | 51.0 |
| Heliotropin (3,4-(methylenedioxy)-benzaldehyde) | 8.5 |
| Hexyl salicylate | 156.0 |
| Ionol (2,6-di-tert-butyl-4-methylphenol) | 4.0 |
| Ionone beta ((E)-4-(2,6,6-trimethyl-1-cyclohexen-1-yl)-3-buten-2- | 71.0 |
| Iso E Super (2-acetyl-1,2,3,4,5,6,7,8-octahydro-2,3,8,8-tetramethylnaphthalin) (International Flavors & Fragrances Inc.) | 92.0 |
| Isoraldeine 70 ((E)-3-methyl-4-(2,6,6-trimethyl-cyclohex-2-enyl)-but-3-en-2-one) (Givaudan) | 30.0 |
| Lilial ® (2-methyl-3-(4-tert-butylphenyl)propanal) (Givaudan) | 92.0 |
| Linalool (3,7-dimethyl-1,6-octadien-3-ol) | 69.0 |
| Linalyl acetate (1,5-dimethyl-1-vinyl-4-hexenyl acetate) | 4.5 |
| Nerol (2,6-dimethyl-2,6-octadien-8-ol) | 2.5 |

-continued

| | |
|---|---|
| Ocimene | 0.5 |
| Orange oil | 68.0 |
| Oryclon ® Special (4-tert-butylcyclohexyl acetate) (Symrise) | 119.0 |
| Patchouli oil | 9.5 |
| Polysantol (3,3-dimethyl-5-(2',2',3'-trimethyl-3'-cyclopenten-1'-yl)-4-penten-2-ol) (Firmenich) | 1.0 |
| Sandranol ® ((2E)-2-ethyl-4-(2,2,3)-trimethylcyclopent-3-en-1-yl)but-2-en-1-ol) (Symrise) | 10.0 |
| Styrene acetate | 14.5 |
| Terpineol alpha | 14.0 |
| Tetrahydrolinalool (3,7-dimethyloctan-3-ol) | 0.5 |
| Undecanon-2 10% DPG | 2.0 |
| Vanillin (4-hydroxy-3-methoxybenzaldehyd) | 10.5 |

The perfume oil produced was divided into two equal parts. In order to exclude dilution effects, 2.0 wt. % of dipropylene glycol (DPG) expressed in terms of the total amount of the first part of the perfume oil, were added to a first part of the perfume oil. 2.0 wt. % of 2,3,4,5-tetramethylcyclohex-2-en-1-one from Example 15, expressed in terms of the total amount of the part of the perfume oil, were added to the second part of the perfume oil. The resulting compositions were olfactorily compared with one another.

The addition of 2.0 wt. % of 2,3,4,5-tetramethylcyclohex-2-en-1-one from Example 15 led to an unexpected fresh floral harmony, together with a pleasant fruitiness. The composition therefore obtained more radiance and fullness.

Example 40: Perfume Oil Composition

The perfume oil indicated below can be used for perfuming various cosmetic products.

| | |
|---|---|
| Ambrocenide ® 0.1% DPG ((4aR,5R,7aS,9R)-octahydro-2,2,5,8,8,9a-hexamethyl-4H-4a) (Symrise) | 20.0 |
| Ambroxide (dodecahydro-3a,6,6,9a-tetramethylnaphtho(2,1-b)furan) (Symrise) | 5.0 |
| Aurelione (cyclohexadec-8-en-1-one) (Symrise) | 120.0 |
| Mugwort oil | 10.0 |
| Bergamot base | 80.0 |
| Cedramber | 20.0 |
| *Cistus* oil 10% DPG | 10.0 |
| Citron oil | 20.0 |
| Coumarin (2H-1-benzopyran-2-one) | 20.0 |
| Cyclogalbanat ® 10% DPG | 5.0 |
| Dihydromyrcenol (2,6-dimethyl-7-octen-2-ol) | 60.0 |
| Ebanol (3-methyl-5-(2,2,3-trimethyl-3-cyclopenten-1-yl)-4-penten-2-ol) (Givaudan) | 15.0 |
| Evernyl ® (3-methoxy-5-methylphenol) (Givaudan) | 5.0 |
| Galbanum oil 10% DPG | 15.0 |
| *Geranium* base | 20.0 |
| Globalide ® (oxacyclohexadec-12-en-2-one) (Symrise) | 60.0 |
| Hedion ® (methyl dihydrojasmonate) (Firmenich) | 30.0 |
| Hexyl cinnamaldehyde alpha | 40.0 |
| Iso E Super (2-acetyl-1,2,3,4,5,6,7,8-octahydro-2,3,8,8-tetramethyl-naphthalin) (International Flavors & Fragrances Inc.) | 150.0 |
| Isoraldeine 70 ((E)-3-methyl-4-(2,6,6-trimethyl-cyclohex-2-enyl)-but-3-en-2-one) (Givaudan) | 20.0 |
| Spearmint oil 10% DPG | 10.0 |
| Lavandin oil grosso | 30.0 |
| Lilial ® (2-methyl-3-(4-tert-butylphenyl)propanal) (Givaudan) | 30.0 |
| Linalool (3,7-dimethyl-1,6-octadien-3-ol) | 20.0 |
| Linalyl acetate (1,5-dimethyl-1-vinyl-4-hexenyl acetate) | 30.0 |
| Lyral ® 4-(4-hydroxy-4-methylpentyl)-3-cyclohexenecarboxaldehyde | 40.0 |
| Mandarin oil | 5.0 |
| Clove blossom oil | 10.0 |
| Patchouli oil | 79.5 |
| Vanillin (4-Hydroxy-3-methoxybenzaldehyde) | 20.0 |

The perfume oil produced was divided into two equal parts. In order to exclude dilution effects, 0.5 wt. % of dipropylene glycol (DPG) expressed in terms of the total amount of the first part of the perfume oil, was added to a first part of the perfume oil. 0.5 wt. % of 2,3,5,5-tetramethylcyclohex-2-en-1-one from Example 18, expressed in terms of the total amount of the part of the perfume oil, was added to the second part of the perfume oil. The resulting compositions were olfactorily compared with one another.

The addition of 0.5 wt. % of 2,3,5,5-tetramethylcyclohex-2-en-1-one from Example 18 imparts a surprising fresh character to the composition. Furthermore, the head notes, in particular the floral and fruity aspects, were enhanced to a particular extent, so that the composition gains more expression and eloquence.

Example 41: Perfume Oil Composition

The perfume oil indicated below can be used for perfuming various cosmetic products.

| | |
|---|---|
| Agrumex (2-tert-butylcyclohexyl acetate) (Symrise) | 40.0 |
| Aldehyde C8 octanal | 10.0 |
| Ambrocenide ® 10% DPG ((4aR,5R,7aS,9R)-octahydro-2,2,5,8,8,9a-hexa-methyl-4H-4a) (Symrise) | 5.0 |
| Damascone alpha 1% DPG ((E)-1-(2,6,6-trimethyl-2-cyclohexen-1-yl)-2-buten-1-one) | 20.0 |
| Dihydromyrcenol (2,6-dimethyl-7-octen-2-ol) | 80.0 |
| Dimethyl benzyl carbinyl acetate | 15.0 |
| Hedion ® (methyl dihydrojasmonate) (Firmenich) | 30.0 |
| Herbaflorate (4,7-methano-3a,4,5,6,7,7a-hexahydro-5-indenyl acetate and/or 4,7-methano-3a,4,5,6,7,7a-hexahydro-6-indenyl acetate) (Symrise) | 80.0 |
| Herbyl propionate | 40.0 |
| Hexyl salicylate | 100.0 |
| Hexyl cinnamaldehyde alpha | 78.0 |
| Helvetolide ® (2-[1-(3,3-dimethyl-cyclohexyl)ethoxy]-2-methyl-1-propanol propanoate (Firmenich) | 10.0 |
| Iso E Super (2-acetyl-1,2,3,4,5,6,7,8-octahydro-2,3,8,8-tetramethyl-naphthalin) (International Flavors & Fragrances Inc.) | 120.0 |
| Isoraldeine 70 ((E)-3-methyl-4-(2,6,6-trimethyl-cyclohex-2-enyl)-but-3-en-2-one) (Givaudan) | 50.0 |
| Majantol ® (2,2-dimethyl-3-(3-methylphenyl)propanol) | 50.0 |
| Nerolione ® [1-(3-methyl-2-benzofuran-1-yl)ethanone] | 5.0 |
| Oryclon ® Special (4-tert-butylcyclohexyl acetate) (Symrise) | 100.0 |
| Patchouli oil | 50.0 |
| Phenyl ethyl alcohol | 35.0 |
| Phenoxanol (3-methyl-5-phenylpentan-1-ol) | 20.0 |
| Symrose ® | 50.0 |
| Undecavertol | 10.0 |

The perfume oil produced was divided into two equal parts. In order to exclude dilution effects, 2.0 wt. % of dipropylene glycol (DPG) expressed in terms of the total amount of the first part of the perfume oil, were added to a first part of the perfume oil. 2.0 wt. % of 3-ethyl-5-isopropyl-2-methylcyclohex-2-en-1-one from Example 28, expressed in terms of the total amount of the part of the perfume oil, were added to the second part of the perfume oil. The resulting compositions were olfactorily compared with one another.

After addition of 2.0 wt. % of 3-ethyl-5-isopropyl-2-methylcyclohex-2-en-1-one from Example 28, flowery notes in particular were intensified. The composition furthermore develops a rosy harmony and is associated overall with a fresh naturalness and stimulating sensibility.

Example 42: Deodorant Spray

| Ingredients | wt. % |
|---|---|
| Ethyl alcohol 96% | 48.75 |
| Deolite (dimethylphenylpropanol, 1,5-pentanediol) (Symrise) | 0.25 |
| Propellant 2.7 bar | 50.00 |
| Perfume oil composition from Example 38 | 1.00 |

The fragrance of the deodorant spray itself, and the odor perceptible in the vicinity of the armpit after use thereof, showed a significant fruity aspect, the overall impression having been found to be radiant, natural and harmonic.

Example 43: Deodorant Stick

| Ingredients | wt. % |
|---|---|
| Sodium stearate | 6.5 |
| Deolite (dimethylphenylpropanol, 1,5-pentanediol) (Symrise) | 0.5 |
| Ethyl alcohol 96% | 74.3 |
| Glycerine | 10.0 |
| PPG-3 mystyl ether | 7.7 |
| Perfume oil composition from Example 39 | 1.0 |

Example 44: Deodorant Roll-on with Alcohol and Symdeo

| Ingredients | wt. % |
|---|---|
| Propan-1,2-diol | 7.00 |
| Ethyl alcohol 96% | 50.00 |
| Ultrathix P 100 (acrylic acid/VP crosspolymer) (ISP Global Technologies) | 0.60 |
| Deionized water | 39.35 |
| Symdeo MPP | 0.50 |
| EDTA-Na4 | 0.05 |
| Sodium hydroxide solution, 10% | 0.50 |
| Cremophor CO 40 | 1.00 |
| Perfume oil composition from Example 40 | 1.00 |

Example 45: Shampoo

| Ingredients | wt. % |
|---|---|
| Water | 71.9 |
| Plantacare PS 10 (sodium lauryl sulfate, lauryl glucoside) (Cognis) | 20.0 |
| Euperlan PK 771 (glycol distearate, sodium lauryl sulfate, cocamide MEA, laureth-10) (Cognis) | 6.0 |
| Preservative | 0.5 |
| Sodium chloride | 1.4 |
| Citric acid | 0.1 |
| Perfume oil composition from Example 41 | 0.1 |

Example 46: Shower Gel

| Ingredients | wt. % |
| --- | --- |
| Water | 77.436 |
| Plantacare PS 10 (sodium lauryl sulfate, lauryl glucoside) (Cognis) | 20.000 |
| Phenoxyethanol | 0.500 |
| Sodium chloride | 1.400 |
| Citric acid | 0.164 |
| Perfume oil composition from Example 38 | 0.500 |

Example 47: Face Cream O/W

| Ingredients | wt. % |
| --- | --- |
| Phase A | |
| Dracorin 100 S.E.P. (glyceryl stearate, PEG-100 stearate) (Symrise) | 2.5 |
| Glyceryl stearate | 2.0 |
| Cetearyl alcohol | 2.0 |
| Dragoxat 89 (ethyl hexyl isononanoate) (Symrise) | 3.0 |
| Mineral oil | 3.0 |
| Neutral oil (capryl/capric acid triglyceride) | 4.0 |
| Abil 350 (dimethicone) (Degussa-Goldschmidt) | 0.5 |
| Tocopheryl acetate | 0.3 |
| Phase B | |
| Deionized water | 77.7 |
| Keltrol RD (xanthan gum) (CP-Kelko) | 0.1 |
| Carbopol Ultrez-10 (carbomer) (B F Goodrich, Belgium) | 0.1 |
| Glycerine | 3.0 |
| Dragocid liquid (phenoxyethanol, methyl parabene, ethyl parabene, butyl parabene, propyl parabene, isobutyl parabene) (Symrise) | 0.8 |
| Phase C | |
| Sodium hydroxide solution, 10% | 0.2 |
| Phase D | |
| Dragoderm (glycerine, *Triticum vulgare* gluten, water) (Symrise) | 0.5 |
| Phase E | |
| Perfume oil composition from Example 39 | 0.3 |

Example 48: Anti-Aging Face Cream O/W, LSF 15

| Ingredients | wt. % |
| --- | --- |
| Phase A | |
| Dracorin CE (glyceryl stearate citrate) (Symrise) | 3.50 |
| Glyceryl stearate | 1.50 |
| Cetyl alcohol | 2.00 |
| Softisan 100 (hydrogenated cocoa glycerides) (Clariant GmbH) | 1.00 |
| Dragoxat 89 (ethyl hexyl isononanoate) (Symrise) | 2.00 |
| Cocoa butter | 1.00 |
| Neo Heliopan 357 (butylmethoxybenzoylmethane) (Symrise) | 1.50 |
| Neo Heliopan 303 (octocrylene) (Symrise) | 7.50 |
| Neo Heliopan OS (ethyl hexyl salicylate) (Symrise) | 5.00 |
| Tocopheryl acetate | 0.50 |
| Xiameter PMX-0245 cyclosiloxane (cyclopentasiloxane) (Dow Corning) | 1.00 |
| Disodium EDTA | 0.10 |
| Dragosantol 100 (bisabolol) (Symrise) | 0.10 |
| Tocopherol | 0.10 |
| Keltrol CG-T (xanthan gum) (CP-Kelko) | 0.25 |
| Carbopol ETD 2050 (carbomer) (Noveon) | 0.10 |
| Phase B | |

-continued

| Ingredients | wt. % |
| --- | --- |
| Deionized water | 62.92 |
| Neo Heliopan AP, neutralized with triethanolamine (disodium phenyl dibenzimidazol tetrasulfonate) (Symrise) | 1.36 |
| Actipone amla (amalki) fruit GW (glycerine, water, *Phyllanthus emblica* fruit extract) (Symrise) | 1.00 |
| Glycerine | 3.50 |
| Panthenol | 0.50 |
| Preservative | 0.80 |
| Triethanolamine | 0.40 |
| Phase C | |
| DragoBetaGlucan (water, butylene glycol, glycerine, oat grain extract) (Symrise) | 1.00 |
| DragoCalm (water, glycerine, oat grain extract) (Symrise) | 0.50 |
| Color I | 0.32 |
| Color II | 0.25 |
| Perfume oil composition from Example 37 | 0.30 |

Example 49: Body Lotion O/W

| Ingredients | wt. % |
| --- | --- |
| Phase A | |
| Dracorin GOC (glycerine oleate citrate, capryl/capric acid triglyceride) (Symrise) | 1.50 |
| Shea butter | 2.00 |
| Dracorin CE (glyceryl stearate citrate) (Cognis) | 1.00 |
| Glyceryl stearate | 3.00 |
| Sweet almond oil | 7.00 |
| Isopropyl myristate | 3.00 |
| Phase B | |
| Biotive D-(+)-trehalose (Symrise) | 0.10 |
| Deionized water | 77.85 |
| Amaze" XT (dehydroxanthan gum) (National Starch & Chemical) | 0.40 |
| Glycerine | 1.50 |
| Sodium benzoate | 0.25 |
| Potassium sorbate | 0.25 |
| Phase C | |
| SymMatrix (maltodextrin, blackberry leaf extract) (Symrise) | 0.30 |
| Symrelief (bisabolol, ginger root extract) (Symrise) | 0.10 |
| Extrapone Aloe vera GW (water, glycerine, *Aloe vera*) (Symrise) | 1.00 |
| Phase D | |
| Citric acid | 0.25 |
| Phase E | |
| Perfume oil composition from Example 40 | 0.50 |

Example 50: Hand and Body Cream O/W, Hot-Cold Processing

| Ingredients | wt. % |
| --- | --- |
| Phase A | |
| Dracorin GOC (glycerine oleate citrate, capryl/capric acid triglyceride) (Symrise) | 2.00 |
| PCL solid (stearyl heptanoate, stearyl caprylate) (Symrise) | 2.50 |
| Cetearyl alcohol | 1.50 |
| Glyceryl stearate | 1.00 |
| Dragoxat 89 (ethyl hexyl isononanoate) (Symrise) | 3.00 |

-continued

| Ingredients | wt. % |
|---|---|
| PCL Liquid 100 (cetearyl ethyl hexanoate) (Symrise) | 7.00 |
| Isodragol (triisononanoin) (Symrise) | 4.00 |
| Dow Corning 345 Fluid (cyclomethicone) (Dow Corning GmbH) | 0.50 |
| Phase B | |
| Deionized water | 72.10 |
| Carbopol Ultrez 21 (acrylate/C10-30 alkyl acrylate crosspolymer) (Noveon) | 0.20 |
| Keltrol CG-T (xanthan gum) (CP-Kelko) | 0.10 |
| Glycerine | 3.00 |
| DragoBetaGlucan (water, butylene glycol, glycerine, oat grain extract) (Symrise) | 1.50 |
| Potassium sorbate | 0.10 |
| Dragocid liquid (phenoxyethanol, methyl parabene, ethyl parabene, butyl parabene, propyl parabene, isobutyl parabene) (Symrise) | 0.80 |
| Phase C | |
| Sodium hydroxide solution, 10% | 0.50 |
| Perfume oil composition from Example 38 | 0.20 |

Example 51: Hair Coloration, Creambase Blond with Ammonia

| Ingredients | wt. % |
|---|---|
| Phase A | |
| Oxo wax (cetyl alcohol, oleyl alcohol, cetearyl alcohol, stearic acid) (LCW) | 21.0 |
| Ceteareth-25 | 4.0 |
| Laureth-8 | 10.0 |
| Sodium cetearyl sulfate | 1.0 |
| Polyquaternium-6 (LCW) | 4.0 |
| Water | 49.3 |
| Phase B | |
| Ammonia | 10.2 |
| Phase C | |
| Perfume oil composition from Example 39 | 0.5 |

Example 52: Hair Conditioner (Rinse)

| Ingredients | wt. % |
|---|---|
| Phase A | |
| Cetearyl alcohol | 2.5 |
| Glyceryl stearate | 3.0 |
| Cutina HR Powder (hydrogenated castor oil) (Cognis) | 0.5 |
| Genamin KDM-P (behentrimonium chloride) (Clariant) | 2.0 |
| PCL-Liquid 100 (cetearyl ethyl hexanoate) (Symrise) | 0.5 |
| Phase B | |
| Deionized water | 86.7 |
| Preservative | 0.8 |
| Phase C | |
| Dragoderm (glycerine, *Triticum vulgare* gluten, water) (Symrise) | 3.5 |
| Phase D | |
| Perfume oil composition from Example 41 | 0.5 |

Example 53: Hair Conditioner (Leave-on)

| Ingredients | wt. % |
|---|---|
| Phase A | |
| Cetearyl alcohol | 3.50 |
| Cetrimonium chloride | 4.00 |
| PEG-15 cocopolyamine | 3.00 |
| Phase B | |
| Deionized water | 81.40 |
| Extrapone henna (water, propylene glycol, henna leaf extract, glucose) (Symrise) | 1.00 |
| Extrapone jojoba (water, propylene glycol, PEG-40 hydrogenated castor oil, 1,2-hexanediol, capryl glycol, jojoba seed oil) (Symrise) | 1.50 |
| *Aloe vera* gel concentrate 10/1 (*Aloe barbadensis* leaf juice) (Symrise) | 0.50 |
| Panthenol | 1.00 |
| Dragocid liquid (phenoxyethanol, methyl parabene, ethyl parabene, butyl parabene, propyl parabene, isobutyl parabene) (Symrise) | 0.80 |
| Desamido collagen | 1.00 |
| Sodium chloride | 2.00 |
| Phase C | |
| Perfume oil composition from Example 39 | 0.30 |

Example 54: Sunscreen O/W "Waterproof" with Wideband UVA Protection UVA/UVB Balance

| Ingredients | wt. % |
|---|---|
| Phase A | |
| Emulsiphos (potassium cetyl phosphate, hydrogenated palm glycerides) (Symrise) | 3.50 |
| Cetearyl alcohol | 1.00 |
| Neo Heliopan HMS (homosalate) (Symrise) | 5.00 |
| Neo Heliopan 303 (octocrylene) (Symrise) | 10.00 |
| Neo Heliopan OS (ethyl hexyl salicylate) (Symrise) | 5.00 |
| Neo Heliopan 357 (butyl methoxy benzoyl methane) (Symrise) | 5.00 |
| Eusolex T-AVO (titanium dioxide, silica gel) (Merck) | 4.00 |
| Abil Wax 9801 (cetyl dimethicone) (Degussa-Goldschmidt) | 1.00 |
| Silicare Silicone 41M65 (stearyl dimethicone) (Clariant) | 1.00 |
| SF1550 (phenyl trimethicone) (GE Bayer Silicones) | 2.00 |
| Isoadipate (diisopropyl adipate) (Symrise) | 3.00 |
| Tocopheryl acetate | 0.50 |
| Antaron-Ganex V-216 (PVP/hexadecene copolymer) (ISP Europe) | 0.50 |
| Disodium EDTA | 0.10 |
| Keltrol CG-T (xanthan gum) (CP-Kelko) | 0.50 |
| Phase B | |
| Deionized water | 47.15 |
| Neo Heliopan Hydro (phenylbenzimidazole sulfonic acid) (Symrise) | 2.00 |
| Neo Heliopan AP (disodium phenyldibenzimidazole tetrasulfonate) | 2.00 |
| Preservative | 0.70 |
| Triethanolamine | 2.50 |
| LaraCare A200 (galactoarabinan) (Rahn AG) | 0.25 |
| Hydrolite 5 (pentylene glycol) (Symrise) | 3.00 |
| Perfume oil composition from Example 37 | 0.30 |

Example 55: Shaving Foam

| Ingredients | wt. % |
| --- | --- |
| Phase A | |
| Deionized water | 77.3 |
| Triethanolamine | 4.0 |
| Phase B | |
| Edenor L2 SM (stearic acid, palmitic acid) (Cognis) | 5.3 |
| Laureth-23 | 3.0 |
| Stearyl alcohol | 0.5 |
| Phase C | |
| Preservative | 0.8 |
| Phase D | |
| Sodium lauryl sulfate | 3.0 |
| Perfume oil composition from Example 38 | 1.0 |
| Extrapone seaweed (water, propylene glycol, potassium iodide, *Fucus vesiculosus* extract) (Symrise) | 1.0 |
| Dragosantol (bisabolol, farnesol) (Symrise) | 0.1 |
| Phase E | |
| Propane butane 4.2 bar | 4.0 |

Example 56: Depilatory Formulation

| Ingredients | wt. % |
| --- | --- |
| Phase A | |
| Cetearyl alcohol | 10.0 |
| Ceteareth-12 | 2.0 |
| PCL-Liquid (cetearyl ethyl hexanoate, isopropyl myristate) (Symrise) | 3.0 |
| Dragosantol (bisabolol, farnesol) (Symrise) | 0.1 |
| Edenor L2 SM (stearic acid, palmitic acid) (Cognis) | 1.0 |
| Phase B | |
| Deionized water | 52.2 |
| Urea | 5.0 |
| Neo Dragocid powder (methyl parabene, sorbic acid, dehydroacetic acid, propylparabene) (Symrise) | 0.2 |
| Phase C | |
| Deionized water | 10.0 |
| Calcium thioglycolate | 6.0 |
| Sodium hydroxide solution, 10% | 10.0 |
| Phase D | |
| Perfume oil composition from Example 39 | 0.5 |

Example 57: Softening Rinse Concentrate

| Ingredients | wt. % |
| --- | --- |
| Rewoquat WE 18 (di-(tallow carboxyethyl), hydroxyethyl methyl-ammonium methosulfate) (Goldschmidt Rewo GmbH) | 12.0 |
| Parmetol A 26 (mixture of 5-chloro-2-methyl-2H-isothiazol-3-one and 2-methyl-2H-isothiazol-3-one) (Hoesch Julius) | 0.1 |
| Calcium chloride solution, 25% | 0.4 |
| Water | 86.9 |
| Perfume oil composition from Example 41 | 0.6 |

Example 58: Washing Powder

| Ingredients | wt. % |
| --- | --- |
| Sodium metasilicate pentahydrate | 48.0 |
| Sodium hydrogen carbonate | 15.0 |
| Sodium carbonate peroxyhydrate | 15.0 |
| TAED/sodium carboxymethylcellulose | 5.0 |
| Oxo alcohol C14-15, 8 EO | 3.0 |
| Sodium lauryl sulfate, C12 | 7.0 |
| Trinopal CBS-X (derivatives of 4,4-distyrylbiphenyl) (Ciba) | 0.5 |
| Protease | 0.4 |
| alpha-Amylase | 0.3 |
| Sodium sulfate | 5.5 |
| Perfume oil composition from Example 37 | 0.3 |

Example 59: Liquid Detergent

| Ingredients | wt. % |
| --- | --- |
| Water | 39.7 |
| Disodium distyryl biphenyl disulfonate | 0.1 |
| Cocoa fatty acid | 7.5 |
| Potassium hydroxide solution 50% (Merck) | 4.3 |
| Propan-1,2-diol | 5.0 |
| Trideceth-9 | 12.0 |
| Parmetol A 26 (mixture of 5-chloro-2-methyl-2H-isothiazol-3-one and 2-methyl-2H-isothiazol-3-one) (Hoesch Julius) | 0.2 |
| Sulfonic acid, C13-17-sec-alkyl, sodium salt | 17.0 |
| Triethanolamine | 2.0 |
| Trisodium citrate dihydrate | 5.0 |
| HOESCH PHOS DET 32 D (diethylenetriamine, pentamethylene-phosphonic acid, sodium salt) (Hoesch Julius) | 3.0 |
| Ethyl alcohol 96% | 3.0 |
| Protease | 0.4 |
| alpha-Amylase | 0.3 |
| Perfume oil composition from Example 38 | 0.5 |

Example 60: Dishwashing Concentrate

| Ingredients | wt. % |
| --- | --- |
| Sodium lauryl sulfate | 31.0 |
| Propan-1,2-diol | 6.0 |
| Ethyl alcohol 96% | 7.0 |
| Coco glucoside | 6.0 |
| Coco betaine | 18.0 |
| Water | 31.6 |
| Perfume oil composition from Example 40 | 0.4 |

Example 61: Dishwashing Formulation

| Ingredients | wt. % |
| --- | --- |
| Coco glucoside | 4.0 |
| Sodium lauryl sulfate | 45.0 |
| Coco betaine | 8.0 |
| Ethyl alcohol 96% | 1.0 |
| Water | 41.8 |
| Perfume oil composition from Example 41 | 0.2 |

Example 62: Dishwashing Tablets

| Ingredients | wt. % |
| --- | --- |
| Sodium silicate | 35.00 |
| Trisodium citrate dihydrate | 20.00 |
| Sodium perborate monohydrate | 7.00 |
| Tetraacetylethylenediamine sodium carboxymethylcellulose | 3.00 |
| Protease | 1.00 |
| alpha-Amylase | 0.25 |
| Sodium carbonate | 27.65 |
| Sokalan PA 30 CL granulate (BASF) | 2.00 |
| Sokalan CP 45 granulate (BASF) | 3.00 |
| Plurafac LF 403 (BASF) | 1.00 |
| Perfume oil composition from Example 39 | 0.10 |

Example 63: Bleach

| Ingredients | wt. % |
| --- | --- |
| Decyl dimethyl amine oxide | 3.34 |
| Sodium lauryl sulfate | 4.22 |
| Sodium hypochlorite 12.5% | 30.77 |
| Sodium hydroxide solution, 30% | 1.50 |
| Water | 60.07 |
| Perfume oil composition from Example 37 | 0.10 |

Example 64: All-Purpose Cleaner

| Ingredients | wt. % |
| --- | --- |
| Parmetol A 26 (mixture of 5-chloro-2-methyl-2H-isothiazol-3-one and 2-methyl-2H-isothiazol-3-one) (Hoesch Julius) (Hoesch Julius) | 0.1 |
| Trisodium citrate dihydrate | 3.0 |
| Sodium lauryl sulfate | 30.0 |
| Trideceth-9 | 5.0 |
| Ethyl alcohol 96% | 2.0 |
| Water | 59.6 |
| Perfume oil composition from Example 39 | 0.3 |

Example 65: Toilet Cleaner

| Ingredients | wt. % |
| --- | --- |
| Water | 93.2 |
| Kelzan ASX-T (Biesterfeld Spezialchemie GmbH) | 0.5 |
| Paraffin sulfonate, sodium salt | 1.0 |
| Citric acid | 5.0 |
| Perfume oil composition from Example 38 | 0.3 |

Example 66: Toilet Block

| Ingredients | wt. % |
| --- | --- |
| C12/15-pareth-20 | 4.0 |
| Cocamide MEA | 6.0 |
| C10-13, ABS-Na, powder | 42.0 |
| Sodium sulfate | 42.0 |
| Perfume oil composition from Example 41 | 6.0 |

Example 67: Soap

| Ingredients | wt. % |
| --- | --- |
| Base soap HTS (Hirtler GmbH) | 95.8 |
| Titanium dioxide | 1.0 |
| Water | 2.0 |
| Perfume oil composition from Example 39 | 1.2 |

Example 68: Air Freshener in Alginate Gel

| Ingredients | wt. % |
| --- | --- |
| Deionized water | 86.8 |
| 1,2-Benzisothiazol-3(2H)-one | 0.2 |
| Genugel CI-121 (CP KelcoGermany GmbH) | 2.0 |
| Trideceth-11 | 2.0 |
| Propan-2-ol | 4.0 |
| Perfume oil from Example 41 | 5.0 |

Example 69: Aerosol Air Freshener, Water Based (w/o)

| Ingredients | wt. % |
| --- | --- |
| C12-15 pareth-3 | 0.25 |
| Deceth-8, Ziegler alcohol | 1.00 |
| Deionized water | 22.50 |
| Propellant 4.2 bar | 75.00 |
| Perfume oil from Example 39 | 1.25 |

Example 70: Liquid Air Freshener, Pump Spray

| Ingredients | wt. % |
| --- | --- |
| Deionized water | 90.7 |
| Ethyl alcohol 96% | 4.0 |
| Empilan KCL 11/90 (alcohol C12-15 11 EO) (Stockmeier Chemie GmbH & Co. KG) | 3.0 |
| Propan-2-ol | 1.0 |
| Sodium hydrogen carbonate | 0.2 |
| Parmetol A 26 (mixture of 5-chloro-2-methyl-2h-isothiazol-3-one and 2-methyl-2h-isothiazol-3-one) (Hoesch Julius) | 0.1 |
| Perfume oil composition from Example 40 | 1.0 |

Example 71: Air Freshener (Pump/Wick)

| Ingredients | wt. % |
| --- | --- |
| Deionized water | 67.32 |
| Sequion 40 NA 32 (Polygon Chemie) | 1.25 |
| Triethanolamine | 0.30 |
| Rewoderm (DiNa-ricinol amide MEA-sulfosuccinate) (Goldschmidt AG) | 2.33 |
| Tego Sorb Conc. 50 (alcohol C12-14, ethoxylated (2-EO) + Zn-ricin oleate) (Evonik) | 0.50 |

-continued

| Ingredients | wt. % |
| --- | --- |
| Ethyl alcohol 96% | 20.00 |
| Solubilizer | 3.00 |
| Lactic acid 90% (2-Hydroxypropionic acid) | 0.30 |
| Perfume oil composition from Example 38 | 5.00 |

Example 72: Candles

| Ingredients | wt. % |
| --- | --- |
| Candle wax | 95.0 |
| Perfume oil from Example 37 | 5.0 |

Example 73: Peppermint Type Aroma

| Ingredients | wt. % |
| --- | --- |
| Anethol (4-propenyl-anisol) | 9.0 |
| L-Menthol (natural or synthetic) | 35.0 |
| Peppermint oil *Piperita* type (natural or reconstructed) | 20.0 |
| Peppermint oil *Arvensis* type (natural or reconstructed) | 30.0 |

The addition of 6.0 wt. % of 4-isopropyl-6-methylcyclohex-2-en-1-one from Example 2 imparts an additional sweetness to the aroma base and therefore leads to harmonization of the base.

Example 74: Spearmint Type Aroma

| Ingredients | wt. % |
| --- | --- |
| Anethol (4-propenyl-anisol) | 9.0 |
| L-Menthol (natural or synthetic) | 30.0 |
| Peppermint oil *Piperita* type (natural or reconstructed) | 5.0 |
| Peppermint oil *Arvensis* type (natural or reconstructed) | 5.0 |
| L-Carvone | 15.0 |
| Spearmint oil *Cardiaca* type (natural or reconstructed) | 15.0 |
| Spearmint oil *Spicata* type (natural or reconstructed) | 15.0 |

The addition of 6.0 wt. % of 2,3,4,5-tetramethylcyclohex-2-en-1-one from Example 15 significantly improves the sensory profile of the base, together with a pleasant freshness.

Example 75: Wintergreen Type Aroma

| Ingredients | wt. % |
| --- | --- |
| Anethol (4-propenyl-anisol) | 9.0 |
| L-Menthol (natural or synthetic) | 45.0 |
| Peppermint oil *Piperita* type (natural or reconstructed) | 2.0 |
| Peppermint oil *Arvensis* type (natural or reconstructed) | 3.0 |
| Spearmint oil *Spicata* type (natural or reconstructed) | 1.0 |
| Eugenol (2-methoxy-4-allyl-phenol) | 7.0 |
| *Eucalyptus* oil | 5.0 |
| Methyl salicylate | 20.0 |

The addition of 8.0 wt. % of 3-ethyl-2,5-dimethylcyclohex-2-en-1-one from Example 10 to the aroma base leads to a significant boost effect of the minty notes and imparts an enhanced fresh feel.

Example 76: Eucalyptus Type Aroma

| Ingredients | wt. % |
| --- | --- |
| Anethol (4-propenyl-anisol) | 18.0 |
| L-Menthol (natural or synthetic) | 50.0 |
| Peppermint oil *Piperita* type (natural or reconstructed) | 2.0 |
| Peppermint oil *Arvensis* type (natural or reconstructed) | 3.0 |
| Eucalyptol | 15.0 |
| *Eucalyptus* oil | 5.0 |

The addition of 7.0 wt. % of 2,3,5,5-tetramethylcyclohex-2-en-1-one from Example 18 to the aroma base leads to a pleasant enhancement of the herb notes and imparts a refreshing oral sensation.

Example 77: Cinnamon Type Aroma

| Ingredients | wt. % |
| --- | --- |
| Cinnamaldehyde | 10.0 |
| Anethol (4-propenyl-anisol) | 9.0 |
| Peppermint oil *Piperita* type (natural or reconstructed) | 10.0 |
| Peppermint oil *Arvensis* type (natural or reconstructed) | 15.0 |
| Spearmint oil *Spicata* type (natural or reconstructed) | 8.0 |
| Eugenol (2-methoxy-4-allyl-phenol) | 2.0 |
| L-Menthol (natural or synthetic) | 40.0 |

The addition of 6.0 wt. % of 3-ethyl-5-isopropyl-2-methylcyclohex-2-en-1-one from Example 28 imparts a slight sharp impression to the aroma base and furthermore enhances the sweetness, so that the base is perceived as substantially more rounded and fresher.

Example 78: Ice Candy Type Aroma

| Ingredients | wt. % |
| --- | --- |
| Isoamyl acetate | 2.0 |
| Ethyl butyrate | 0.5 |
| Ethyl vanillin (3-ethoxy-4-hydroxybenzaldehyde) | 2.0 |
| Frambinon ™ [4-(4-hydroxyphenyl)-2-butanone] | 0.5 |
| L-Menthol (natural) | 8.0 |
| 1,2-Propylene glycol | 83.0 |
| Compound from Example 15 | 4.0 |

Example 79: Toothpaste Silica Base

| Ingredients | wt. % |
| --- | --- |
| Deionized water | 26.53 |
| Sorbitol 70% | 45.00 |
| Solbrol M (sodium salt) | 0.15 |
| Trisodium phosphate | 0.10 |
| Saccharine | 0.20 |
| Sodium monofluorophosphate | 1.12 |
| PEG 1500 | 5.00 |
| Sident 9 (abrasive silica) | 10.00 |

| Ingredients | wt. % |
|---|---|
| Sident 22 S (thickening silica) | 8.00 |
| Sodium carboxymethylcellulose | 0.90 |
| Titanium(IV) oxide | 0.50 |
| Sodium lauryl sulfate | 1.50 |
| Aroma from Example 73 | 1.00 |

Example 80: Toothpaste Phosphate Base

| Ingredients | wt. % |
|---|---|
| Deionized water | 36.39 |
| Glycerine | 20.00 |
| Solbrol M (sodium salt) | 0.15 |
| Sodium monofluorophosphate | 0.76 |
| Saccharine | 0.20 |
| Dicalcium phosphate-dihydrate | 36.00 |
| Aerosil ® 200 (Silica) | 3.00 |
| Sodium carboxymethylcellulose | 1.20 |
| Sodium lauryl sulfate (Texapon) | 1.30 |
| Aroma from Example 75 | 1.00 |

Example 81: Toothpaste Calcium Carbonate Base

| Ingredients | wt. % |
|---|---|
| Deionized water | 27.5 |
| Saccharine | 0.2 |
| Solbrol M (sodium salt) | 0.2 |
| Sodium monofluorophosphate | 0.8 |
| Sorbitol 70% | 29.0 |
| Calcium carbonate | 35.0 |
| Sident 22 S (thickening silica) | 2.5 |
| Sodium carboxymethylcellulose | 1.3 |
| Titanium(IV) oxide | 0.5 |
| Sodium lauryl sulfate (SLS) | 2.0 |
| Aroma from Example 74 | 1.00 |

Example 82: Mouthwash Concentrate

| Ingredients | wt. % |
|---|---|
| Ethyl alcohol 96% | 42.00 |
| Cremophor RH 455 | 5.00 |
| Deionized water | 48.67 |
| Allantoin | 0.20 |
| Sodium saccharine 450 | 0.10 |
| Color L-Blue 5000 (1% in water) | 0.03 |
| Aroma from Example 75 | 4.00 |

Example 83: Mouthwash ("Ready to Use" with and without Alcohol)

| Ingredients | I wt. % | II |
|---|---|---|
| Ethyl alcohol 96% | 10.00 | — |
| Cremophor CO 40 | 1.00 | — |
| Cremophor RH 455 | — | 1.80 |
| Benzoic acid | 0.10 | — |
| Deionized water | 83.48 | 87.57 |
| Sorbitol 70% | 5.00 | 10.00 |
| Sodium saccharine 450 | 0.07 | — |
| Color L-Blue 5000 (1% in water) | 0.10 | — |
| Sodium fluoride | — | 0.18 |
| Solbrol M sodium salt | — | 0.10 |
| Pellitorine solution PLM (containing 10% pellitorine) | — | 0.15 |
| Aroma from Example 76 | 0.25 | 0.20 |

Example 84: Chewing Gum with and without Sugar

| Ingredients | I | II |
|---|---|---|
| Gum Base (chewing gum base) | 21.0 | 30.0 |
| Glucose syrup | 16.5 | — |
| Glycerine | 0.5 | — |
| Sugar powdered | 60.0 | — |
| Sorbitol powdered | — | 40. |
| Isomalt powdered | — | 9.5 |
| Xylitol | — | 2.0 |
| Mannitol D | — | 3.0 |
| Aspartame | — | 0.1 |
| Acesulfame K | — | 0.1 |
| Emulgum ™ (soya lecithin, high phospholipid content) | — | 0.3 |
| Sorbitol (70% in water) | — | 13.0 |
| Glycerine | 0.5 | 1.0 |
| Aroma from Example 77 | 2.0 | 1.0 |

Example 85: Hardboiled Candy with and without Sugar

| Ingredients | I | II |
|---|---|---|
| Water | 2.75 | 2.24 |
| Sugar | 60.1 | — |
| Glucose syrup | 36.9 | — |
| Isomalt | — | 94.98 |
| Xylitol | — | 2.40 |
| Sucralose | — | 0.03 |
| Acesulfame K | — | 0.05 |
| Citric acid | — | 0.05 |
| Aroma from Example 78 | 0.25 | 0.25 |

Example 86: Instant Beverage Powder

| Ingredients | wt. % |
|---|---|
| Sugar (saccharose) | 81.5 |
| Citric acid | 11.58 |
| Trisodium citrate | 0.70 |
| Tricalcium phosphate | 0.60 |
| Vitamin C | 0.66 |
| Grindsted ® JU 543 stabilizer system (Danisco) | 0.90 |
| Saccharine | 0.56 |
| Citronella aroma, spray-dried | 1.75 |
| Aroma from Example 77, spray-dried onto maltodextrin (DE 18), dextrose and gum arabic, aroma loading 35% | 1.75 |

Example 87: Odor Enhancer Concentrate

The odor enhancer concentrate given below may be used to be added to base preparations in order to superadditively enhance the olfactory impression of the base preparation, for example forming a particularly valuable fragrance and/or flavor material composition.

| Ingredients | wt. % |
|---|---|
| Rose oxide | 40 |
| 2,3,5,5-Tetramethylcyclohex-2-en-1-one from Example 18 | 60 |

Example 88: Odor Enhancer Concentrate

The odor enhancer concentrate given below may be used to be added to base preparations in order to superadditively enhance the olfactory impression of the base preparation, for example forming a particularly valuable fragrance and/or flavor material composition.

| Ingredients | wt. % |
|---|---|
| Rose oxide | 10 |
| 2,3,5,5-Tetramethylcyclohex-2-en-1-one from Example 18 | 50 |
| 4-Isopropyl-6-methylcyclohex-2-en-1-one from Example 2 | 40 |

What is claimed is:

1. A compound selected from the group consisting of 3-ethyl-2,5-dimethylcyclohex-2-en-1-one (13) 2,3,4,5-tetramethylcyclohex-2-en-1-one (23), 2,3,5,5-tetramethylcyclohex-2-en-1-one (29), 3-ethyl-5-isopropyl-2-methylcyclohex-2-en-1-one (43), and 2-methyl-5-n-propylcyclohex-2-en-1-one (51).

2. A fragrance and/or flavor material composition comprising at least one compound selected from the group consisting of compounds:

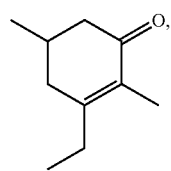
(13)

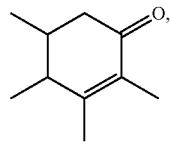
(23)

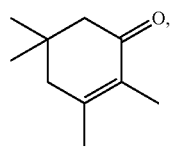
(29)

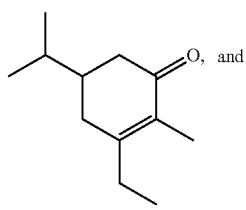
(43)

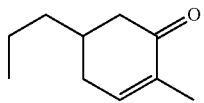
(51)

and wherein compound(s) (13), (23), (29), (43) and (51) are present in the range of from 0.0001 wt. %, through 90 wt. % based on the total weight of the fragrance and/or flavor material composition.

3. The fragrance and/or flavor material composition of claim 2 wherein the at least one compound selected from the group consisting of compounds 2,3,4,5-tetramethylcyclohex-2-en-1-one (23), 3-ethyl-5-isopropyl-2-methylcyclohex-2-en-1-one (43), and 2-methyl-5-n-propylcyclohex-2-en-1-one (51).

4. The fragrance and/or flavor material composition of claim 2, wherein the total amount of the at least one or more compounds (13), (23), (29), (43) and (51) is in the range of from 0.01 wt. %, through 70 wt. % based on the total weight of the fragrance and/or flavor material composition.

5. The fragrance and/or flavor material composition of claim 2, wherein the total amount of the at least one or more compounds (13), (23), (29), (43) and (51) is in the range of from 0.1 wt. %, through 50 wt. % based on the total weight of the fragrance and/or flavor material composition.

6. The fragrance and/or flavor material composition of claim 2, wherein the total amount of the at least one or more compounds of (13), (23), (29), (43) and (51) is in the range of from 0.1 wt. %, through 30 wt. % based on the total weight of the fragrance and/or flavor material composition.

7. The fragrance and/or flavor material composition of claim 2, wherein the total amount of the at least one or more compounds of (13), (23), (29), (43) and (51) is in the range of from 0.1 wt. %, through 10 wt. % based on the total weight of the fragrance and/or flavor material composition.

8. A perfumed and/or aromatized article comprising the fragrance and/or flavor material composition of claim 2.

9. The article of claim 8 further comprising a carrier or a substrate that is in direct contact with at least one or more compounds (13), (23), (29), (43) and (51).

10. A fragrance and/or flavor material composition consisting of at least one compound selected from the group consisting of compounds:

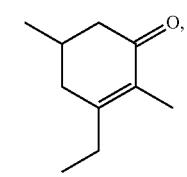
(13)

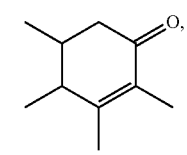
(23)

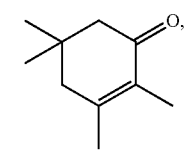
(29)

-continued

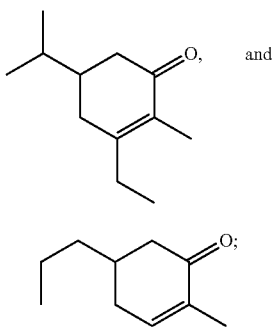 (43)

and

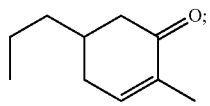 (51)

and, wherein compound(s) (13), (23), (29), (43) and (51) are present in the range of from 0.0001 wt. %, through 90 wt. % based on the total weight of the fragrance and/or flavor material composition.

11. The fragrance and/or flavor material composition of claim 10 which does not contain fragrance and/or flavor materials which have a pyrazine basic structure.

12. The fragrance and/or flavor material composition of claim 2 comprising at least one compound selected from the group consisting of compounds (13) and (23), as a fragrance material having a saffron note.

13. The fragrance and/or flavor material composition of claim 2 comprising at least one compound selected from the group consisting of compounds (13), (23), (29), and (43) as a fragrance material having a leather note.

14. The fragrance and/or flavor material composition of claim 2 comprising at least one compound selected from the group consisting of compounds (13) and (43) as a fragrance material having a green note.

15. The fragrance and/or flavor material composition of claim 2 comprising compound (51) as a fragrance material having an aniseed note.

16. The perfumed and/or aromatized article of claim 8 which is selected from the group consisting of perfume extracts, eau de parfum, eau de toilette, aftershave, eau de cologne, preshave products, splash colognes and perfumed freshening wipes, and the perfuming of acidic, alkaline and neutral cleaning formulations, laundry pretreatment formulations, fabric softeners, washing soaps, washing tablets, disinfectants, surface disinfectants, and of air fresheners in liquid or gel form or deposited on a solid carrier, aerosol sprays, waxes and polishes, body care formulations, cosmetic emulsions of the oil-in-water, water-in-oil and water-in-oil-in-water type, hair care products, hair styling formulations, hair tonics, hair creams and lotions, deodorants and antiperspirants, products for decorative cosmetics, candles, lamp oils, joss-sticks, insecticides, repellents and propellants.

17. The perfumed and/or aromatized article of claim 8 which is a preparation selected from the group consisting of foodstuff, and oral hygiene.

18. The perfumed and/or aromatized article of claim 8 which is a foodstuff selected from the group consisting of bakery products, confectionery, alcoholic and non-alcoholic beverages, instant beverages, meat products, eggs or egg products, cereal products, milk products, products from soya protein or other soybean fractions, fruit preparations, vegetable preparations, snack foods, fat and oil-based products or the emulsions thereof, other ready meals and soups, spices, and seasoning mixtures.

19. The perfumed and/or aromatized article of claim 17 which is a preparation for oral hygiene selected from the group consisting of toothpastes, tooth gels, tooth powders, mouth washes and chewing gums.

20. The perfumed and/or aromatized article of claim 17 which is a foodstuff containing bases, excipients and additives selected from the group consisting of water, mixtures of fresh or processed, plant or animal bases or raw materials, digestible or indigestible carbohydrates, sugar alcohols, natural or hydrogenated fats, oils, fatty acids or the salts thereof, proteinogenic or non-proteinogenic amino acids and related compounds, peptides, native or processed proteins, enzymes, nucleic acids, nucleotides, flavor correctors for unpleasant flavor impressions, further flavor modulators for other generally not unpleasant flavor impressions, inositol phosphate, nucleotides, sodium glutamate or 2-phenoxypropionic acid, emulsifiers, preservatives, antioxidants, chelators, organic or inorganic acidifiers, bitters, mineral salts, substances preventing enzymatic browning, essential oils, plant extracts, natural or synthetic dyes or pigments, spices, trigeminally active substances or plant extracts containing such trigeminally active substances, synthetic, natural or naturally identical flavor materials or fragrance materials and odor correctors.

* * * * *